(12) United States Patent
Zhang et al.

(10) Patent No.: US 10,987,418 B2
(45) Date of Patent: Apr. 27, 2021

(54) POLYPEPTIDE CARRIER FOR PRESENTING TARGET POLYPEPTIDE AND USES THEREOF

(71) Applicants: XIAMEN UNIVERSITY, Xiamen (CN); YANG SHENG TANG COMPANY, LTD., Hangzhou (CN)

(72) Inventors: Tianying Zhang, Xiamen (CN); Quan Yuan, Xiamen (CN); Xueran Guo, Xiamen (CN); Minxi Wei, Xiamen (CN); Xiaozhen Kang, Xiamen (CN); Jun Zhang, Xiamen (CN); Ningshao Xia, Xiamen (CN)

(73) Assignees: XIAMEN UNIVERSITY, Xiamen (CN); YANG SHENG TANG COMPANY, LTD., Hangzhou (CN)

( * ) Notice: Subject to any disclaimer, the term of this patent is extended or adjusted under 35 U.S.C. 154(b) by 20 days.

(21) Appl. No.: 16/484,366

(22) PCT Filed: Feb. 5, 2018

(86) PCT No.: PCT/CN2018/075199
§ 371 (c)(1),
(2) Date: Aug. 7, 2019

(87) PCT Pub. No.: WO2018/149315
PCT Pub. Date: Aug. 23, 2018

(65) Prior Publication Data
US 2020/0147205 A1 May 14, 2020

(30) Foreign Application Priority Data

Feb. 17, 2017 (CN) .......................... 201710085194.3

(51) Int. Cl.
| | | |
|---|---|---|
| *A61K 39/39* | (2006.01) | |
| *C07H 21/04* | (2006.01) | |
| *A61K 39/00* | (2006.01) | |
| *A61K 39/395* | (2006.01) | |
| *A61P 35/00* | (2006.01) | |
| *A61K 39/29* | (2006.01) | |
| *A61P 31/20* | (2006.01) | |
| *C07K 14/005* | (2006.01) | |
| *C12N 7/00* | (2006.01) | |

(52) U.S. Cl.
CPC ............ *A61K 39/292* (2013.01); *A61P 31/20* (2018.01); *C07K 14/005* (2013.01); *C12N 7/00* (2013.01); *A61K 2039/5258* (2013.01); *C12N 2730/10122* (2013.01); *C12N 2730/10134* (2013.01)

(58) Field of Classification Search
CPC .............. A61K 39/39; A61K 2039/53; A61K 2039/55561; A61K 31/404; A61P 35/00
See application file for complete search history.

(56) References Cited

U.S. PATENT DOCUMENTS

2005/0025782 A1  2/2005  Milich et al.
2006/0094017 A1  5/2006  Conley et al.

FOREIGN PATENT DOCUMENTS

| CN | 102127554 A | 7/2011 |
|---|---|---|
| CN | 104211784 A | 12/2014 |
| CN | 104341506 A | 2/2015 |
| CN | 106480070 A | 3/2017 |
| CN | 106905434 A | 6/2017 |
| CN | 106986943 A | 7/2017 |
| EP | 3 342 866 A1 | 7/2018 |
| WO | WO 2004/073659 A2 | 9/2004 |

OTHER PUBLICATIONS

Yang, L., HBV core particles as carriers of B cell/T cell epitopes, Foreign Medical Sciences, Section of Biological products for Prophylaxis, Diagnosis and Therapy, 2002, 25(5):Abstract 2 pages.*
Florian Schödel et al., "The Position of Heterologous Epitopes Inserted in Hepatitis B Virus Core Particles Determines Their Immunogenicity", Journal of Virology, 1992, vol. 66, No. 1, pp. 106-114.
Combined Chinese Office Action and Search Report dated Feb. 7, 2020 in Chinese Patent Application No. 201810110910.3, citing documents AO through AQ therein, 13 pages.
Office Action dated Aug. 30, 2019 in Korean Patent Application No. 10-2018-7008233 (with English translation), citing document AX therein, 7 pages.
Whitacre, D. C. et al."Use of hepadnavirus core proteins as vaccine platforms", Expert Rev Vaccines 8(11), Nov. 2009, 15 pages.
International Search Report dated May 4, 2018 in PCT/CN2018/075199 filed Feb. 5, 2018.
Yang, J., "HBV core particles as carriers of B cell/T cell epitopes", Foreign Medical Sciences, Section of Biological Products for Prophylaxis, Diagnosis and Therapy, 2002, 8 pages (with English Abstract).

(Continued)

*Primary Examiner* — Barry A Chestnut
(74) *Attorney, Agent, or Firm* — Oblon, McClelland, Maier & Neustadt, L.L.P.

(57) ABSTRACT

The invention relates to a polypeptide carrier for presenting a target polypeptide, and use thereof. In particular, the invention relates to a nucleic acid molecule, comprising a nucleotide sequence encoding a polypeptide carrier, and being used for insertion of a nucleotide sequence encoding a target polypeptide. In addition, the invention further relates to a recombinant protein comprising the polypeptide carrier and a target polypeptide. Furthermore, the invention further relates to use of the nucleic acid molecule and the recombinant protein. In addition, the invention further relates to a vaccine or a pharmaceutical composition useful for preventing, alleviating or treating HBV infection or a disease associated with HBV infection (e.g., hepatitis B), comprising a recombinant protein comprising the polypeptide carrier of the invention and an epitope from HBV.

19 Claims, 15 Drawing Sheets

Specification includes a Sequence Listing.

(56) References Cited

OTHER PUBLICATIONS

Drexler, J. F. et al.. "Bats carry pathogenic hepadnaviruses antigenically related to hepatitis B virus and capable of infecting human hepatocytes", PNAS, vol. 110, No. 40, 2013, 7 pages.

Yang, H-J. et al., "Construction of Peptide Display Vector Based on HBV Core Protein", Journal of Xiamen University (Natural Science), vol. 43, No. 4, 2004, 5 pages (with English Abstract).

Zhang, J-N. et al., "Secretion Expression of Hepatitis B Core Antigen Particles Harboring HEV Receptor-associated Epitope in *Pichia pastoris*", Journal of Xiamen University (Natural Science), vol. 48, No. 1, 2009, 6 pages (with English Abstract).

Long, J. et al., "Cloning, Expression, Separation and Purification of Particle-Like Protein Loading CETP Polypeptide Epitopes", Pharmaceutical Biotechnology, vol. 13, No. 4, 2006, 7 pages (with English Abstract).

Shoedel, F. et al., "Hybrid hepatitis B virus core antigen as a vaccine carrier moiety: I. Presentation of foreign epitopes", Journal of Biotechnology, vol. 44, 1996, pp. 91-96.

Roose, K. et al., "Hepatitis B core-based virus-like particles to present heterologous epitopes", Expert Reviews Vaccines, vol. 12, No. 2, 2013, pp. 183-198.

"Hepatitis B virus isolate HBV-N10, complete genome", XP002787438, Database EMBL [online], retrieved from EBI accession No. EMBL:AY707087, 2004, 3 pages.

* cited by examiner

RBHBcAg carrier         flexible peptide      flexible peptide 1                       77    target peptide   82                    149           189

TBHBcAg carrier         flexible peptide      flexible peptide 1                       79    target peptide   84                    153           188

HBHBcAg carrier         flexible peptide      flexible peptide 1                       77    target peptide   82                    149           189

Fig. 1

RBHBcAg149-SEQ60
 TBHBcAg153-SEQ60
 RBHBcAg149-SEQ61
 TBHBcAg153-SEQ61
 RBHBcAg149-SEQ62
 TBHBcAg153-SEQ62

```
                            SEQUENCE LISTING

<160> NUMBER OF SEQ ID NOS: 100

<210> SEQ ID NO 1
<211> LENGTH: 189
<212> TYPE: PRT
<213> ORGANISM: Artificial Sequence
<220> FEATURE:
<223> OTHER INFORMATION: roundleaf bat HBV

<400> SEQUENCE: 1

Met Asp Ile Asp Pro Tyr Lys Glu Phe Gly Ala Ser Ser Gln Leu Ile
1               5                   10                  15

Ser Phe Leu Pro Glu Asp Phe Pro Asn Leu Ala Glu Leu Val Glu
                20                  25                  30

Thr Thr Thr Ala Leu Tyr Glu Glu Leu Val Gly Lys Glu His Cys
                35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Pro Leu
65                  70                  75                  80

Ile Gln Asp Ala Ile Val Gln Gln Val Gln Ala Ser Val Gly Leu Arg
                85                  90                  95

Met Arg Gln Leu Met Trp Phe His Leu Ser Cys Leu Thr Phe Gly Gln
                100                 105                 110

Pro Thr Val Ile Glu Phe Leu Val Ser Phe Gly Thr Trp Ile Arg Thr
                115                 120                 125

Pro Gln Ala Tyr Arg Pro Pro Asn Ala Pro Ile Leu Ser Thr Leu Pro
                130                 135                 140

Glu His Thr Ile Val Arg Arg Arg Gly Gly Ser Arg Ala Thr Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ala Ser Ser Asn Cys
                180                 185

<210> SEQ ID NO 2
<211> LENGTH: 188
<212> TYPE: PRT
<213> ORGANISM: Artificial Sequence
<220> FEATURE:
<223> OTHER INFORMATION: tent-making bat HBV

<400> SEQUENCE: 2

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
                20                  25                  30

Gln Leu Leu Glu Ser Val Asn Ala Leu Tyr Glu Asp Glu Leu Thr Gly
                35                  40                  45

Pro Asn His Cys Ser Pro His His Thr Ala Leu Arg His Leu Ile Met
    50                  55                  60
```

```
Cys Gly Val Glu Leu Arg Asp Phe Ile Asp Trp Met His Glu Gln Gly
 65                  70                  75                  80

Leu Ser Pro Asp Ala Asp Ala Leu Leu Ala Gly Tyr Leu Arg Ser Lys
                 85                  90                  95

Tyr Leu Lys His Ile Thr Lys Ala Ile Trp Tyr His Leu Ser Cys Leu
            100                 105                 110

Thr Phe Gly Lys Gln Thr Val His Glu Tyr Leu Val Ser Phe Gly Thr
        115                 120                 125

Trp Ile Arg Thr Pro Ala Ala Tyr Arg Pro Val Asn Ala Pro Ile Leu
    130                 135                 140

Thr Thr Leu Pro Glu Thr Ser Val Ile Arg Arg Pro Ala Ser Arg
145                 150                 155                 160

Arg Ser Thr Pro Ser Pro Arg Arg Arg Ser Gln Ser Pro Arg Arg
                165                 170                 175

Arg Arg Ser Pro Ser Pro Arg Pro Ala Ser Asn Cys
            180                 185
```

<210> SEQ ID NO 3
<211> LENGTH: 189
<212> TYPE: PRT
<213> ORGANISM: Artificial Sequence
<220> FEATURE:
<223> OTHER INFORMATION: horseshoe bat HBV

<400> SEQUENCE: 3

```
Met Asp Ile Asp Pro Tyr Lys Glu Phe Gly Ala Ser Ser Gln Leu Val
  1               5                  10                  15

Ser Phe Leu Pro Ala Asp Phe Phe Pro Ala Leu Asn Asp Leu Val Glu
                 20                  25                  30

Thr Ser Val Ala Leu Tyr Glu Glu Asp Leu Val Gly Lys Glu His Cys
            35                  40                  45

Ser Pro His His Ala Ala Leu Arg Ala Leu Leu Asn Cys Trp Glu Glu
        50                  55                  60

Thr Val Arg Leu Ile Thr Trp Val Arg Ala Thr Val Glu Gly Gln Pro
 65                  70                  75                  80

Val Gln Asp Ala Ile Ile Gly Tyr Val Gln Thr Thr Val Gly Leu Arg
                 85                  90                  95

Met Arg Gln Gln Ile Trp Phe His Leu Ser Cys Leu Thr Phe Gly Gln
            100                 105                 110

Gln Thr Val Ile Glu Phe Leu Val Ser Phe Gly Thr Trp Met Arg Thr
        115                 120                 125

Pro Ala Ala Tyr Arg Pro Pro Asn Ala Pro Ile Leu Ser Thr Leu Pro
    130                 135                 140

Glu His Thr Val Ile Arg Arg Gly Asn Pro Arg Ala Pro Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ala Pro Ser Asn Cys
            180                 185
```

<210> SEQ ID NO 4
<211> LENGTH: 210
<212> TYPE: PRT
<213> ORGANISM: Artificial Sequence
<220> FEATURE:
<223> OTHER INFORMATION: RBHBcAg189 carrier

<400> SEQUENCE: 4

```
Met Asp Ile Asp Pro Tyr Lys Glu Phe Gly Ala Ser Ser Gln Leu Ile
1               5                   10                  15
Ser Phe Leu Pro Glu Asp Phe Phe Pro Asn Leu Ala Glu Leu Val Glu
            20                  25                  30
Thr Thr Thr Ala Leu Tyr Glu Glu Leu Val Gly Lys Glu His Cys
        35                  40                  45
Ser Pro His His Thr Ala Leu Arg Ser Leu Leu Asn Cys Trp Gly Glu
    50                  55                  60
Thr Val Arg Leu Ile Thr Trp Val Arg Asn Ser Val Glu Gly Gly Gly
65                  70                  75                  80
Gly Gly Ser Gly Gly Gly Gly Thr Gly Ser Glu Phe Gly Gly Gly Gly
            85                  90                  95
Ser Gly Gly Gly Gly Ser Gln Asp Ala Ile Val Gln Gln Val Gln Ala
            100                 105                 110
Ser Val Gly Leu Arg Met Arg Gln Leu Met Trp Phe His Leu Ser Cys
            115                 120                 125
Leu Thr Phe Gly Gln Pro Thr Val Ile Glu Phe Leu Val Ser Phe Gly
    130                 135                 140
Thr Trp Ile Arg Thr Pro Gln Ala Tyr Arg Pro Asn Ala Pro Ile
145                 150                 155                 160
Leu Ser Thr Leu Pro Glu His Thr Ile Val Arg Arg Arg Gly Gly Ser
                165                 170                 175
Arg Ala Thr Arg Ser Pro Arg Arg Arg Thr Pro Ser Pro Arg Arg Arg
            180                 185                 190
Arg Ser Gln Ser Pro Arg Arg Arg Ser Gln Ser Pro Ala Ser Ser
            195                 200                 205
Asn Cys
    210
```

```
<210> SEQ ID NO 5
<211> LENGTH: 170
<212> TYPE: PRT
<213> ORGANISM: Artificial Sequence
<220> FEATURE:
<223> OTHER INFORMATION: RBHBcAg149 carrier
```

<400> SEQUENCE: 5

```
Met Asp Ile Asp Pro Tyr Lys Glu Phe Gly Ala Ser Ser Gln Leu Ile
1               5                   10                  15
Ser Phe Leu Pro Glu Asp Phe Phe Pro Asn Leu Ala Glu Leu Val Glu
            20                  25                  30
Thr Thr Thr Ala Leu Tyr Glu Glu Leu Val Gly Lys Glu His Cys
        35                  40                  45
Ser Pro His His Thr Ala Leu Arg Ser Leu Leu Asn Cys Trp Gly Glu
    50                  55                  60
Thr Val Arg Leu Ile Thr Trp Val Arg Asn Ser Val Glu Gly Gly Gly
65                  70                  75                  80
Gly Gly Ser Gly Gly Gly Gly Thr Gly Ser Glu Phe Gly Gly Gly Gly
            85                  90                  95
Ser Gly Gly Gly Gly Ser Gln Asp Ala Ile Val Gln Gln Val Gln Ala
            100                 105                 110
Ser Val Gly Leu Arg Met Arg Gln Leu Met Trp Phe His Leu Ser Cys
            115                 120                 125
Leu Thr Phe Gly Gln Pro Thr Val Ile Glu Phe Leu Val Ser Phe Gly
```

```
                 130                 135                 140
Thr Trp Ile Arg Thr Pro Gln Ala Tyr Arg Pro Asn Ala Pro Ile
145                 150                 155                 160

Leu Ser Thr Leu Pro Glu His Thr Ile Val
                165                 170

<210> SEQ ID NO 6
<211> LENGTH: 209
<212> TYPE: PRT
<213> ORGANISM: Artificial Sequence
<220> FEATURE:
<223> OTHER INFORMATION: TBHBcAg188 carrier

<400> SEQUENCE: 6

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
        50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Glu Phe Gly Gly
                85                  90                  95

Gly Gly Ser Gly Gly Gly Ser Asp Ala Asp Ala Leu Leu Ala Gly
                100                 105                 110

Tyr Leu Arg Ser Lys Tyr Leu Lys His Ile Thr Lys Ala Ile Trp Tyr
            115                 120                 125

His Leu Ser Cys Leu Thr Phe Gly Lys Gln Thr Val His Glu Tyr Leu
        130                 135                 140

Val Ser Phe Gly Thr Trp Ile Arg Thr Pro Ala Ala Tyr Arg Pro Val
145                 150                 155                 160

Asn Ala Pro Ile Leu Thr Thr Leu Pro Glu Thr Ser Val Ile Arg Arg
                165                 170                 175

Arg Pro Ala Ser Arg Arg Ser Thr Pro Ser Pro Arg Arg Arg Arg Ser
            180                 185                 190

Gln Ser Pro Arg Arg Arg Arg Ser Pro Ser Pro Arg Pro Ala Ser Asn
        195                 200                 205

Cys

<210> SEQ ID NO 7
<211> LENGTH: 174
<212> TYPE: PRT
<213> ORGANISM: Artificial Sequence
<220> FEATURE:
<223> OTHER INFORMATION: TBHBcAg153 carrier

<400> SEQUENCE: 7

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
```

```
                                     50                       55                       60

Cys Gly Val Glu Leu Arg Asp Phe Ile Asp Trp Met His Glu Gln Gly
 65                      70                       75                       80

Gly Gly Gly Gly Ser Gly Gly Gly Thr Gly Ser Glu Phe Gly Gly
                         85                       90                       95

Gly Gly Ser Gly Gly Gly Ser Asp Ala Asp Ala Leu Leu Ala Gly
                        100                      105                      110

Tyr Leu Arg Ser Lys Tyr Leu Lys His Ile Thr Lys Ala Ile Trp Tyr
                        115                      120                      125

His Leu Ser Cys Leu Thr Phe Gly Lys Gln Thr Val His Glu Tyr Leu
                        130                      135                      140

Val Ser Phe Gly Thr Trp Ile Arg Thr Pro Ala Ala Tyr Arg Pro Val
145                      150                      155                      160

Asn Ala Pro Ile Leu Thr Thr Leu Pro Glu Thr Ser Val Ile
                        165                      170

<210> SEQ ID NO 8
<211> LENGTH: 210
<212> TYPE: PRT
<213> ORGANISM: Artificial Sequence
<220> FEATURE:
<223> OTHER INFORMATION: HBHBcAg189 carrier

<400> SEQUENCE: 8

Met Asp Ile Asp Pro Tyr Lys Glu Phe Gly Ala Ser Ser Gln Leu Val
  1                     5                       10                      15

Ser Phe Leu Pro Ala Asp Phe Phe Pro Ala Leu Asn Asp Leu Val Glu
                        20                      25                       30

Thr Ser Val Ala Leu Tyr Glu Glu Asp Leu Val Gly Lys Glu His Cys
                        35                      40                       45

Ser Pro His His Ala Ala Leu Arg Ala Leu Leu Asn Cys Trp Glu Glu
                        50                      55                       60

Thr Val Arg Leu Ile Thr Trp Val Arg Ala Thr Val Glu Gly Gly Gly
 65                     70                       75                       80

Gly Gly Ser Gly Gly Gly Thr Gly Ser Glu Phe Gly Gly Gly
                        85                      90                       95

Ser Gly Gly Gly Ser Gln Asp Ala Ile Ile Gly Tyr Val Gln Thr
                        100                     105                      110

Thr Val Gly Leu Arg Met Arg Gln Gln Ile Trp Phe His Leu Ser Cys
                        115                     120                      125

Leu Thr Phe Gly Gln Gln Thr Val Ile Glu Phe Leu Val Ser Phe Gly
                        130                     135                      140

Thr Trp Met Arg Thr Pro Ala Ala Tyr Arg Pro Pro Asn Ala Pro Ile
145                      150                     155                      160

Leu Ser Thr Leu Pro Glu His Thr Val Ile Arg Arg Gly Asn Pro
                        165                     170                      175

Arg Ala Pro Arg Ser Pro Arg Arg Thr Pro Ser Pro Arg Arg
                        180                     185                      190

Arg Ser Gln Ser Pro Arg Arg Arg Ser Gln Ser Pro Ala Pro Ser
                        195                     200                      205

Asn Cys
    210

<210> SEQ ID NO 9
<211> LENGTH: 170
<212> TYPE: PRT
```

<213> ORGANISM: Artificial Sequence
<220> FEATURE:
<223> OTHER INFORMATION: HBHBcAg149 carrier

<400> SEQUENCE: 9

```
Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Gln Asp Ala Ile Ile Gly Tyr Val Gln Thr
            100                 105                 110

Thr Val Gly Leu Arg Met Arg Gln Gln Ile Trp Phe His Leu Ser Cys
        115                 120                 125

Leu Thr Phe Gly Gln Gln Thr Val Ile Glu Phe Leu Val Ser Phe Gly
    130                 135                 140

Thr Trp Met Arg Thr Pro Ala Ala Tyr Arg Pro Asn Ala Pro Ile
145                 150                 155                 160

Leu Ser Thr Leu Pro Glu His Thr Val Ile
                165                 170
```

<210> SEQ ID NO 10
<211> LENGTH: 204
<212> TYPE: PRT
<213> ORGANISM: Artificial Sequence
<220> FEATURE:
<223> OTHER INFORMATION: HBcAg183 carrier

<400> SEQUENCE: 10

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Arg Glu Leu Val Val Ser Tyr Val Asn Val
            100                 105                 110

Asn Met Gly Leu Lys Ile Arg Gln Leu Leu Trp Phe His Ile Ser Cys
        115                 120                 125

Leu Thr Phe Gly Arg Glu Thr Val Leu Glu Tyr Leu Val Ser Phe Gly
    130                 135                 140

Val Trp Ile Arg Thr Pro Pro Ala Tyr Arg Pro Gln Asn Ala Pro Ile
145                 150                 155                 160
```

Leu Ser Thr Leu Pro Glu Thr Thr Val Val Arg Arg Arg Gly Arg Ser
            165                 170                 175

Pro Arg Arg Arg Thr Pro Ser Pro Arg Arg Arg Ser Gln Ser Pro
        180                 185                 190

Arg Arg Arg Arg Ser Gln Ser Arg Glu Ser Gln Cys
        195                 200

<210> SEQ ID NO 11
<211> LENGTH: 170
<212> TYPE: PRT
<213> ORGANISM: Artificial Sequence
<220> FEATURE:
<223> OTHER INFORMATION: HBcAg149 carrier

<400> SEQUENCE: 11

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Glu Phe Gly Gly Gly Gly
                85                  90                  95

Ser Gly Gly Gly Gly Ser Arg Glu Leu Val Val Ser Tyr Val Asn Val
            100                 105                 110

Asn Met Gly Leu Lys Ile Arg Gln Leu Leu Trp Phe His Ile Ser Cys
        115                 120                 125

Leu Thr Phe Gly Arg Glu Thr Val Leu Glu Tyr Leu Val Ser Phe Gly
    130                 135                 140

Val Trp Ile Arg Thr Pro Pro Ala Tyr Arg Pro Gln Asn Ala Pro Ile
145                 150                 155                 160

Leu Ser Thr Leu Pro Glu Thr Thr Val Val
            165                 170

<210> SEQ ID NO 12
<211> LENGTH: 633
<212> TYPE: DNA
<213> ORGANISM: Artificial Sequence
<220> FEATURE:
<223> OTHER INFORMATION: nucleotide sequence encoding RBHBcAg189 carrier

<400> SEQUENCE: 12
atggacattg atccttataa agaatttgga gcttcatctc aactgatctc tttcttgcct     60
gaggactttt tcccaaacct tgcagaattg gtcgagacca ccacagctct ctatgaagaa    120
gaattagtag gtaaggagca ttgctcccct caccatactg ctttacgatc cttgctaaat    180
tgctggggag agactgttag attaataact tgggtcagga actctgtgga gggaggtgga    240
ggtggttctg gaggtggtgg tactggatcc gaattcggtg gtggaggttc aggaggaggt    300
ggttcccaag atgccattgt ccagcaagtt caggcctcgg tgggcctgcg catgagacag    360
ttaatgtggt ccatctctcc atgcctaaca tttggacagc ccactgtcat agaatttctg    420
gtctcttttg aacatggat cagaaccccg caagcttaca gaccccctaa tgcacccatt    480
ctctcgactc ttccggagca tacaatcgtt aggagaagag gaggttcacg cgctactagg    540

```
tccccccgaa ggcgcactcc ctctcctcgc cgacgcagat ctcaatcgcc gcgtcgccgc    600
agatctcagt ctccagcttc ctccaactgc taa                                633

<210> SEQ ID NO 13
<211> LENGTH: 510
<212> TYPE: DNA
<213> ORGANISM: Artificial Sequence
<220> FEATURE:
<223> OTHER INFORMATION: nucleotide sequence encoding RBHBcAg149 carrier

<400> SEQUENCE: 13
atggacattg atccttataa agaatttgga gcttcatctc aactgatctc tttcttgcct    60
gaggactttt tcccaaacct tgcagaattg gtcgagacca ccacagctct ctatgaagaa   120
gaattagtag gtaaggagca ttgctcccct caccatactg ctttacgatc cttgctaaat   180
tgctggggag agactgttag attaataact tgggtcagga actctgtgga gggaggtgga   240
ggtggttctg gaggtggtgg tactggatcc gaattcggtg gtggaggttc aggaggaggt   300
ggttcccaag atgccattgt ccagcaagtt caggcctcgg tgggcctgcg catgagacag   360
ttaatgtggt tccatctctc atgcctaaca tttggacagc ccactgtcat gaatttctg    420 gtctcttttg aacatggat cagaaccccg caagcttaca ccccctaa tgcacccatt     480 ctctcgactc ttccggagca tacaatcgtt                                    510

<210> SEQ ID NO 14
<211> LENGTH: 630
<212> TYPE: DNA
<213> ORGANISM: Artificial Sequence
<220> FEATURE:
<223> OTHER INFORMATION: nucleotide sequence encoding TBHBcAg188 carrier

<400> SEQUENCE: 14
atggaaaacc ttgaaagact tgacatctat aaagaatttg gagtctctga tgtcttggtg    60
tctttcttac ctgatgattt cttccaact ttacagcaac ttttggaatc agtgaatgcc   120
ctatatgagg atgaactcac tgggcctaat cactgttctc cccatcatac tgccttaagg   180
cacttgatta tgtgtggggt agaattaaga gatttttattg attggatgca tgaacagggg   240
ggtggaggtg gttctggagg tggtggtact ggatccgaat tcggtggtgg aggttcagga   300
ggaggtggtt ccgatgcaga cgctcttttg gctggttacc ttcgatccaa atatcttaaa   360
catattacca aggctatttg gtatcattta agctgtttga cctttggtaa gcaaacagtg   420
catgaatacc tggtatcctt tggcacctgg atcagaaccc cagctgcata tagaccagtg   480
aatgcaccca ttctcaccac tcttccggaa acttcagtta tcagaagaag gcctgcctcc   540
agaagatcta ctccctctcc tcgcagacgc cgatctcaat caccgcgccg ccgccgctct   600
ccatctccaa gaccagcaag caattgctga                                    630

<210> SEQ ID NO 15
<211> LENGTH: 522
<212> TYPE: DNA
<213> ORGANISM: Artificial Sequence
<220> FEATURE:
<223> OTHER INFORMATION: nucleotide sequence encoding TBHBcAg153 carrier

<400> SEQUENCE: 15
atggaaaacc ttgaaagact tgacatctat aaagaatttg gagtctctga tgtcttggtg    60
tctttcttac ctgatgattt cttccaact ttacagcaac ttttggaatc agtgaatgcc   120
```

```
ctatatgagg atgaactcac tgggcctaat cactgttctc cccatcatac tgccttaagg    180
cacttgatta tgtgtggggt agaattaaga gattttattg attggatgca tgaacagggg    240
ggtggaggtg gttctggagg tggtggtact ggatccgaat cggtggtgg aggttcagga     300 ggaggtggtt ccgatgcaga cgctcttttg gctggttacc ttcgatccaa atatcttaaa    360
catattacca aggctatttg gtatcattta agctgtttga cctttggtaa gcaaacagtg    420
catgaatacc tggtatcctt tggcacctgg atcagaaccc cagctgcata tagaccagtg    480
aatgcaccca ttctcaccac tcttccggaa acttcagtta tc                      522
```

```
<210> SEQ ID NO 16
<211> LENGTH: 633
<212> TYPE: DNA
<213> ORGANISM: Artificial Sequence
<220> FEATURE:
<223> OTHER INFORMATION: nucleotide sequence encoding HBHBcAg189 carrier

<400> SEQUENCE: 16
atggacattg atccttataa agagttcggt gcttcatctc aacttgtctc cttttttgcct    60 gctgacttct ttcccgcctt gaacgacctg gtggaaactt cggtggcctt atatgaggaa   120
gaccttgtag gtaaggagca ttgctcccct catcatgcag ccttaagggc cctacttaat   180
tgctgggagg aaacagtcag actgattacc tgggtccgtg ccacagtaga gggaggtgga   240
ggtggttctg gaggtggtgg tactggatcc gaattcggtg gtggaggttc aggaggaggt   300
ggttcccagg atgccatcat cggttatgtc cagactacgg tgggcctacg catgagacaa   360
cagatctggt tccatctctc atgccttact tttgggcagc agactgtgat agagttcctg   420
gtctcatttg ggacatggat gagaactcca gccgcctata daccccccaa tgcacccatt   480
ttatcaactc ttccagagca cacagtcatt aggagaagag gaaatcccgg tgctcctagg   540
tcccccagaa ggcgcactcc ctctcctcgc cgacgcagat ctcaatctcc gcgtcgccgg   600
agatctcaat ctccagctcc ctccaactgc taa                                633
```

```
<210> SEQ ID NO 17
<211> LENGTH: 510
<212> TYPE: DNA
<213> ORGANISM: Artificial Sequence
<220> FEATURE:
<223> OTHER INFORMATION: nucleotide sequence encoding HBHBcAg149 carrier

<400> SEQUENCE: 17
atggacattg atccttataa agagttcggt gcttcatctc aacttgtctc cttttttgcct    60 gctgacttct ttcccgcctt gaacgacctg gtggaaactt cggtggcctt atatgaggaa   120
gaccttgtag gtaaggagca ttgctcccct catcatgcag ccttaagggc cctacttaat   180
tgctgggagg aaacagtcag actgattacc tgggtccgtg ccacagtaga gggaggtgga   240
ggtggttctg gaggtggtgg tactggatcc gaattcggtg gtggaggttc aggaggaggt   300
ggttcccagg atgccatcat cggttatgtc cagactacgg tgggcctacg catgagacaa   360
cagatctggt tccatctctc atgccttact tttgggcagc agactgtgat agagttcctg   420
gtctcatttg ggacatggat gagaactcca gccgcctata daccccccaa tgcacccatt   480
ttatcaactc ttccagagca cacagtcatt                                    510
```

```
<210> SEQ ID NO 18
<211> LENGTH: 615
<212> TYPE: DNA
<213> ORGANISM: Artificial Sequence
```

```
<220> FEATURE:
<223> OTHER INFORMATION: nucleotide sequence encoding HBcAg183 carrier

<400> SEQUENCE: 18
atggacattg atccatataa agaatttgga gcttctgtgg agttactctc ttttttgcct      60
tccgacttct ttccttctat ccgagatctc ctcgacaccg cctctgctct gtatcgggag     120
gccttagagt ctccggaaca ttgttcacct caccatacgg cactcaggca agctattctg     180
tgttggggtg agttgatgaa tctagccacc tgggtgggaa gtaatttgga agatggtgga     240
ggtggttctg gaggtggtgg tactggatcc gaattcggtg gtggaggttc aggaggaggt     300
ggttccaggg aactagtagt cagctatgtc aacgttaata tgggcctaaa aatcagacaa     360
ctattgtggt ttcacatttc ctgtcttact tttgggagag aaactgttct tgaatatttg     420
gtgtcttttg gagtgtggat cgcactcct cctgcatata gaccacaaaa tgcccctatc      480
ttatcaacac ttccggaaac tactgttgtt cgtcgccgag gccgtagccc gcgacgacgt     540
accccgagcc cgcgtcgacg tcgcagccag agcccgcgcc gtcgtcgcag ccagagccgt     600
gaaagccagt gctaa                                                     615

<210> SEQ ID NO 19
<211> LENGTH: 510
<212> TYPE: DNA
<213> ORGANISM: Artificial Sequence
<220> FEATURE:
<223> OTHER INFORMATION: nucleotide sequence encoding HBcAg149 carrier

<400> SEQUENCE: 19
atggacattg atccatataa agaatttgga gcttctgtgg agttactctc ttttttgcct      60
tccgacttct ttccttctat ccgagatctc ctcgacaccg cctctgctct gtatcgggag     120
gccttagagt ctccggaaca ttgttcacct caccatacgg cactcaggca agctattctg     180
tgttggggtg agttgatgaa tctagccacc tgggtgggaa gtaatttgga agatggtgga     240
ggtggttctg gaggtggtgg tactggatcc gaattcggtg gtggaggttc aggaggaggt     300
ggttccaggg aactagtagt cagctatgtc aacgttaata tgggcctaaa aatcagacaa     360
ctattgtggt ttcacatttc ctgtcttact tttgggagag aaactgttct tgaatatttg     420
gtgtcttttg gagtgtggat cgcactcct cctgcatata gaccacaaaa tgcccctatc      480
ttatcaacac ttccggaaac tactgttgtt                                      510

<210> SEQ ID NO 20
<211> LENGTH: 15
<212> TYPE: PRT
<213> ORGANISM: Artificial Sequence
<220> FEATURE:
<223> OTHER INFORMATION: HIV

<400> SEQUENCE: 20

Phe Lys Gln Ser Ser Gly Gly Asp Pro Glu Ile Val Thr His Ser
 1               5                  10                  15

<210> SEQ ID NO 21
<211> LENGTH: 14
<212> TYPE: PRT
<213> ORGANISM: Homo sapiens

<400> SEQUENCE: 21

Thr Ser Glu His Glu Leu Thr Cys Gln Ala Glu Gly Tyr Pro
 1               5                  10
```

<210> SEQ ID NO 22
<211> LENGTH: 23
<212> TYPE: PRT
<213> ORGANISM: Artificial Sequence
<220> FEATURE:
<223> OTHER INFORMATION: HBV

<400> SEQUENCE: 22

Ser Ser Thr Thr Ser Thr Gly Pro Cys Lys Thr Cys Thr Thr Pro Ala
1               5                   10                  15

Gln Gly Thr Ser Met Phe Pro
            20

<210> SEQ ID NO 23
<211> LENGTH: 225
<212> TYPE: PRT
<213> ORGANISM: Artificial Sequence
<220> FEATURE:
<223> OTHER INFORMATION: Recombinant protein RBHBcAg189-SEQ20

<400> SEQUENCE: 23

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Ser
            100                 105                 110

Gly Gly Gly Gly Ser Gln Asp Ala Ile Val Gln Gln Val Gln Ala Ser
        115                 120                 125

Val Gly Leu Arg Met Arg Gln Leu Met Trp Phe His Leu Ser Cys Leu
    130                 135                 140

Thr Phe Gly Gln Pro Thr Val Ile Glu Phe Leu Val Ser Phe Gly Thr
145                 150                 155                 160

Trp Ile Arg Thr Pro Gln Ala Tyr Arg Pro Asn Ala Pro Ile Leu
                165                 170                 175

Ser Thr Leu Pro Glu His Thr Ile Val Arg Arg Gly Gly Ser Arg
            180                 185                 190

Ala Thr Arg Ser Pro Arg Arg Thr Pro Ser Pro Arg Arg Arg
        195                 200                 205

Ser Gln Ser Pro Arg Arg Arg Ser Gln Ser Pro Ala Ser Ser Asn
    210                 215                 220

Cys
225

<210> SEQ ID NO 24
<211> LENGTH: 185
<212> TYPE: PRT
<213> ORGANISM: Artificial Sequence
<220> FEATURE:
<223> OTHER INFORMATION: Recombinant protein RBHBcAg149-SEQ20

<400> SEQUENCE: 24

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Leu Val Gly Lys Glu His Cys
        35                  40                  45

Ser Pro His His Thr Ala Leu Arg Ser Leu Leu Asn Cys Trp Gly Glu
    50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Phe Lys Gln Ser Ser Gly
                85                  90                  95

Gly Asp Pro Glu Ile Val Thr His Ser Glu Phe Gly Gly Gly Ser
            100                 105                 110

Gly Gly Gly Gly Ser Gln Asp Ala Ile Val Gln Gln Val Gln Ala Ser
            115                 120                 125

Val Gly Leu Arg Met Arg Gln Leu Met Trp Phe His Leu Ser Cys Leu
            130                 135                 140

Thr Phe Gly Gln Pro Thr Val Ile Glu Phe Leu Val Ser Phe Gly Thr
145                 150                 155                 160

Trp Ile Arg Thr Pro Gln Ala Tyr Arg Pro Pro Asn Ala Pro Ile Leu
                165                 170                 175

Ser Thr Leu Pro Glu His Thr Ile Val
            180                 185

<210> SEQ ID NO 25
<211> LENGTH: 224
<212> TYPE: PRT
<213> ORGANISM: Artificial Sequence
<220> FEATURE:
<223> OTHER INFORMATION: Recombinant protein TBHBcAg188-SEQ20

<400> SEQUENCE: 25

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Gly Thr Gly Ser Phe Lys Gln Ser
                85                  90                  95

Ser Gly Gly Asp Pro Glu Ile Val Thr His Ser Glu Phe Gly Gly Gly
            100                 105                 110

Gly Ser Gly Gly Gly Gly Ser Asp Ala Asp Ala Leu Leu Ala Gly Tyr
            115                 120                 125

Leu Arg Ser Lys Tyr Leu Lys His Ile Thr Lys Ala Ile Trp Tyr His
            130                 135                 140

Leu Ser Cys Leu Thr Phe Gly Lys Gln Thr Val His Glu Tyr Leu Val
145                 150                 155                 160

Ser Phe Gly Thr Trp Ile Arg Thr Pro Ala Ala Tyr Arg Pro Val Asn

```
                165                 170                 175
Ala Pro Ile Leu Thr Thr Leu Pro Glu Thr Ser Val Ile Arg Arg Arg
            180                 185                 190

Pro Ala Ser Arg Arg Ser Thr Pro Ser Pro Arg Arg Arg Arg Ser Gln
        195                 200                 205

Ser Pro Arg Arg Arg Arg Ser Pro Ser Pro Arg Pro Ala Ser Asn Cys
    210                 215                 220

<210> SEQ ID NO 26
<211> LENGTH: 189
<212> TYPE: PRT
<213> ORGANISM: Artificial Sequence
<220> FEATURE:
<223> OTHER INFORMATION: Recombinant protein TBHBcAg153-SEQ20

<400> SEQUENCE: 26

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Phe Lys Gln Ser
                85                  90                  95

Ser Gly Gly Asp Pro Glu Ile Val Thr His Ser Glu Phe Gly Gly Gly
            100                 105                 110

Gly Ser Gly Gly Gly Ser Asp Ala Asp Ala Leu Leu Ala Gly Tyr
        115                 120                 125

Leu Arg Ser Lys Tyr Leu Lys His Ile Thr Lys Ala Ile Trp Tyr His
    130                 135                 140

Leu Ser Cys Leu Thr Phe Gly Lys Gln Thr Val His Glu Tyr Leu Val
145                 150                 155                 160

Ser Phe Gly Thr Trp Ile Arg Thr Pro Ala Ala Tyr Arg Pro Val Asn
                165                 170                 175

Ala Pro Ile Leu Thr Thr Leu Pro Glu Thr Ser Val Ile
            180                 185

<210> SEQ ID NO 27
<211> LENGTH: 225
<212> TYPE: PRT
<213> ORGANISM: Artificial Sequence
<220> FEATURE:
<223> OTHER INFORMATION: Recombinant protein HBHBcAg189-SEQ20

<400> SEQUENCE: 27

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60
```

Thr Val Arg Leu Ile Thr Trp Val Arg Ala Thr Val Glu Gly Gly Gly
 65                  70                  75                  80

Gly Gly Ser Gly Gly Gly Thr Gly Ser Phe Lys Gln Ser Ser Gly
             85                  90                  95

Gly Asp Pro Glu Ile Val Thr His Ser Glu Phe Gly Gly Gly Ser
         100                 105                 110

Gly Gly Gly Gly Ser Gln Asp Ala Ile Ile Gly Tyr Val Gln Thr Thr
         115                 120                 125

Val Gly Leu Arg Met Arg Gln Gln Ile Trp Phe His Leu Ser Cys Leu
     130                 135                 140

Thr Phe Gly Gln Gln Thr Val Ile Glu Phe Leu Val Ser Phe Gly Thr
145                 150                 155                 160

Trp Met Arg Thr Pro Ala Ala Tyr Arg Pro Pro Asn Ala Pro Ile Leu
                 165                 170                 175

Ser Thr Leu Pro Glu His Thr Val Ile Arg Arg Gly Asn Pro Arg
             180                 185                 190

Ala Pro Arg Ser Pro Arg Arg Arg Thr Pro Ser Pro Arg Arg Arg
         195                 200                 205

Ser Gln Ser Pro Arg Arg Arg Ser Gln Ser Pro Ala Pro Ser Asn
     210                 215                 220

Cys
225

<210> SEQ ID NO 28
<211> LENGTH: 185
<212> TYPE: PRT
<213> ORGANISM: Artificial Sequence
<220> FEATURE:
<223> OTHER INFORMATION: Recombinant protein HBHBcAg149-SEQ20

<400> SEQUENCE: 28

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
             20                  25                  30

Thr Ser Val Ala Leu Tyr Glu Glu Asp Leu Val Gly Lys Glu His Cys
         35                  40                  45

Ser Pro His His Ala Ala Leu Arg Ala Leu Leu Asn Cys Trp Glu Glu
     50                  55                  60

Thr Val Arg Leu Ile Thr Trp Val Arg Ala Thr Val Glu Gly Gly Gly
 65                  70                  75                  80

Gly Gly Ser Gly Gly Gly Thr Gly Ser Phe Lys Gln Ser Ser Gly
             85                  90                  95

Gly Asp Pro Glu Ile Val Thr His Ser Glu Phe Gly Gly Gly Ser
         100                 105                 110

Gly Gly Gly Gly Ser Gln Asp Ala Ile Ile Gly Tyr Val Gln Thr Thr
         115                 120                 125

Val Gly Leu Arg Met Arg Gln Gln Ile Trp Phe His Leu Ser Cys Leu
     130                 135                 140

Thr Phe Gly Gln Gln Thr Val Ile Glu Phe Leu Val Ser Phe Gly Thr
145                 150                 155                 160

Trp Met Arg Thr Pro Ala Ala Tyr Arg Pro Pro Asn Ala Pro Ile Leu
                 165                 170                 175

Ser Thr Leu Pro Glu His Thr Val Ile
             180                 185

<210> SEQ ID NO 29
<211> LENGTH: 224
<212> TYPE: PRT
<213> ORGANISM: Artificial Sequence
<220> FEATURE:
<223> OTHER INFORMATION: Recombinant protein RBHBcAg189-SEQ21

<400> SEQUENCE: 29

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
                20                  25                  30

Thr Thr Thr Ala Leu Tyr Glu Glu Leu Val Gly Lys Glu His Cys
            35                  40                  45

Ser Pro His His Thr Ala Leu Arg Ser Leu Leu Asn Cys Trp Gly Glu
        50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Thr Ser Glu His Glu Leu
                85                  90                  95

Thr Cys Gln Ala Glu Gly Tyr Pro Glu Phe Gly Gly Gly Ser Gly
            100                 105                 110

Gly Gly Gly Ser Gln Asp Ala Ile Val Gln Gln Val Gln Ala Ser Val
        115                 120                 125

Gly Leu Arg Met Arg Gln Leu Met Trp Phe His Leu Ser Cys Leu Thr
    130                 135                 140

Phe Gly Gln Pro Thr Val Ile Glu Phe Leu Val Ser Phe Gly Thr Trp
145                 150                 155                 160

Ile Arg Thr Pro Gln Ala Tyr Arg Pro Asn Ala Pro Ile Leu Ser
                165                 170                 175

Thr Leu Pro Glu His Thr Ile Val Arg Arg Arg Gly Gly Ser Arg Ala
            180                 185                 190

Thr Arg Ser Pro Arg Arg Arg Thr Pro Ser Pro Arg Arg Arg Arg Ser
        195                 200                 205

Gln Ser Pro Arg Arg Arg Ser Gln Ser Pro Ala Ser Ser Asn Cys
    210                 215                 220
```

<210> SEQ ID NO 30
<211> LENGTH: 184
<212> TYPE: PRT
<213> ORGANISM: Artificial Sequence
<220> FEATURE:
<223> OTHER INFORMATION: Recombinant protein RBHBcAg149-SEQ21

<400> SEQUENCE: 30

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
                20                  25                  30

Thr Thr Thr Ala Leu Tyr Glu Glu Leu Val Gly Lys Glu His Cys
            35                  40                  45

Ser Pro His His Thr Ala Leu Arg Ser Leu Leu Asn Cys Trp Gly Glu
        50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Thr Ser Glu His Glu Leu
                85                  90                  95
```

Thr Cys Gln Ala Glu Gly Tyr Pro Glu Phe Gly Gly Gly Ser Gly
            100                 105                 110

Gly Gly Gly Ser Gln Asp Ala Ile Val Gln Val Gln Ala Ser Val
            115                 120                 125

Gly Leu Arg Met Arg Gln Leu Met Trp Phe His Leu Ser Cys Leu Thr
130                 135                 140

Phe Gly Gln Pro Thr Val Ile Glu Phe Leu Val Ser Phe Gly Thr Trp
145                 150                 155                 160

Ile Arg Thr Pro Gln Ala Tyr Arg Pro Pro Asn Ala Pro Ile Leu Ser
                165                 170                 175

Thr Leu Pro Glu His Thr Ile Val
            180

<210> SEQ ID NO 31
<211> LENGTH: 223
<212> TYPE: PRT
<213> ORGANISM: Artificial Sequence
<220> FEATURE:
<223> OTHER INFORMATION: Recombinant protein TBHBcAg188-SEQ21

<400> SEQUENCE: 31

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Thr Ser Glu His
                85                  90                  95

Glu Leu Thr Cys Gln Ala Glu Gly Tyr Pro Glu Phe Gly Gly Gly Gly
            100                 105                 110

Ser Gly Gly Gly Gly Ser Asp Ala Asp Ala Leu Leu Ala Gly Tyr Leu
        115                 120                 125

Arg Ser Lys Tyr Leu Lys His Ile Thr Lys Ala Ile Trp Tyr His Leu
    130                 135                 140

Ser Cys Leu Thr Phe Gly Lys Gln Thr Val His Glu Tyr Leu Val Ser
145                 150                 155                 160

Phe Gly Thr Trp Ile Arg Thr Pro Ala Ala Tyr Arg Pro Val Asn Ala
                165                 170                 175

Pro Ile Leu Thr Thr Leu Pro Glu Thr Ser Val Ile Arg Arg Arg Pro
            180                 185                 190

Ala Ser Arg Arg Ser Thr Pro Ser Pro Arg Arg Arg Ser Gln Ser
        195                 200                 205

Pro Arg Arg Arg Arg Ser Pro Ser Pro Arg Pro Ala Ser Asn Cys
    210                 215                 220

<210> SEQ ID NO 32
<211> LENGTH: 188
<212> TYPE: PRT
<213> ORGANISM: Artificial Sequence
<220> FEATURE:
<223> OTHER INFORMATION: Recombinant protein TBHBcAg153-SEQ21

```
<400> SEQUENCE: 32

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Pro Thr Leu Gln
            20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
        50                  55                  60

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Thr Ser Glu His
                85                  90                  95

Glu Leu Thr Cys Gln Ala Glu Gly Tyr Pro Glu Phe Gly Gly Gly
            100                 105                 110

Ser Gly Gly Gly Ser Asp Ala Asp Ala Leu Leu Ala Gly Tyr Leu
                115                 120                 125

Arg Ser Lys Tyr Leu Lys His Ile Thr Lys Ala Ile Trp Tyr His Leu
130                 135                 140

Ser Cys Leu Thr Phe Gly Lys Gln Thr Val His Glu Tyr Leu Val Ser
145                 150                 155                 160

Phe Gly Thr Trp Ile Arg Thr Pro Ala Ala Tyr Arg Pro Val Asn Ala
                165                 170                 175

Pro Ile Leu Thr Thr Leu Pro Glu Thr Ser Val Ile
                180                 185

<210> SEQ ID NO 33
<211> LENGTH: 224
<212> TYPE: PRT
<213> ORGANISM: Artificial Sequence
<220> FEATURE:
<223> OTHER INFORMATION: Recombinant protein HBHBcAg189-SEQ21

<400> SEQUENCE: 33

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
            35                  40                  45

Ser Pro His His Ala Ala Leu Arg Ala Leu Leu Asn Cys Trp Glu Glu
        50                  55                  60

Thr Val Arg Leu Ile Thr Trp Val Arg Ala Thr Val Glu Gly Gly Gly
65                  70                  75                  80

Gly Gly Ser Gly Gly Gly Thr Gly Ser Thr Ser Glu His Glu Leu
                85                  90                  95

Thr Cys Gln Ala Glu Gly Tyr Pro Glu Phe Gly Gly Gly Ser Gly
            100                 105                 110

Gly Gly Ser Gln Asp Ala Ile Ile Gly Tyr Val Gln Thr Thr Val
                115                 120                 125

Gly Leu Arg Met Arg Gln Gln Ile Trp Phe His Leu Ser Cys Leu Thr
130                 135                 140

Phe Gly Gln Gln Thr Val Ile Glu Phe Leu Val Ser Phe Gly Thr Trp
145                 150                 155                 160

Met Arg Thr Pro Ala Ala Tyr Arg Pro Pro Asn Ala Pro Ile Leu Ser
```

```
                        165                 170                 175

Thr Leu Pro Glu His Thr Val Ile Arg Arg Arg Gly Asn Pro Arg Ala
                180                 185                 190

Pro Arg Ser Pro Arg Arg Thr Pro Ser Pro Arg Arg Arg Arg Ser
        195                 200                 205

Gln Ser Pro Arg Arg Arg Ser Gln Ser Pro Ala Pro Ser Asn Cys
    210                 215                 220

<210> SEQ ID NO 34
<211> LENGTH: 184
<212> TYPE: PRT
<213> ORGANISM: Artificial Sequence
<220> FEATURE:
<223> OTHER INFORMATION: Recombinant protein HBHBcAg149-SEQ21

<400> SEQUENCE: 34

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Thr Gly Ser Thr Ser Glu His Glu Leu
                85                  90                  95

Thr Cys Gln Ala Glu Gly Tyr Pro Glu Phe Gly Gly Gly Gly Ser Gly
            100                 105                 110

Gly Gly Gly Ser Gln Asp Ala Ile Ile Gly Tyr Val Gln Thr Thr Val
        115                 120                 125

Gly Leu Arg Met Arg Gln Gln Ile Trp Phe His Leu Ser Cys Leu Thr
    130                 135                 140

Phe Gly Gln Gln Thr Val Ile Glu Phe Leu Val Ser Phe Gly Thr Trp
145                 150                 155                 160

Met Arg Thr Pro Ala Ala Tyr Arg Pro Asn Ala Pro Ile Leu Ser
                165                 170                 175

Thr Leu Pro Glu His Thr Val Ile
            180

<210> SEQ ID NO 35
<211> LENGTH: 233
<212> TYPE: PRT
<213> ORGANISM: Artificial Sequence
<220> FEATURE:
<223> OTHER INFORMATION: Recombinant protein RBHBcAg189-SEQ22

<400> SEQUENCE: 35

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Ser Leu Leu Asn Cys Trp Gly Glu
    50                  55                  60
```

```
Thr Val Arg Leu Ile Thr Trp Val Arg Asn Ser Val Glu Gly Gly Gly
 65                  70                  75                  80

Gly Gly Ser Gly Gly Gly Thr Gly Ser Ser Thr Thr Ser Thr
             85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Gln Asp Ala
            115                 120                 125

Ile Val Gln Gln Val Gln Ala Ser Val Gly Leu Arg Met Arg Gln Leu
            130                 135                 140

Met Trp Phe His Leu Ser Cys Leu Thr Phe Gly Gln Pro Thr Val Ile
145                 150                 155                 160

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190

Val Arg Arg Arg Gly Gly Ser Arg Ala Thr Arg Ser Pro Arg Arg Arg
            195                 200                 205

Thr Pro Ser Pro Arg Arg Arg Arg Ser Gln Ser Pro Arg Arg Arg Arg
210                 215                 220

Ser Gln Ser Pro Ala Ser Ser Asn Cys
225                 230

<210> SEQ ID NO 36
<211> LENGTH: 193
<212> TYPE: PRT
<213> ORGANISM: Artificial Sequence
<220> FEATURE:
<223> OTHER INFORMATION: Recombinant protein RBHBcAg149-SEQ22

<400> SEQUENCE: 36

Met Asp Ile Asp Pro Tyr Lys Glu Phe Gly Ala Ser Ser Gln Leu Ile
  1               5                  10                  15

Ser Phe Leu Pro Glu Asp Phe Phe Pro Asn Leu Ala Glu Leu Val Glu
             20                  25                  30

Thr Thr Thr Ala Leu Tyr Glu Glu Glu Leu Val Gly Lys Glu His Cys
         35                  40                  45

Ser Pro His His Thr Ala Leu Arg Ser Leu Leu Asn Cys Trp Gly Glu
 50                  55                  60

Thr Val Arg Leu Ile Thr Trp Val Arg Asn Ser Val Glu Gly Gly Gly
 65                  70                  75                  80

Gly Gly Ser Gly Gly Gly Thr Gly Ser Ser Thr Thr Ser Thr
             85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Gln Asp Ala
            115                 120                 125

Ile Val Gln Gln Val Gln Ala Ser Val Gly Leu Arg Met Arg Gln Leu
            130                 135                 140

Met Trp Phe His Leu Ser Cys Leu Thr Phe Gly Gln Pro Thr Val Ile
145                 150                 155                 160

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190
```

Val

<210> SEQ ID NO 37
<211> LENGTH: 232
<212> TYPE: PRT
<213> ORGANISM: Artificial Sequence
<220> FEATURE:
<223> OTHER INFORMATION: Recombinant protein TBHBcAg188-SEQ22

<400> SEQUENCE: 37

```
Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
        50                  55                  60

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Ser Ser Thr Thr
                85                  90                  95

Ser Thr Gly Pro Cys Lys Thr Cys Thr Thr Pro Ala Gln Gly Thr Ser
                100                 105                 110

Met Phe Pro Glu Phe Gly Gly Gly Ser Gly Gly Gly Ser Asp
            115                 120                 125

Ala Asp Ala Leu Leu Ala Gly Tyr Leu Arg Ser Lys Tyr Leu Lys His
        130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Leu Pro
            180                 185                 190

Glu Thr Ser Val Ile Arg Arg Arg Pro Ala Ser Arg Arg Ser Thr Pro
        195                 200                 205

Ser Pro Arg Arg Arg Ser Gln Ser Pro Arg Arg Arg Ser Pro
210                 215                 220

Ser Pro Arg Pro Ala Ser Asn Cys
225                 230
```

<210> SEQ ID NO 38
<211> LENGTH: 197
<212> TYPE: PRT
<213> ORGANISM: Artificial Sequence
<220> FEATURE:
<223> OTHER INFORMATION: Recombinant protein TBHBcAg153-SEQ22

<400> SEQUENCE: 38

```
Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
        50                  55                  60
```

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Ser Ser Thr Thr
                85                  90                  95

Ser Thr Gly Pro Cys Lys Thr Cys Thr Thr Pro Ala Gln Gly Thr Ser
            100                 105                 110

Met Phe Pro Glu Phe Gly Gly Gly Ser Gly Gly Gly Gly Ser Asp
        115                 120                 125

Ala Asp Ala Leu Leu Ala Gly Tyr Leu Arg Ser Lys Tyr Leu Lys His
        130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
        195

<210> SEQ ID NO 39
<211> LENGTH: 233
<212> TYPE: PRT
<213> ORGANISM: Artificial Sequence
<220> FEATURE:
<223> OTHER INFORMATION: Recombinant protein HBHBcAg189-SEQ22

<400> SEQUENCE: 39

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Thr Gly Ser Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Ser Gly Gly Gly Gly Ser Gln Asp Ala
        115                 120                 125

Ile Ile Gly Tyr Val Gln Thr Thr Val Gly Leu Arg Met Arg Gln Gln
        130                 135                 140

Ile Trp Phe His Leu Ser Cys Leu Thr Phe Gly Gln Gln Thr Val Ile
145                 150                 155                 160

Glu Phe Leu Val Ser Phe Gly Thr Trp Met Arg Thr Pro Ala Ala Tyr
                165                 170                 175

Arg Pro Pro Asn Ala Pro Ile Leu Ser Thr Leu Pro Glu His Thr Val
            180                 185                 190

Ile Arg Arg Arg Gly Asn Pro Arg Ala Pro Arg Ser Pro Arg Arg Arg
        195                 200                 205

Thr Pro Ser Pro Arg Arg Arg Ser Gln Ser Pro Arg Arg Arg Arg
    210                 215                 220

Ser Gln Ser Pro Ala Pro Ser Asn Cys
225                 230

<210> SEQ ID NO 40
<211> LENGTH: 193
<212> TYPE: PRT
<213> ORGANISM: Artificial Sequence
<220> FEATURE:
<223> OTHER INFORMATION: Recombinant protein HBHBcAg149-SEQ22

<400> SEQUENCE: 40

Met Asp Ile Asp Pro Tyr Lys Glu Phe Gly Ala Ser Ser Gln Leu Val
1               5                   10                  15

Ser Phe Leu Pro Ala Asp Phe Phe Pro Ala Leu Asn Asp Leu Val Glu
            20                  25                  30

Thr Ser Val Ala Leu Tyr Glu Glu Asp Leu Val Gly Lys Glu His Cys
        35                  40                  45

Ser Pro His His Ala Ala Leu Arg Ala Leu Leu Asn Cys Trp Glu Glu
    50                  55                  60

Thr Val Arg Leu Ile Thr Trp Val Arg Ala Thr Val Glu Gly Gly Gly
65                  70                  75                  80

Gly Gly Ser Gly Gly Gly Thr Gly Ser Ser Ser Thr Thr Ser Thr Thr
                85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Gly Ser Gln Asp Ala
            115                 120                 125

Ile Ile Gly Tyr Val Gln Thr Thr Val Gly Leu Arg Met Arg Gln Gln
    130                 135                 140

Ile Trp Phe His Leu Ser Cys Leu Thr Phe Gly Gln Gln Thr Val Ile
145                 150                 155                 160

Glu Phe Leu Val Ser Phe Gly Thr Trp Met Arg Thr Pro Ala Ala Tyr
                165                 170                 175

Arg Pro Pro Asn Ala Pro Ile Leu Ser Thr Leu Pro Glu His Thr Val
            180                 185                 190

Ile

<210> SEQ ID NO 41
<211> LENGTH: 227
<212> TYPE: PRT
<213> ORGANISM: Artificial Sequence
<220> FEATURE:
<223> OTHER INFORMATION: Recombinant protein HBcAg183-SEQ22

<400> SEQUENCE: 41

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Thr Gly Ser Ser Ser Thr Thr Ser Thr Thr
                85                  90                  95

```
Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Arg Glu Leu
            115                 120                 125

Val Val Ser Tyr Val Asn Val Asn Met Gly Leu Lys Ile Arg Gln Leu
            130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Pro Ala Tyr
                165                 170                 175

Arg Pro Gln Asn Ala Pro Ile Leu Ser Thr Leu Pro Glu Thr Thr Val
            180                 185                 190

Val Arg Arg Arg Gly Arg Ser Pro Arg Arg Arg Thr Pro Ser Pro Arg
            195                 200                 205

Arg Arg Arg Ser Gln Ser Pro Arg Arg Arg Arg Ser Gln Ser Arg Glu
            210                 215                 220

Ser Gln Cys
225

<210> SEQ ID NO 42
<211> LENGTH: 193
<212> TYPE: PRT
<213> ORGANISM: Artificial Sequence
<220> FEATURE:
<223> OTHER INFORMATION: Recombinant protein HBcAg149-SEQ22

<400> SEQUENCE: 42

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Gly Gly
65                  70                  75                  80

Gly Gly Ser Gly Gly Gly Gly Thr Gly Ser Ser Ser Thr Thr Ser Thr
                85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Arg Glu Leu
            115                 120                 125

Val Val Ser Tyr Val Asn Val Asn Met Gly Leu Lys Ile Arg Gln Leu
            130                 135                 140

Leu Trp Phe His Ile Ser Cys Leu Thr Phe Gly Arg Glu Thr Val Leu
145                 150                 155                 160

Glu Tyr Leu Val Ser Phe Gly Val Trp Ile Arg Thr Pro Pro Ala Tyr
                165                 170                 175

Arg Pro Gln Asn Ala Pro Ile Leu Ser Thr Leu Pro Glu Thr Thr Val
            180                 185                 190

Val

<210> SEQ ID NO 43
<211> LENGTH: 25
<212> TYPE: PRT
```

<213> ORGANISM: Artificial Sequence
<220> FEATURE:
<223> OTHER INFORMATION: linker

<400> SEQUENCE: 43

Gly Gly Gly Gly Ser Gly Gly Gly Thr Gly Ser Glu Phe Gly
1               5                   10                  15

Gly Gly Gly Ser Gly Gly Gly Ser
            20                  25

<210> SEQ ID NO 44
<211> LENGTH: 226
<212> TYPE: PRT
<213> ORGANISM: Artificial Sequence
<220> FEATURE:
<223> OTHER INFORMATION: HBV

<400> SEQUENCE: 44

Met Glu Asn Ile Ala Ser Gly Leu Leu Gly Pro Leu Leu Val Leu Gln
1               5                   10                  15

Ala Gly Phe Phe Leu Leu Thr Lys Ile Leu Thr Ile Pro Gln Ser Leu
            20                  25                  30

Asp Ser Trp Trp Thr Ser Leu Asn Phe Leu Gly Gly Thr Pro Val Cys
        35                  40                  45

Leu Gly Gln Asn Ser Gln Ser Gln Ile Ser Ser His Ser Pro Thr Cys
    50                  55                  60

Cys Pro Pro Ile Cys Pro Gly Tyr Arg Trp Met Cys Leu Arg Arg Phe
65                  70                  75                  80

Ile Ile Phe Leu Cys Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Lys Thr Cys Thr Thr Pro Ala
        115                 120                 125

Gln Gly Thr Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Phe Trp Gly Pro Ser Leu Tyr Asn Ile
        195                 200                 205

Leu Ser Pro Phe Met Pro Leu Leu Pro Ile Phe Phe Cys Leu Trp Val
    210                 215                 220

Tyr Ile
225

<210> SEQ ID NO 45
<211> LENGTH: 47
<212> TYPE: DNA
<213> ORGANISM: Artificial Sequence
<220> FEATURE:
<223> OTHER INFORMATION: primer

<400> SEQUENCE: 45
actttaagaa ggagatatac atatgatgga cattgatcct tataaag         47

<210> SEQ ID NO 46
<211> LENGTH: 56
<212> TYPE: DNA
<213> ORGANISM: Artificial Sequence
<220> FEATURE:
<223> OTHER INFORMATION: primer

<400> SEQUENCE: 46
gtggtgctcg aggcggccgc aagcttttaa acgattgtat gctccggaag agtcga      56

<210> SEQ ID NO 47
<211> LENGTH: 67
<212> TYPE: DNA
<213> ORGANISM: Artificial Sequence
<220> FEATURE:
<223> OTHER INFORMATION: primer

<400> SEQUENCE: 47
gtggtgctcg aggcggccgc aagcttttag cagttggagg aagctggaga ctgagatctg    60
cggcgac                                                              67

<210> SEQ ID NO 48
<211> LENGTH: 47
<212> TYPE: DNA
<213> ORGANISM: Artificial Sequence
<220> FEATURE:
<223> OTHER INFORMATION: primer

<400> SEQUENCE: 48
actttaagaa ggagatatac atatgatgga aaaccttgaa agacttg                  47

<210> SEQ ID NO 49
<211> LENGTH: 54
<212> TYPE: DNA
<213> ORGANISM: Artificial Sequence
<220> FEATURE:
<223> OTHER INFORMATION: primer

<400> SEQUENCE: 49
gtggtgctcg aggcggccgc aagcttttag ataactgaag tttccggaag agtg          54

<210> SEQ ID NO 50
<211> LENGTH: 49
<212> TYPE: DNA
<213> ORGANISM: Artificial Sequence
<220> FEATURE:
<223> OTHER INFORMATION: primer

<400> SEQUENCE: 50
gtggtgctcg aggcggccgc aagcttttag caattgcttg ctggtcttg                49

<210> SEQ ID NO 51
<211> LENGTH: 47
<212> TYPE: DNA
<213> ORGANISM: Artificial Sequence
<220> FEATURE:
<223> OTHER INFORMATION: primer

<400> SEQUENCE: 51
actttaagaa ggagatatac atatgatgga cattgatcct tataaag                  47

<210> SEQ ID NO 52
<211> LENGTH: 56
<212> TYPE: DNA
<213> ORGANISM: Artificial Sequence -continued

```
<220> FEATURE:
<223> OTHER INFORMATION: primer

<400> SEQUENCE: 52
gtggtgctcg aggcggccgc aagcttttaa atgactgtgt gctctggaag agttga        56

<210> SEQ ID NO 53
<211> LENGTH: 67
<212> TYPE: DNA
<213> ORGANISM: Artificial Sequence
<220> FEATURE:
<223> OTHER INFORMATION: primer

<400> SEQUENCE: 53
gtggtgctcg aggcggccgc aagcttttag cagttggagg gagctggaga ttgagatctc    60
cggcgac                                                              67

<210> SEQ ID NO 54
<211> LENGTH: 48
<212> TYPE: DNA
<213> ORGANISM: Artificial Sequence
<220> FEATURE:
<223> OTHER INFORMATION: primer

<400> SEQUENCE: 54
gatccacctc tgaacatgaa ctgacatgtc aggctgaggg ctaccccg                 48

<210> SEQ ID NO 55
<211> LENGTH: 48
<212> TYPE: DNA
<213> ORGANISM: Artificial Sequence
<220> FEATURE:
<223> OTHER INFORMATION: primer

<400> SEQUENCE: 55
aattcggggt agccctcagc ctgacatgtc agttcatgtt cagaggtg                 48

<210> SEQ ID NO 56
<211> LENGTH: 51
<212> TYPE: DNA
<213> ORGANISM: Artificial Sequence
<220> FEATURE:
<223> OTHER INFORMATION: primer

<400> SEQUENCE: 56
gatccttcaa acagtcttct ggtggtgacc cggaaatcgt tacccactct g             51

<210> SEQ ID NO 57
<211> LENGTH: 51
<212> TYPE: DNA
<213> ORGANISM: Artificial Sequence
<220> FEATURE:
<223> OTHER INFORMATION: primer

<400> SEQUENCE: 57
aattcagagt gggtaacgat ttccgggtca ccaccagaag actgtttgaa g             51

<210> SEQ ID NO 58
<211> LENGTH: 75
<212> TYPE: DNA
<213> ORGANISM: Artificial Sequence
<220> FEATURE:
<223> OTHER INFORMATION: primer

<400> SEQUENCE: 58
```

```
gatcctcatc aacaaccagc accggaccat gcaaaacctg cacaactcct gctcaaggaa    60
cctctatgtt tcccg                                                    75
```

<210> SEQ ID NO 59
<211> LENGTH: 75
<212> TYPE: DNA
<213> ORGANISM: Artificial Sequence
<220> FEATURE:
<223> OTHER INFORMATION: primer

<400> SEQUENCE: 59

```
aattcgggaa acatagaggt tccttgagca ggagttgtgc aggttttgca tggtccggtg    60
ctggttgttg atgag                                                    75
```

<210> SEQ ID NO 60
<211> LENGTH: 23
<212> TYPE: PRT
<213> ORGANISM: Artificial Sequence
<220> FEATURE:
<223> OTHER INFORMATION: HBV

<400> SEQUENCE: 60

Ser Thr Thr Thr Ser Thr Gly Pro Cys Lys Thr Cys Thr Thr Pro Ala
1               5                   10                  15

Gln Gly Asn Ser Met Phe Pro
            20

<210> SEQ ID NO 61
<211> LENGTH: 23
<212> TYPE: PRT
<213> ORGANISM: Artificial Sequence
<220> FEATURE:
<223> OTHER INFORMATION: HBV

<400> SEQUENCE: 61

Thr Ser Thr Thr Ser Thr Gly Pro Cys Lys Thr Cys Thr Ile Pro Ala
1               5                   10                  15

Gln Gly Thr Ser Met Phe Pro
            20

<210> SEQ ID NO 62
<211> LENGTH: 23
<212> TYPE: PRT
<213> ORGANISM: Artificial Sequence
<220> FEATURE:
<223> OTHER INFORMATION: HBV

<400> SEQUENCE: 62

Ser Ser Thr Thr Ser Thr Gly Pro Cys Arg Thr Cys Thr Thr Pro Ala
1               5                   10                  15

Gln Gly Thr Ser Met Tyr Pro
            20

<210> SEQ ID NO 63
<211> LENGTH: 75
<212> TYPE: DNA
<213> ORGANISM: Artificial Sequence
<220> FEATURE:
<223> OTHER INFORMATION: primer

<400> SEQUENCE: 63

```
gatcctctac caccacctct accggtccgt gcaaaacctg caccaccccg gctcagggta    60
actctatgtt cccgg                                                    75
```

<210> SEQ ID NO 64
<211> LENGTH: 75
<212> TYPE: DNA
<213> ORGANISM: Artificial Sequence
<220> FEATURE:
<223> OTHER INFORMATION: primer

<400> SEQUENCE: 64
aattccggga acatagagtt accctgagcc ggggtggtgc aggttttgca cggaccggta    60
gaggtggtgg tagag    75

<210> SEQ ID NO 65
<211> LENGTH: 75
<212> TYPE: DNA
<213> ORGANISM: Artificial Sequence
<220> FEATURE:
<223> OTHER INFORMATION: primer

<400> SEQUENCE: 65
gatccacctc taccacctct accggtccgt gcaaaacctg caccatcccg gctcagggta    60
cctctatgtt cccgg    75

<210> SEQ ID NO 66
<211> LENGTH: 75
<212> TYPE: DNA
<213> ORGANISM: Artificial Sequence
<220> FEATURE:
<223> OTHER INFORMATION: primer

<400> SEQUENCE: 66
aattccggga acatagaggt accctgagcc gggatggtgc aggttttgca cggaccggta    60
gaggtggtag aggtg    75

<210> SEQ ID NO 67
<211> LENGTH: 75
<212> TYPE: DNA
<213> ORGANISM: Artificial Sequence
<220> FEATURE:
<223> OTHER INFORMATION: primer

<400> SEQUENCE: 67
gatcctcttc taccacctct accggtccgt gccgtacctg caccaccccg gctcagggta    60
cctctatgta cccgg    75

<210> SEQ ID NO 68
<211> LENGTH: 75
<212> TYPE: DNA
<213> ORGANISM: Artificial Sequence
<220> FEATURE:
<223> OTHER INFORMATION: primer

<400> SEQUENCE: 68
aattccgggt acatagaggt accctgagcc ggggtggtgc aggtacggca cggaccggta    60
gaggtggtag aagag    75

<210> SEQ ID NO 69
<211> LENGTH: 193
<212> TYPE: PRT
<213> ORGANISM: Artificial Sequence
<220> FEATURE:
<223> OTHER INFORMATION: Recombinant protein RBHBcAg149-SEQ60

<400> SEQUENCE: 69

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Leu Val Gly Lys Glu His Cys
            35                  40                  45

Ser Pro His His Thr Ala Leu Arg Ser Leu Leu Asn Cys Trp Gly Glu
        50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Ser Thr Thr Thr Ser Thr
                85                  90                  95

Gly Pro Cys Lys Thr Cys Thr Thr Pro Ala Gln Gly Asn Ser Met Phe
            100                 105                 110

Pro Glu Phe Gly Gly Gly Gly Ser Gly Gly Gly Gly Ser Gln Asp Ala
            115                 120                 125

Ile Val Gln Gln Val Gln Ala Ser Val Gly Leu Arg Met Arg Gln Leu
        130                 135                 140

Met Trp Phe His Leu Ser Cys Leu Thr Phe Gly Gln Pro Thr Val Ile
145                 150                 155                 160

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190

Val
```

<210> SEQ ID NO 70
<211> LENGTH: 193
<212> TYPE: PRT
<213> ORGANISM: Artificial Sequence
<220> FEATURE:
<223> OTHER INFORMATION: Recombinant protein RBHBcAg149-SEQ61

<400> SEQUENCE: 70

```
Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
            20                  25                  30

Thr Thr Thr Ala Leu Tyr Glu Glu Leu Val Gly Lys Glu His Cys
            35                  40                  45

Ser Pro His His Thr Ala Leu Arg Ser Leu Leu Asn Cys Trp Gly Glu
        50                  55                  60

Thr Val Arg Leu Ile Thr Trp Val Arg Asn Ser Val Glu Gly Gly Gly
65                  70                  75                  80

Gly Gly Ser Gly Gly Gly Gly Thr Gly Ser Thr Ser Thr Thr Ser Thr
                85                  90                  95

Gly Pro Cys Lys Thr Cys Thr Ile Pro Ala Gln Gly Thr Ser Met Phe
            100                 105                 110

Pro Glu Phe Gly Gly Gly Gly Ser Gly Gly Gly Gly Ser Gln Asp Ala
            115                 120                 125

Ile Val Gln Gln Val Gln Ala Ser Val Gly Leu Arg Met Arg Gln Leu
        130                 135                 140

Met Trp Phe His Leu Ser Cys Leu Thr Phe Gly Gln Pro Thr Val Ile
145                 150                 155                 160
```

-continued

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190

Val

<210> SEQ ID NO 71
<211> LENGTH: 193
<212> TYPE: PRT
<213> ORGANISM: Artificial Sequence
<220> FEATURE:
<223> OTHER INFORMATION: Recombinant protein RBHBcAg149-SEQ62

<400> SEQUENCE: 71

Met Asp Ile Asp Pro Tyr Lys Glu Phe Gly Ala Ser Ser Gln Leu Ile
1               5                   10                  15

Ser Phe Leu Pro Glu Asp Phe Phe Pro Asn Leu Ala Glu Leu Val Glu
                20                  25                  30

Thr Thr Thr Ala Leu Tyr Glu Glu Leu Val Gly Lys Glu His Cys
            35                  40                  45

Ser Pro His His Thr Ala Leu Arg Ser Leu Leu Asn Cys Trp Gly Glu
        50                  55                  60

Thr Val Arg Leu Ile Thr Trp Val Arg Asn Ser Val Glu Gly Gly Gly
65                  70                  75                  80

Gly Gly Ser Gly Gly Gly Thr Gly Ser Ser Ser Thr Thr Ser Thr
                85                  90                  95

Gly Pro Cys Arg Thr Cys Thr Thr Pro Ala Gln Gly Thr Ser Met Tyr
            100                 105                 110

Pro Glu Phe Gly Gly Gly Gly Ser Gly Gly Gly Gly Ser Gln Asp Ala
        115                 120                 125

Ile Val Gln Gln Val Gln Ala Ser Val Gly Leu Arg Met Arg Gln Leu
    130                 135                 140

Met Trp Phe His Leu Ser Cys Leu Thr Phe Gly Gln Pro Thr Val Ile
145                 150                 155                 160

Glu Phe Leu Val Ser Phe Gly Thr Trp Ile Arg Thr Pro Gln Ala Tyr
                165                 170                 175

Arg Pro Pro Asn Ala Pro Ile Leu Ser Thr Leu Pro Glu His Thr Ile
            180                 185                 190

Val

<210> SEQ ID NO 72
<211> LENGTH: 197
<212> TYPE: PRT
<213> ORGANISM: Artificial Sequence
<220> FEATURE:
<223> OTHER INFORMATION: Recombinant protein TBHBcAg153-SEQ60

<400> SEQUENCE: 72

Met Glu Asn Leu Glu Arg Leu Asp Ile Tyr Lys Glu Phe Gly Val Ser
1               5                   10                  15

Asp Val Leu Val Ser Phe Leu Pro Asp Asp Phe Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
        50                  55                  60

```
Cys Gly Val Glu Leu Arg Asp Phe Ile Asp Trp Met His Glu Gln Gly
 65                  70                  75                  80

Gly Gly Gly Gly Ser Gly Gly Gly Thr Gly Ser Ser Thr Thr Thr
                 85                  90                  95

Ser Thr Gly Pro Cys Lys Thr Cys Thr Thr Pro Ala Gln Gly Asn Ser
            100                 105                 110

Met Phe Pro Glu Phe Gly Gly Gly Ser Gly Gly Gly Gly Ser Asp
            115                 120                 125

Ala Asp Ala Leu Leu Ala Gly Tyr Leu Arg Ser Lys Tyr Leu Lys His
            130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
            195

<210> SEQ ID NO 73
<211> LENGTH: 197
<212> TYPE: PRT
<213> ORGANISM: Artificial Sequence
<220> FEATURE:
<223> OTHER INFORMATION: Recombinant protein TBHBcAg153-SEQ61

<400> SEQUENCE: 73

Met Glu Asn Leu Glu Arg Leu Asp Ile Tyr Lys Glu Phe Gly Val Ser
 1               5                  10                  15

Asp Val Leu Val Ser Phe Leu Pro Asp Asp Phe Phe Pro Thr Leu Gln
                 20                  25                  30

Gln Leu Leu Glu Ser Val Asn Ala Leu Tyr Glu Asp Glu Leu Thr Gly
             35                  40                  45

Pro Asn His Cys Ser Pro His His Thr Ala Leu Arg His Leu Ile Met
     50                  55                  60

Cys Gly Val Glu Leu Arg Asp Phe Ile Asp Trp Met His Glu Gln Gly
 65                  70                  75                  80

Gly Gly Gly Gly Ser Gly Gly Gly Thr Gly Ser Thr Ser Thr Thr
                 85                  90                  95

Ser Thr Gly Pro Cys Lys Thr Cys Thr Ile Pro Ala Gln Gly Thr Ser
            100                 105                 110

Met Phe Pro Glu Phe Gly Gly Gly Ser Gly Gly Gly Gly Ser Asp
            115                 120                 125

Ala Asp Ala Leu Leu Ala Gly Tyr Leu Arg Ser Lys Tyr Leu Lys His
            130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
            195

<210> SEQ ID NO 74
<211> LENGTH: 197
```

```
<212> TYPE: PRT
<213> ORGANISM: Artificial Sequence
<220> FEATURE:
<223> OTHER INFORMATION: Recombinant protein TBHBcAg153-SEQ62

<400> SEQUENCE: 74

Met Glu Asn Leu Glu Arg Leu Asp Ile Tyr Lys Glu Phe Gly Val Ser
1               5                   10                  15

Asp Val Leu Val Ser Phe Leu Pro Asp Phe Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg His Leu Ile Met
    50                  55                  60

Cys Gly Val Glu Leu Arg Asp Phe Ile Asp Trp Met His Glu Gln Gly
65                  70                  75                  80

Gly Gly Gly Gly Ser Gly Gly Gly Thr Gly Ser Ser Ser Thr Thr
                85                  90                  95

Ser Thr Gly Pro Cys Arg Thr Cys Thr Thr Pro Ala Gln Gly Thr Ser
                100                 105                 110

Met Tyr Pro Glu Phe Gly Gly Gly Ser Gly Gly Gly Ser Asp
            115                 120                 125

Ala Asp Ala Leu Leu Ala Gly Tyr Leu Arg Ser Lys Tyr Leu Lys His
    130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Thr Trp Ile Arg Thr
                165                 170                 175

Pro Ala Ala Tyr Arg Pro Val Asn Ala Pro Ile Leu Thr Thr Leu Pro
            180                 185                 190

Glu Thr Ser Val Ile
            195

<210> SEQ ID NO 75
<211> LENGTH: 210
<212> TYPE: PRT
<213> ORGANISM: Artificial Sequence
<220> FEATURE:
<223> OTHER INFORMATION: RBHBcAg189-T3 carrier

<400> SEQUENCE: 75

Met Asp Ile Asp Pro Tyr Lys Glu Phe Gly Ala Ser Ser Gln Leu Ile
1               5                   10                  15

Ser Phe Leu Pro Ser Asp Phe Phe Pro Ser Val Ala Glu Leu Val Glu
                20                  25                  30

Thr Thr Thr Ala Leu Tyr Glu Glu Leu Val Gly Lys Glu His Cys
            35                  40                  45

Ser Pro His His Thr Ala Leu Arg Gln Ala Ile Leu Cys Trp Gly Glu
    50                  55                  60

Leu Met Thr Leu Ala Thr Trp Val Arg Asn Ser Val Glu Gly Gly Gly
65                  70                  75                  80

Gly Gly Ser Gly Gly Gly Gly Thr Gly Ser Glu Phe Gly Gly Gly
                85                  90                  95

Ser Gly Gly Gly Gly Ser Gln Asp Ala Ile Val Gln Val Gln Ala
            100                 105                 110

Ser Val Gly Leu Arg Met Arg Gln Leu Met Trp Phe His Leu Ser Cys
115                 120                 125
```

```
Leu Thr Phe Gly Gln Pro Thr Val Ile Glu Phe Leu Val Ser Phe Gly
            130                 135                 140

Val Trp Ile Arg Thr Pro Pro Ala Tyr Arg Pro Pro Asn Ala Pro Ile
145                 150                 155                 160

Leu Ser Thr Leu Pro Glu His Thr Val Ile Arg Arg Arg Gly Gly Ser
                165                 170                 175

Arg Ala Thr Arg Ser Pro Arg Arg Arg Thr Pro Ser Pro Arg Arg Arg
            180                 185                 190

Arg Ser Gln Ser Pro Arg Arg Arg Ser Gln Ser Pro Ala Ser Ser
            195                 200                 205

Asn Cys
    210

<210> SEQ ID NO 76
<211> LENGTH: 209
<212> TYPE: PRT
<213> ORGANISM: Artificial Sequence
<220> FEATURE:
<223> OTHER INFORMATION: TBHBcAg188-T3 carrier

<400> SEQUENCE: 76

Met Glu Asn Leu Glu Arg Leu Asp Ile Tyr Lys Glu Phe Gly Val Ser
1               5                   10                  15

Asp Phe Leu Pro Ser Asp Phe Pro Ser Val Phe Pro Thr Leu Gln
            20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg Gln Ala Ile Leu
50                  55                  60

Cys Trp Gly Glu Leu Arg Asp Phe Ile Asp Trp Met His Glu Gln Gly
65                  70                  75                  80

Gly Gly Gly Gly Ser Gly Gly Gly Thr Gly Ser Glu Phe Gly Gly
            85                  90                  95

Gly Gly Ser Gly Gly Gly Gly Ser Asp Ala Asp Ala Leu Leu Ala Gly
            100                 105                 110

Tyr Leu Arg Ser Lys Tyr Leu Lys His Ile Thr Lys Ala Ile Trp Tyr
            115                 120                 125

His Leu Ser Cys Leu Thr Phe Gly Lys Gln Thr Val His Glu Tyr Leu
            130                 135                 140

Val Ser Phe Gly Val Trp Ile Arg Thr Pro Pro Ala Tyr Arg Pro Pro
145                 150                 155                 160

Asn Ala Pro Ile Leu Thr Thr Leu Pro Glu Thr Ser Val Ile Arg Arg
                165                 170                 175

Arg Pro Ala Ser Arg Arg Ser Thr Pro Ser Pro Arg Arg Arg Arg Ser
            180                 185                 190

Gln Ser Pro Arg Arg Arg Arg Ser Pro Ser Pro Arg Pro Ala Ser Asn
            195                 200                 205

Cys

<210> SEQ ID NO 77
<211> LENGTH: 210
<212> TYPE: PRT
<213> ORGANISM: Artificial Sequence
<220> FEATURE:
<223> OTHER INFORMATION: HBHBcAg189-T3 carrier

<400> SEQUENCE: 77
```

```
Met Asp Ile Asp Pro Tyr Lys Glu Phe Gly Ala Ser Ser Gln Leu Val
1               5                   10                  15

Ser Phe Leu Pro Ser Asp Phe Phe Pro Ser Val Asn Asp Leu Val Glu
            20                  25                  30

Thr Ser Val Ala Leu Tyr Glu Glu Asp Leu Val Gly Lys Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Arg Ala Thr Val Glu Gly Gly Gly
65                  70                  75                  80

Gly Gly Ser Gly Gly Gly Thr Gly Ser Gly Phe Gly Gly Gly
                85                  90                  95

Ser Gly Gly Gly Ser Gln Asp Ala Ile Ile Gly Tyr Val Gln Thr
            100                 105                 110

Thr Val Gly Leu Arg Met Arg Gln Gln Ile Trp Phe His Leu Ser Cys
        115                 120                 125

Leu Thr Phe Gly Gln Gln Thr Val Ile Glu Phe Leu Val Ser Phe Gly
    130                 135                 140

Val Trp Ile Arg Thr Pro Pro Ala Tyr Arg Pro Pro Asn Ala Pro Ile
145                 150                 155                 160

Leu Ser Thr Leu Pro Glu His Thr Val Ile Arg Arg Arg Gly Asn Pro
                165                 170                 175

Arg Ala Pro Arg Ser Pro Arg Arg Arg Thr Pro Ser Pro Arg Arg Arg
            180                 185                 190

Arg Ser Gln Ser Pro Arg Arg Arg Ser Gln Ser Pro Ala Pro Ser
            195                 200                 205

Asn Cys
    210

<210> SEQ ID NO 78
<211> LENGTH: 170
<212> TYPE: PRT
<213> ORGANISM: Artificial Sequence
<220> FEATURE:
<223> OTHER INFORMATION: RBHBcAg149-T3 carrier

<400> SEQUENCE: 78

Met Asp Ile Asp Pro Tyr Lys Glu Phe Gly Ala Ser Ser Gln Leu Ile
1               5                   10                  15

Ser Phe Leu Pro Ser Asp Phe Phe Pro Ser Val Ala Glu Leu Val Glu
            20                  25                  30

Thr Thr Thr Ala Leu Tyr Glu Glu Leu Val Gly Lys Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Arg Asn Ser Val Glu Gly Gly Gly
65                  70                  75                  80

Gly Gly Ser Gly Gly Gly Thr Gly Ser Glu Phe Gly Gly Gly
                85                  90                  95

Ser Gly Gly Gly Ser Gln Asp Ala Ile Val Gln Val Gln Ala
            100                 105                 110

Ser Val Gly Leu Arg Met Arg Gln Leu Met Trp Phe His Leu Ser Cys
        115                 120                 125

Leu Thr Phe Gly Gln Pro Thr Val Ile Glu Phe Leu Val Ser Phe Gly
    130                 135                 140
```

```
Val Trp Ile Arg Thr Pro Pro Ala Tyr Arg Pro Pro Asn Ala Pro Ile
145                 150                 155                 160

Leu Ser Thr Leu Pro Glu His Thr Val Ile
                165                 170

<210> SEQ ID NO 79
<211> LENGTH: 174
<212> TYPE: PRT
<213> ORGANISM: Artificial Sequence
<220> FEATURE:
<223> OTHER INFORMATION: TBHBcAg153-T3 carrier

<400> SEQUENCE: 79

Met Glu Asn Leu Glu Arg Leu Asp Ile Tyr Lys Glu Phe Gly Val Ser
1               5                   10                  15

Asp Phe Leu Pro Ser Asp Phe Pro Ser Val Phe Pro Thr Leu Gln
                20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg Gln Ala Ile Leu
50                  55                  60

Cys Trp Gly Glu Leu Arg Asp Phe Ile Asp Trp Met His Glu Gln Gly
65                  70                  75                  80

Gly Gly Gly Gly Ser Gly Gly Gly Thr Gly Ser Glu Phe Gly Gly
                85                  90                  95

Gly Gly Ser Gly Gly Gly Gly Ser Asp Ala Asp Ala Leu Leu Ala Gly
                100                 105                 110

Tyr Leu Arg Ser Lys Tyr Leu Lys His Ile Thr Lys Ala Ile Trp Tyr
            115                 120                 125

His Leu Ser Cys Leu Thr Phe Gly Lys Gln Thr Val His Glu Tyr Leu
130                 135                 140

Val Ser Phe Gly Val Trp Ile Arg Thr Pro Pro Ala Tyr Arg Pro Pro
145                 150                 155                 160

Asn Ala Pro Ile Leu Thr Thr Leu Pro Glu Thr Ser Val Ile
                165                 170

<210> SEQ ID NO 80
<211> LENGTH: 170
<212> TYPE: PRT
<213> ORGANISM: Artificial Sequence
<220> FEATURE:
<223> OTHER INFORMATION: HBHBcAg149-T3 carrier

<400> SEQUENCE: 80

Met Asp Ile Asp Pro Tyr Lys Glu Phe Gly Ala Ser Ser Gln Leu Val
1               5                   10                  15

Ser Phe Leu Pro Ser Asp Phe Phe Pro Ser Val Asn Asp Leu Val Glu
                20                  25                  30

Thr Ser Val Ala Leu Tyr Glu Glu Asp Leu Val Gly Lys Glu His Cys
            35                  40                  45

Ser Pro His His Thr Ala Leu Arg Gln Ala Ile Leu Cys Trp Gly Glu
50                  55                  60

Leu Met Thr Leu Ala Thr Trp Val Arg Ala Thr Val Glu Gly Gly Gly
65                  70                  75                  80

Gly Gly Ser Gly Gly Gly Gly Thr Gly Ser Glu Phe Gly Gly Gly Gly
                85                  90                  95

Ser Gly Gly Gly Gly Ser Gln Asp Ala Ile Ile Gly Tyr Val Gln Thr
```

```
              100                 105                 110
Thr Val Gly Leu Arg Met Arg Gln Gln Ile Trp Phe His Leu Ser Cys
            115                 120                 125

Leu Thr Phe Gly Gln Gln Thr Val Ile Glu Phe Leu Val Ser Phe Gly
            130                 135                 140

Val Trp Ile Arg Thr Pro Pro Ala Tyr Arg Pro Asn Ala Pro Ile
145                 150                 155                 160

Leu Ser Thr Leu Pro Glu His Thr Val Ile
                165                 170
```

<210> SEQ ID NO 81
<211> LENGTH: 633
<212> TYPE: DNA
<213> ORGANISM: Artificial Sequence
<220> FEATURE:
<223> OTHER INFORMATION: nucleotide sequence encoding RBHBcAg189-T3 carrier

<400> SEQUENCE: 81

```
atggacatcg acccgtacaa agaattcggt gcttcttctc agctgatctc tttcctgccg    60
tctgacttct tcccgtctgt tgctgaactg gttgaaacca ccaccgctct gtacgaagaa   120
gaactggttg gtaaagaaca ctgctctccg caccacaccg ctctgcgtca ggctatcctg   180
tgctggggtg aactgatgac cctggctacc tgggttcgta actctgttga aggtggtggt   240
ggtggttctg gtggtggtgg taccggttct gaattcggtg gtggtggttc tggtggtggt   300
ggttctcagg acgctatcgt tcagcaggtt caggcttctg ttggtctgcg tatgcgtcag   360
ctgatgtggt ccacctgtc ttgcctgacc ttcggtcagc gaccgttat cgaattcctg    420
gtttcttcg tgtttggat ccgtaccccg ccggcttacc gtccgccgaa cgctccgatc    480
ctgtctaccc tgccggaaca caccgttatc cgtcgtcgtg gtaacccgcg tgctccgcgt   540
ctccgcgtc gtcgtacccc gtctccgcgt cgtcgtcgtt ctcagtctcc gcgtcgtcgt   600
cgttctcagt ctccggctcc gtctaactgc taa                                633
```

<210> SEQ ID NO 82
<211> LENGTH: 627
<212> TYPE: DNA
<213> ORGANISM: Artificial Sequence
<220> FEATURE:
<223> OTHER INFORMATION: nucleotide sequence encoding TBHBcAg188-T3 carrier

<400> SEQUENCE: 82

```
atggaaaacc tggaacgtct ggacatctac aaagaattcg gtgtttctga cttcctgccg    60
tctgacttct tcccgtctgt tttcccgacc ctgcagcagc tgctggaatc tgttaacgct   120
ctgtacgaag acgaactgac cggtccgaac cactgctctc gcaccacac cgctctgcgt    180
caggctatcc tgtgctgggg tgaactgcgt gacttcatcg actggatgca cgaacagggt   240
ggtggtggtg gttctggtgg tggtggtacc ggttctgaat cggtggtgg tggttctggt   300
ggtggtggtt ctgacgctga cgctctgctg gctggttacc tgcgttctaa atacctgaaa   360
cacatcacca agctatctg gtaccacctg tcttgcctga cttcggtaa acagaccgtt   420
cacgaatacc tggtttcttt cggtgtttgg atccgtaccc cgccggctta ccgtccgccg    480
aacgctccga tcctgaccac cctgccggaa acctctgtta ccgtcgtcg tccggcttct   540
cgtcgttcta cccgctctcc gcgtcgtcgt cgttctcagt ctccgcgtcg tcgtcgttct    600
ccgtctccgc gtccggcttc taactgc                                        627
```

<210> SEQ ID NO 83
<211> LENGTH: 630
<212> TYPE: DNA
<213> ORGANISM: Artificial Sequence
<220> FEATURE:
<223> OTHER INFORMATION: nucleotide sequence encoding HBHBcAg189-T3
      carrier

<400> SEQUENCE: 83

```
atggacatcg acccgtacaa agaattcggt gcttcttctc agctggtttc tttcctgccg      60
tctgacttct cccgtctgt taacgacctg gttgaaacct ctgttgctct gtacgaagaa     120
gacctggttg gtaaagaaca ctgctctccg caccacaccg ctctgcgtca ggctatcctg     180
tgctggggtg aactgatgac cctggctacc tgggttcgtg ctaccgttga aggtggtggt     240
ggtggttctg gtggtggtgg taccggttct gaattcggtg gtggtggttc tggtggtggt     300
ggttctcagg acgctatcat cggttacgtt cagaccaccg ttggtctgcg tatgcgtcag     360
cagatctggt tccacctgtc ttgcctgacc ttcggtcagc agaccgttat cgaattcctg     420
gtttctttcg gtgtttggat ccgtaccccg ccggcttacc gtccgccgaa cgctccgatc     480
ctgtctaccc tgccggaaca caccgttatc cgtcgtcgtg taacccgcg tgctccgcgt     540
tctccgcgtc gtcgtacccc gtctccgcgt cgtcgtcgtt ctcagtctcc gcgtcgtcgt     600
cgttctcagt ctccggctcc gtctaactgc                                     630
```

<210> SEQ ID NO 84
<211> LENGTH: 513
<212> TYPE: DNA
<213> ORGANISM: Artificial Sequence
<220> FEATURE:
<223> OTHER INFORMATION: nucleotide sequence encoding RBHBcAg149-T3
      carrier

<400> SEQUENCE: 84

```
atggacatcg acccgtacaa agaattcggt gcttcttctc agctgatctc tttcctgccg      60
tctgacttct cccgtctgt tgctgaactg gttgaaacca ccaccgctct gtacgaagaa     120
gaactggttg gtaaagaaca ctgctctccg caccacaccg ctctgcgtca ggctatcctg     180
tgctggggtg aactgatgac cctggctacc tgggttcgta actctgttga aggtggtggt     240
ggtggttctg gtggtggtgg taccggttct gaattcggtg gtggtggttc tggtggtggt     300
ggttctcagg acgctatcgt tcagcaggtt caggcttctg ttggtctgcg tatgcgtcag     360
ctgatgtggt tccacctgtc ttgcctgacc ttcggtcagc cgaccgttat cgaattcctg     420
gtttctttcg gtgtttggat ccgtaccccg ccggcttacc gtccgccgaa cgctccgatc     480
ctgtctaccc tgccggaaca caccgttatc taa                                  513
```

<210> SEQ ID NO 85
<211> LENGTH: 522
<212> TYPE: DNA
<213> ORGANISM: Artificial Sequence
<220> FEATURE:
<223> OTHER INFORMATION: nucleotide sequence encoding TBHBcAg153-T3
      carrier

<400> SEQUENCE: 85

```
atggaaaacc tggaacgtct ggacatctac aaagaattcg gtgtttctga cttcctgccg      60
tctgacttct cccgtctgt ttttccgacc ctgcagcagc tgctggaatc tgttaacgct     120
ctgtacgaag acgaactgac cggtccgaac cactgctctc cgcaccacac cgctctgcgt     180
```

```
caggctatcc tgtgctgggg tgaactgcgt gacttcatcg actggatgca cgaacagggt    240
ggtggtggtg gttctggtgg tggtggtacc ggttctgaat cggtggtgg tggttctggt    300 ggtggtggtt ctgacgctga cgctctgctg ctggttacc tgcgttctaa atacctgaaa    360
cacatcacca aagctatctg gtaccacctg tcttgcctga ccttcggtaa acagaccgtt    420
cacgaatacc tggtttcttt cggtgtttgg atccgtaccc cgccggctta ccgtccgccg    480
aacgctccga tcctgaccac cctgccggaa acctctgtta tc                      522
```

<210> SEQ ID NO 86
<211> LENGTH: 510
<212> TYPE: DNA
<213> ORGANISM: Artificial Sequence
<220> FEATURE:
<223> OTHER INFORMATION: nucleotide sequence encoding HBHBcAg149-T3
      carrier

<400> SEQUENCE: 86

```
atggacatcg acccgtacaa agaattcggt gcttcttctc agctggtttc tttcctgccg    60
tctgacttct tcccgtctgt taacgacctg gttgaaacct ctgttgctct gtacgaagaa   120
gacctggttg gtaagaaaca ctgctctccg caccacaccg ctctgcgtca ggctatcctg   180
tgctggggtg aactgatgac cctggctacc tgggttcgtg ctaccgttga aggtggtggt   240
ggtggttctg gtggtggtgg taccggttct gaattcggtg gtggtggttc tggtggtggt   300
ggttctcagg acgctatcat cggttacgtt cagaccaccg ttggtctgcg tatgcgtcag   360
cagatctggt tccacctgtc ttgcctgacc ttcggtcagc agaccgttat cgaattcctg   420
gtttctttcg gtgtttggat ccgtaccccg ccggcttacc gtccgccgaa cgctccgatc   480
ctgtctaccc tgccggaaca caccgttatc                                    510
```

<210> SEQ ID NO 87
<211> LENGTH: 10
<212> TYPE: PRT
<213> ORGANISM: Homo sapiens

<400> SEQUENCE: 87

Phe Leu Pro Ser Asp Phe Phe Pro Ser Val
1               5                   10

<210> SEQ ID NO 88
<211> LENGTH: 20
<212> TYPE: PRT
<213> ORGANISM: Homo sapiens

<400> SEQUENCE: 88

Pro His His Thr Ala Leu Arg Gln Ala Ile Leu Cys Trp Gly Glu Leu
1               5                   10                  15

Met Thr Leu Ala
            20

<210> SEQ ID NO 89
<211> LENGTH: 21
<212> TYPE: PRT
<213> ORGANISM: Homo sapiens

<400> SEQUENCE: 89

Val Ser Phe Gly Val Trp Ile Arg Thr Pro Pro Ala Tyr Arg Pro Pro
1               5                   10                  15

Asn Ala Pro Ile Leu

<210> SEQ ID NO 90
<211> LENGTH: 233
<212> TYPE: PRT
<213> ORGANISM: Artificial Sequence
<220> FEATURE:
<223> OTHER INFORMATION: Recombinant protein RBHBcAg189-T3-SEQ22

<400> SEQUENCE: 90

```
Met Asp Ile Asp Pro Tyr Lys Glu Phe Gly Ala Ser Ser Gln Leu Ile
1               5                   10                  15

Ser Phe Leu Pro Ser Asp Phe Phe Pro Ser Val Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Arg Asn Ser Val Glu Gly Gly Gly
65                  70                  75                  80

Gly Gly Ser Gly Gly Gly Thr Gly Ser Ser Thr Thr Ser Thr
            85                  90                  95

Gly Pro Cys Lys Thr Cys Thr Thr Pro Ala Gln Gly Thr Ser Met Phe
            100                 105                 110

Pro Glu Phe Gly Gly Gly Ser Gly Gly Gly Ser Gln Asp Ala
            115                 120                 125

Ile Val Gln Gln Val Gln Ala Ser Val Gly Leu Arg Met Arg Gln Leu
    130                 135                 140

Met Trp Phe His Leu Ser Cys Leu Thr Phe Gly Gln Pro Thr Val Ile
145                 150                 155                 160

Glu Phe Leu Val Ser Phe Gly Val Trp Ile Arg Thr Pro Pro Ala Tyr
                165                 170                 175

Arg Pro Pro Asn Ala Pro Ile Leu Ser Thr Leu Pro Glu His Thr Val
            180                 185                 190

Ile Arg Arg Arg Gly Asn Pro Arg Ala Pro Arg Ser Pro Arg Arg Arg
        195                 200                 205

Thr Pro Ser Pro Arg Arg Arg Ser Gln Ser Pro Arg Arg Arg
    210                 215                 220

Ser Gln Ser Pro Ala Pro Ser Asn Cys
225                 230
```

<210> SEQ ID NO 91
<211> LENGTH: 193
<212> TYPE: PRT
<213> ORGANISM: Artificial Sequence
<220> FEATURE:
<223> OTHER INFORMATION: Recombinant protein RBHBcAg149-T3-SEQ22

<400> SEQUENCE: 91

```
Met Asp Ile Asp Pro Tyr Lys Glu Phe Gly Ala Ser Ser Gln Leu Ile
1               5                   10                  15

Ser Phe Leu Pro Ser Asp Phe Phe Pro Ser Val Ala Glu Leu Val Glu
            20                  25                  30

Thr Thr Thr Ala Leu Tyr Glu Glu Glu Leu Val Gly Lys Glu His Cys
        35                  40                  45

Ser Pro His His Thr Ala Leu Arg Gln Ala Ile Leu Cys Trp Gly Glu
    50                  55                  60
```

Leu Met Thr Leu Ala Thr Trp Val Arg Asn Ser Val Glu Gly Gly Gly
65                  70                  75                  80

Gly Gly Ser Gly Gly Gly Thr Gly Ser Ser Thr Thr Ser Thr
            85                  90                  95

Gly Pro Cys Lys Thr Cys Thr Thr Pro Ala Gln Gly Thr Ser Met Phe
            100                 105                 110

Pro Glu Phe Gly Gly Gly Ser Gly Gly Gly Ser Gln Asp Ala
            115                 120                 125

Ile Val Gln Gln Val Gln Ala Ser Val Gly Leu Arg Met Arg Gln Leu
130                 135                 140

Met Trp Phe His Leu Ser Cys Leu Thr Phe Gly Gln Pro Thr Val Ile
145                 150                 155                 160

Glu Phe Leu Val Ser Phe Gly Val Trp Ile Arg Thr Pro Pro Ala Tyr
            165                 170                 175

Arg Pro Pro Asn Ala Pro Ile Leu Ser Thr Leu Pro Glu His Thr Val
            180                 185                 190

Ile

<210> SEQ ID NO 92
<211> LENGTH: 232
<212> TYPE: PRT
<213> ORGANISM: Artificial Sequence
<220> FEATURE:
<223> OTHER INFORMATION: Recombinant protein TBHBcAg188-T3-SEQ22

<400> SEQUENCE: 92

Met Glu Asn Leu Glu Arg Leu Asp Ile Tyr Lys Glu Phe Gly Val Ser
1               5                   10                  15

Asp Phe Leu Pro Ser Asp Phe Pro Ser Val Phe Pro Thr Leu Gln
            20                  25                  30

Gln Leu Leu Glu Ser Val Asn Ala Leu Tyr Glu Asp Glu Leu Thr Gly
            35                  40                  45

Pro Asn His Cys Ser Pro His His Thr Ala Leu Arg Gln Ala Ile Leu
            50                  55                  60

Cys Trp Gly Glu Leu Arg Asp Phe Ile Asp Trp Met His Glu Gln Gly
65                  70                  75                  80

Gly Gly Gly Gly Ser Gly Gly Gly Thr Gly Ser Ser Thr Thr
            85                  90                  95

Ser Thr Gly Pro Cys Lys Thr Cys Thr Thr Pro Ala Gln Gly Thr Ser
            100                 105                 110

Met Phe Pro Glu Phe Gly Gly Gly Ser Gly Gly Gly Ser Asp
            115                 120                 125

Ala Asp Ala Leu Leu Ala Gly Tyr Leu Arg Ser Lys Tyr Leu Lys His
130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Val Trp Ile Arg Thr
            165                 170                 175

Pro Pro Ala Tyr Arg Pro Pro Asn Ala Pro Ile Leu Thr Thr Leu Pro
            180                 185                 190

Glu Thr Ser Val Ile Arg Arg Pro Ala Ser Arg Ser Thr Pro
            195                 200                 205

Ser Pro Arg Arg Arg Arg Ser Gln Ser Pro Arg Arg Arg Ser Pro
210                 215                 220

Ser Pro Arg Pro Ala Ser Asn Cys

<210> SEQ ID NO 93
<211> LENGTH: 197
<212> TYPE: PRT
<213> ORGANISM: Artificial Sequence
<220> FEATURE:
<223> OTHER INFORMATION: Recombinant protein TBHBcAg153-T3-SEQ22

<400> SEQUENCE: 93

```
Met Glu Asn Leu Glu Arg Leu Asp Ile Tyr Lys Glu Phe Gly Val Ser
1               5                   10                  15

Asp Phe Leu Pro Ser Asp Phe Pro Ser Val Phe Pro Thr Leu Gln
            20                  25                  30

Gln Leu Leu Glu Ser Val Asn Ala Leu Tyr Glu Asp Glu Leu Thr Gly
        35                  40                  45

Pro Asn His Cys Ser Pro His His Thr Ala Leu Arg Gln Ala Ile Leu
    50                  55                  60

Cys Trp Gly Glu Leu Arg Asp Phe Ile Asp Trp Met His Glu Gln Gly
65                  70                  75                  80

Gly Gly Gly Gly Ser Gly Gly Gly Thr Gly Ser Ser Ser Thr Thr
                85                  90                  95

Ser Thr Gly Pro Cys Lys Thr Cys Thr Thr Pro Ala Gln Gly Thr Ser
                100                 105                 110

Met Phe Pro Glu Phe Gly Gly Gly Ser Gly Gly Gly Ser Asp
            115                 120                 125

Ala Asp Ala Leu Leu Ala Gly Tyr Leu Arg Ser Lys Tyr Leu Lys His
    130                 135                 140

Ile Thr Lys Ala Ile Trp Tyr His Leu Ser Cys Leu Thr Phe Gly Lys
145                 150                 155                 160

Gln Thr Val His Glu Tyr Leu Val Ser Phe Gly Val Trp Ile Arg Thr
                165                 170                 175

Pro Pro Ala Tyr Arg Pro Pro Asn Ala Pro Ile Leu Thr Leu Pro
            180                 185                 190

Glu Thr Ser Val Ile
        195
```

<210> SEQ ID NO 94
<211> LENGTH: 233
<212> TYPE: PRT
<213> ORGANISM: Artificial Sequence
<220> FEATURE:
<223> OTHER INFORMATION: Recombinant protein HBHBcAg189-T3-SEQ22

<400> SEQUENCE: 94

```
Met Asp Ile Asp Pro Tyr Lys Glu Phe Gly Ala Ser Ser Gln Leu Val
1               5                   10                  15

Ser Phe Leu Pro Ser Asp Phe Phe Pro Ser Val Asn Asp Leu Val Glu
            20                  25                  30

Thr Ser Val Ala Leu Tyr Glu Glu Asp Leu Val Gly Lys Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Arg Ala Thr Val Glu Gly Gly Gly
65                  70                  75                  80

Gly Gly Ser Gly Gly Gly Thr Gly Ser Ser Ser Thr Thr Ser Thr
                85                  90                  95
```

```
Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Gln Asp Ala
            115                 120                 125

Ile Ile Gly Tyr Val Gln Thr Thr Val Gly Leu Arg Met Arg Gln Gln
        130                 135                 140

Ile Trp Phe His Leu Ser Cys Leu Thr Phe Gly Gln Gln Thr Val Ile
145                 150                 155                 160

Glu Phe Leu Val Ser Phe Gly Val Trp Ile Arg Thr Pro Ala Tyr
                    165                 170                 175

Arg Pro Pro Asn Ala Pro Ile Leu Ser Thr Leu Pro Glu His Thr Val
            180                 185                 190

Ile Arg Arg Arg Gly Asn Pro Arg Ala Pro Arg Ser Pro Arg Arg Arg
        195                 200                 205

Thr Pro Ser Pro Arg Arg Arg Ser Gln Ser Pro Arg Arg Arg
        210                 215                 220

Ser Gln Ser Pro Ala Pro Ser Asn Cys
225                 230
```

<210> SEQ ID NO 95
<211> LENGTH: 193
<212> TYPE: PRT
<213> ORGANISM: Artificial Sequence
<220> FEATURE:
<223> OTHER INFORMATION: Recombinant protein HBHBcAg149-T3-SEQ22

<400> SEQUENCE: 95

```
Met Asp Ile Asp Pro Tyr Lys Glu Phe Gly Ala Ser Ser Gln Leu Val
1               5                   10                  15

Ser Phe Leu Pro Ser Asp Phe Phe Pro Ser Val Asn Asp Leu Val Glu
            20                  25                  30

Thr Ser Val Ala Leu Tyr Glu Glu Asp Leu Val Gly Lys Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Arg Ala Thr Val Glu Gly Gly Gly
65                  70                  75                  80

Gly Gly Ser Gly Gly Gly Thr Gly Ser Ser Ser Thr Thr Ser Thr
            85                  90                  95

Gly Pro Cys Lys Thr Cys Thr Thr Pro Ala Gln Gly Thr Ser Met Phe
            100                 105                 110

Pro Glu Phe Gly Gly Gly Gly Ser Gly Gly Gly Ser Gln Asp Ala
            115                 120                 125

Ile Ile Gly Tyr Val Gln Thr Thr Val Gly Leu Arg Met Arg Gln Gln
        130                 135                 140

Ile Trp Phe His Leu Ser Cys Leu Thr Phe Gly Gln Gln Thr Val Ile
145                 150                 155                 160

Glu Phe Leu Val Ser Phe Gly Val Trp Ile Arg Thr Pro Ala Tyr
                    165                 170                 175

Arg Pro Pro Asn Ala Pro Ile Leu Ser Thr Leu Pro Glu His Thr Val
            180                 185                 190

Ile
```

<210> SEQ ID NO 96
<211> LENGTH: 169
<212> TYPE: PRT

<213> ORGANISM: Artificial Sequence
<220> FEATURE:
<223> OTHER INFORMATION: Recombinant protein RBHBcAg149n-T3-SEQ22

<400> SEQUENCE: 96

```
Met Asp Ile Asp Pro Tyr Lys Glu Phe Gly Ala Ser Ser Gln Leu Ile
1               5                   10                  15

Ser Phe Leu Pro Ser Asp Phe Phe Pro Ser Val Ala Glu Leu Val Glu
            20                  25                  30

Thr Thr Thr Ala Leu Tyr Glu Glu Leu Val Gly Lys Glu His Cys
        35                  40                  45

Ser Pro His His Thr Ala Leu Arg Gln Ala Ile Leu Cys Trp Gly Glu
50                  55                  60

Leu Met Thr Leu Ala Thr Trp Val Arg Asn Ser Val Glu Gly Ser Ser
65                  70                  75                  80

Thr Thr Ser Thr Gly Pro Cys Lys Thr Cys Thr Thr Pro Ala Gln Gly
                85                  90                  95

Thr Ser Met Phe Pro Gln Asp Ala Ile Val Gln Val Gln Ala Ser
            100                 105                 110

Val Gly Leu Arg Met Arg Gln Leu Met Trp Phe His Leu Ser Cys Leu
            115                 120                 125

Thr Phe Gly Gln Pro Thr Val Ile Glu Phe Leu Val Ser Phe Gly Val
        130                 135                 140

Trp Ile Arg Thr Pro Pro Ala Tyr Arg Pro Pro Asn Ala Pro Ile Leu
145                 150                 155                 160

Ser Thr Leu Pro Glu His Thr Val Ile
                165
```

<210> SEQ ID NO 97
<211> LENGTH: 50
<212> TYPE: DNA
<213> ORGANISM: Artificial Sequence
<220> FEATURE:
<223> OTHER INFORMATION: primer

<400> SEQUENCE: 97
aactttaaga aggagatata catatggaca tcgacccgta caaagaattc         50

<210> SEQ ID NO 98
<211> LENGTH: 60
<212> TYPE: DNA
<213> ORGANISM: Artificial Sequence
<220> FEATURE:
<223> OTHER INFORMATION: primer

<400> SEQUENCE: 98
gagttgtgca ggttttgcat ggtccggtgc tggttgttga tgaaccttca acagagttac      60

<210> SEQ ID NO 99
<211> LENGTH: 60
<212> TYPE: DNA
<213> ORGANISM: Artificial Sequence
<220> FEATURE:
<223> OTHER INFORMATION: primer

<400> SEQUENCE: 99
caaaacctgc acaactcctg ctcaaggaac tctatgtttt ccccaggacg ctatcgttca      60

<210> SEQ ID NO 100
<211> LENGTH: 53
<212> TYPE: DNA

```
<213> ORGANISM: Artificial Sequence
<220> FEATURE:
<223> OTHER INFORMATION: primer

<400> SEQUENCE: 100
tggtgctcga gtgcggccgc aagcttagat aacggtgtgt tccggcaggg tag          53
```

POLYPEPTIDE CARRIER FOR PRESENTING TARGET POLYPEPTIDE AND USES THEREOF

TECHNICAL FIELD

The invention relates to the fields of genetically engineering vaccines, molecular virology and immunology. In addition, the invention specifically relates to the field of treatment of Hepatitis B virus (HBV) infection. In particular, the invention relates to a nucleic acid molecule, comprising a nucleotide sequence encoding a polypeptide carrier (peptide carrier), and being used for insertion of a nucleotide sequence encoding a target polypeptide. In particular, after the nucleic acid molecule of the invention has a nucleotide sequence encoding a target polypeptide inserted therein and is expressed as a recombinant protein, the polypeptide carrier can present the target polypeptide (e.g., a target antigen or a target epitope in an antigen), and/or the recombinant protein can form a virus-like particle and present the target polypeptide. In addition, the invention further relates to a recombinant protein comprising the polypeptide carrier and a target polypeptide. Furthermore, the invention further relates to use of the nucleic acid molecule and the recombinant protein. In addition, the invention specifically relates to a vaccine or a pharmaceutical composition useful for preventing, alleviating or treating HBV infection or a disease associated with HBV infection (e.g., hepatitis B), comprising a recombinant protein comprising the polypeptide carrier of the invention and an epitope from HBV.

BACKGROUND ART

Vaccines are effective means for combating infectious diseases. Depending on applicable people, vaccines can be divided into prophylactic vaccines and therapeutic vaccines. Prophylactic vaccines are mainly used to prevent virus infections, including attenuated vaccines, inactivated vaccines, and genetically engineering vaccines, which protect organisms from virus infections mainly by inducing neutralizing antibodies in the organisms. Therapeutic vaccines are mainly used to treat persistent virus infection and diseases such as tumor. In these diseases, patients are generally immune-tolerant to a target antigen, and therefore, researchers have tried several forms of vaccines to induce generation of an effective immune response to a target antigen in organisms. Therapeutic vaccines mainly include nucleic acid vaccines, viral vector vaccines, genetically engineering vaccines, etc. Among them, genetically engineering vaccines have significant advantages.

The genetically engineering vaccines that have been commercially available, include hepatitis B virus (HBV) vaccines, Human Papillomavirus (HPV) vaccines, and Hepatitis E virus (HEV) vaccines, all of which are in the form of virus-like particles (VLPs). Virus-like particles refer to hollow particles formed by one or more structural proteins of a certain virus, which do not comprise viral nucleic acid, cannot be self-replicated, but are the same as or similar to true virions in terms of morphology and structure. Virus-like particles have the following advantages: strong immunogenicity, high safety, being not easily inactivated, and being able to present an exogenous peptide fragment and induce specific immune response to the exogenous peptide fragment in organisms; and therefore, have an important application value in the field of vaccines.

Now, about 2 billion people have been infected by HBV worldwide, about 350 million of which have chronic HBV infection, and the risk of these infected people finally dying of liver diseases associated with HBV infection could reach 15%-25%. More than 1 million people died of end-stage liver diseases caused by hepatitis B worldwide every year. China is an area severely afflicted by HBV infection, and there are about 93 million people carrying hepatitis B now. In recent years, with the continuous improvement of the case reporting system, the incidence and mortality of hepatitis B-related diseases increase instead of decreasing.

At present, drugs for treating chronic HBV infection can mainly be divided into two classes, i.e., Interferon and nucleoside/nucleotide analogues (NAs). The final goal of treating chronic HBV infection is to prevent the occurrence of end-stage liver diseases such as serious hepatitis (hepatic failure), hepatic cirrhosis and liver cancer; the best clinical endpoint is to enable patients to achieve serological negative conversion or serological conversion of hepatitis B surface antigen, i.e., completely clean HBV. However, there are a very limited number of existing drugs that can achieve the goal. Therefore, it is urgent and necessary to develop novel, creative therapeutic drugs and methods that can clean virus more effectively, in particular, can clean HBsAg effectively or greatly decrease HBsAg level, for patients with chronic HBV infection, and it is a potential strategy to develop therapeutic vaccines.

CONTENTS OF INVENTION

The inventors of the present application, based on three bat-derived hepatitis B virus core antigens (i.e., roundleaf bat HBV (RBHBV) core antigen (RBHBcAg); tent-making bat HBV (TBHBV) core antigen (TBHBcAg); and horseshoe bat HBV (HBHBV) core antigen (HBHBcAg)), have developed a class of new polypeptide carriers (peptide carriers) for presenting target polypeptides. Therefore, the invention provides a nucleic acid molecule, comprising a nucleotide sequence encoding a polypeptide carrier. Such a nucleic acid molecule can have a nucleotide sequence encoding a target polypeptide inserted therein, and be expressed as a recombinant protein comprising the polypeptide carrier and the target polypeptide (e.g., a target antigen, or a target epitope in an antigen). Furthermore, the recombinant protein produced can form VLP effectively, and can present the target polypeptide inserted therein on the surface of VLP, so that the target polypeptide can be effectively recognized by immune system in an organism, thereby inducing generation of a specific immune response to the target polypeptide in the organism. Therefore, the polypeptide carrier of the invention, can be used as a carrier for vaccine, to present a target polypeptide, for example, a peptide fragment (e.g., an epitope) from a target antigen, and a recombinant protein comprising the polypeptide carrier of the invention and a target polypeptide can be used as a vaccine, to induce a specific immune response to the target polypeptide in an organism.

Furthermore, the inventors of the present application also found that the C-terminus of RBHBcAg protein, TBHBcAg protein and HBHBcAg protein is a lysine-rich region, and is not necessary for the assembly of VLP. Therefore, the polypeptide carrier of the invention may not comprise the C-terminus of RBHBcAg protein, TBHBcAg protein and HBHBcAg protein. For example, the RBHBcAg carrier of the invention may have the amino acids from positions 145-189 of RBHBcAg protein deleted partially or completely (e.g., have the amino acids from positions 150-189 of RBHBcAg protein deleted); the TBHBcAg carrier of the invention may have the amino acids from positions 149-188 of TBHBcAg protein deleted partially or completely (e.g., have the amino acids from positions 154-188 of TBHBcAg protein deleted); the HBHBcAg carrier of the invention may have the amino acids from positions 145-189 of HBHBcAg protein deleted partially or completely (e.g., have the amino acids from positions 150-189 of HBHBcAg protein deleted).

Furthermore, the inventors of the present application also found that a portion of the amino acid sequences of RBHBcAg protein, TBHBcAg protein and HBHBcAg protein can be substituted by a human T cell epitope without affecting the assembly of VLP. Therefore, in order to enhance the immune response of a human body to a recombinant protein comprising the polypeptide carrier of the present invention and a target polypeptide, the inventors of the present application further modified the polypeptide carrier of the present invention, that is, by substituting a portion of amino acid sequence of the polypeptide carrier with a human T cell epitope, thus obtaining the optimized polypeptide carrier (i.e., the polypeptide carrier carrying the human T cell epitope). For example, the inventors of the present application have found that the amino acid residues at positions 18-27, 50-69, and/or 120-140 of the RBHBcAg protein can be substituted with a human T cell epitope (e.g. an MHC I restricted epitope and/or an MHC II restricted epitope) without affecting the assembly of VLP. TBHBcAg protein and HBHBcAg protein have similar properties. Therefore, the polypeptide carriers RBHBcAg, TBHBcAg and HBHBcAg can be modified correspondingly to obtain the polypeptide carriers RBHBcAg-T, TBHBcAg-T and HBHBcAg-T carrying the human T cell epitope.

In addition, the inventors of the present application also found surprisingly that the polypeptide carrier of the invention is particularly suitable for presenting antigen epitope from human hepatitis B virus (e.g., an epitope of HBsAg from human HBV), and is able to induce a very strong and specific immune response for cleaning HBsAg in a subject, with an efficacy significantly better than that of the existing hepatitis B vaccines (e.g., vaccines comprising the same epitope and constructed by using HBcAg of human HBV as a polypeptide carrier). Thus, the invention further provides a polypeptide carrier particularly suitable for presenting antigen epitopes from human hepatitis B virus.

Therefore, in an aspect, the invention provides a nucleic acid molecule, comprising a nucleotide sequence encoding a polypeptide carrier, or a variant thereof, wherein the variant has an identity of at least 90% (e.g., at least 91%, 92%, 93%, 94%, 95%, 96%, 97%, 98%, or 99%) to the nucleotide sequence, or is capable of hybridizing to the nucleotide sequence under a stringent condition or a high stringent condition, wherein, the polypeptide carrier is selected from:

(1) RBHBcAg carrier, which differs from roundleaf bat HBV core antigen protein (RBHBcAg protein; e.g., its amino acid sequence is set forth in SEQ ID NO: 1) by difference comprising the following: (a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of RBHBcAg protein are deleted or substituted with a linker (e.g., a flexible linker; e.g., a linker set forth in SEQ ID NO: 43); and (b) optionally, 1-40 amino acid residues (e.g., 1-5, 5-10, 10-15, 15-20, 20-25, 25-30, 30-35, or 35-40 amino acid residues) are deleted at C-terminus of RBHBcAg protein;

(2) TBHBcAg carrier, which differs from tent-making bat HBV core antigen protein (TBHBcAg protein; e.g., its amino acid sequence is set forth in SEQ ID NO: 2) by difference comprising the following: (a) one or more amino acid residues (e.g., 1, 2, 3, 4 or 5 amino acid residues; e.g., amino acid residues from positions 80-84, amino acid residues from positions 80-83, or amino acid residues from positions 80-82) of the amino acid residues from positions 80-84 at N-terminus of TBHBcAg protein are deleted or substituted with a linker (e.g., a flexible linker; e.g., a linker set forth in SEQ ID NO: 43); and (b) optionally, 1-35 amino acid residues (e.g., 1-5, 5-10, 10-15, 15-20, 20-25, 25-30, or 30-35 amino acid residues) are deleted at C-terminus of TBHBcAg;

(3) HBHBcAg carrier, which differs from horseshoe bat HBV core antigen protein (HBHBcAg protein; e.g., its amino acid sequence is set forth in SEQ ID NO: 3) by difference comprising the following: (a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of HBHBcAg protein are deleted or substituted with a linker (e.g., a flexible linker; e.g., a linker set forth in SEQ ID NO: 43); and (b) optionally, 1-40 amino acid residues (e.g., 1-5, 5-10, 10-15, 15-20, 20-25, 25-30, 30-35, or 35-40 amino acid residues) are deleted at C-terminus of HBHBcAg protein.

RBHBcAg Carrier

In a preferred embodiment, RBHBcAg protein is a wild type RBHBcAg. In a preferred embodiment, the amino acid sequence of RBHBcAg protein is set forth in SEQ ID NO: 1.

In a preferred embodiment, the difference between RBHBcAg carrier and RBHBcAg protein comprises the following: one or more contiguous amino acid residues (e.g., 1, 2, 3, 4, 5 or 6 contiguous amino acid residues) of the amino acid residues from positions 78-83 at N-terminus of RBHBcAg protein are deleted or substituted with a linker. For example, the amino acid residues from positions 78-83, amino acid residues from positions 78-82, amino acid residues from positions 78-81, amino acid residues from positions 78-80, amino acid residues from positions 78-79, amino acid residues from positions 79-83, amino acid residues from positions 79-82, amino acid residues from positions 79-81, amino acid residues from positions 79-80, amino acid residues from positions 80-83, amino acid residues from positions 80-82, amino acid residues from positions 80-81, amino acid residues from positions 81-83, amino acid residues from positions 81-82, amino acid residues from positions 82-83, amino acid residue at position 78, amino acid residue at position 79, amino acid residue at position 80, amino acid residue at position 81, amino acid residue at position 82, or amino acid residue at position 83, at N-terminus of RBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGS (SEQ ID NO: 43).

In a preferred embodiment, the difference between RBHBcAg carrier and RBHBcAg protein comprises the following: (1) one or more contiguous amino acid residues (e.g., 1, 2, 3, 4, 5 or 6 contiguous amino acid residues) of the amino acid residues from positions 78-83 at N-terminus of RBHBcAg protein are deleted or substituted with a linker, as defined above; and (2) 1-40 amino acid residues at C-terminus of RBHBcAg protein are deleted. In a preferred embodiment, 1-5, 5-10, 10-15, 15-20, 20-25, 25-30, 30-35, or 35-40 amino acid residues are deleted at C-terminus of RBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues, are deleted.

TBHBcAg Carrier

In a preferred embodiment, TBHBcAg protein is a wild type TBHBcAg. In a preferred embodiment, the amino acid sequence of TBHBcAg protein is set forth in SEQ ID NO: 2.

In a preferred embodiment, the difference between TBHBcAg carrier and TBHBcAg protein comprises the following: one or more contiguous amino acid residues (e.g., 1, 2, 3, 4, or 5 contiguous amino acid residues) of the amino acid residues from positions 80-84 at N-terminus of TBHBcAg protein are deleted or substituted with a linker. For example, the amino acid residues from positions 80-84, amino acid residues from positions 80-83, amino acid residues from positions 80-82, amino acid residues from positions 80-81, amino acid residues from positions 81-84, amino acid residues from positions 81-83, amino acid residues from positions 81-82, amino acid residues from positions 82-84, amino acid residues from positions 82-83, amino acid residues from positions 83-84, amino acid residue at position 80, amino acid residue at position 81, amino acid residue at position 82, amino acid residue at position 83, or amino acid residue at position 84, at N-terminus of TBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

In a preferred embodiment, the difference between TBHBcAg carrier and TBHBcAg protein in comprises the following: (1) one or more contiguous amino acid residues (e.g., 1, 2, 3, 4, or 5 contiguous amino acid residues) of the amino acid residues from positions 80-84 at N-terminus of TBHBcAg protein are deleted or substituted with a linker, as defined above; and (2) 1-35 amino acid residues at C-terminus of TBHBcAg protein are deleted. In a preferred embodiment, 1-5, 5-10, 10-15, 15-20, 20-25, 25-30, or 30-35 amino acid residues are deleted at C-terminus of TBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues are deleted.

HBHBcAg Carrier

In a preferred embodiment, HBHBcAg protein is a wild type HBHBcAg. In a preferred embodiment, the amino acid sequence of HBHBcAg is set forth in SEQ ID NO: 3.

In a preferred embodiment, the difference between HBHBcAg carrier and HBHBcAg protein comprises the following: one or more contiguous amino acid residues (e.g., 1, 2, 3, 4, 5 or 6 contiguous amino acid residues) of the amino acid residues from positions 78-83 at N-terminus of HBHBcAg protein are deleted or substituted with a linker. For example, the amino acid residues from positions 78-83, amino acid residues from positions 78-82, amino acid residues from positions 78-81, amino acid residues from positions 78-80, amino acid residues from positions 78-79, amino acid residues from positions 79-83, amino acid residues from positions 79-82, amino acid residues from positions 79-81, amino acid residues from positions 79-80, amino acid residues from positions 80-83, amino acid residues from positions 80-82, amino acid residues from positions 80-81, amino acid residues from positions 81-83, amino acid residues from positions 81-82, amino acid residues from positions 82-83, amino acid residue at position 78, amino acid residue at position 79, amino acid residue at position 80, amino acid residue at position 81, amino acid residue at position 82, or amino acid residue at position 83, at N-terminus of HBHBcAg protein, may be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

In a preferred embodiment, the difference between HBHBcAg carrier and HBHBcAg protein comprises the following: (1) one or more contiguous amino acid residues (e.g., 1, 2, 3, 4, 5 or 6 contiguous amino acid residues) of the amino acid residues from positions 78-83 at N-terminus of HBHBcAg protein are deleted or substituted with a linker, as defined above; and (2) 1-40 amino acid residues at C-terminus of HBHBcAg protein are deleted. In a preferred embodiment, 1-5, 5-10, 10-15, 15-20, 20-25, 25-30, 30-35, or 35-40 amino acid residues are deleted at C-terminus of HBHBcAg protein; for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues are deleted.

In a certain preferred embodiment, the polypeptide carrier also carries a T cell epitope. In a certain preferred embodiment, the T cell epitope is a human T cell epitopes. In a certain preferred embodiment, the T cell epitope is selected from an MHC I restricted human T cell epitope and an MHC II restricted human T cell epitope. In a certain preferred embodiment, the MHC 1 restricted human T cell epitope is set forth in SEQ ID NO: 87. In a certain preferred embodiment, the MHC II restricted human T cell epitope is set forth in SEQ ID NO: 88 or 89.

In a certain preferred embodiment, the polypeptide carrier carries a human T cell epitope, and is selected from:

(1) RBHBcAg-T carrier, which differs from roundleaf bat HBV core antigen protein (RBHBcAg protein; e.g., its amino acid sequence is set forth in SEQ ID NO: 1) by difference comprising the following:

(1a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of RBHBcAg protein are deleted or substituted with a linker (e.g., a flexible linker; e.g., a linker set forth in SEQ ID NO: 43);

(1b) one or more amino acid residues of the amino acid residues from positions 18-27, one or more amino acid residues of the amino acid residues from positions 50-69 and/or one or more amino acid residues of the amino acid residues from positions 120-140 at N-terminus of RBHBcAg protein are each independently substituted with a human T cell epitope (e.g. an MHC I restricted human T cell epitope and/or an MHC II restricted human T cell epitope); and (1c) optionally, 1-40 amino acid residues (e.g., 1-5, 5-10, 10-15, 15-20, 20-25, 25-30, 30-35, or 35-40 amino acid residues) are deleted at C-terminus of RBHBcAg protein;

(2) TBHBcAg-T carrier, which differs from tent-making bat HBV core antigen protein (TBHBcAg protein; e.g., its amino acid sequence is set forth in SEQ ID NO: 2) by difference comprising the following:

(2a) one or more amino acid residues (e.g., 1, 2, 3, 4 or 5 amino acid residues; e.g., amino acid residues from positions 80-84, amino acid residues from positions 80-83, or amino acid residues from positions 80-82) of the amino acid residues from positions 80-84 at N-terminus of TBHBcAg protein are deleted or substituted with a linker (e.g., a flexible linker; e.g., a linker set forth in SEQ ID NO: 43);

(2b) one or more amino acid residues of the amino acid residues from positions 18-27, one or more amino acid residues of the amino acid residues from positions 54-73 and/or one or more amino acid residues of the amino acid residues from positions 124-144 at N-terminus of TBHBcAg protein are each independently substituted with a human T cell epitope (e.g. an MHC I restricted human T cell epitope and/or an MHC 11 restricted human T cell epitope); and (2c) optionally, 1-35 amino acid residues (e.g., 1-5, 5-10, 10-15, 15-20, 20-25, 25-30, or 30-35 amino acid residues) are deleted at C-terminus of TBHBcAg; and (3) HBHB-cAg-T carrier, which differs from horseshoe bat HBV core antigen protein (HBHBcAg protein; e.g., its amino acid sequence is set forth in SEQ ID NO: 3) include by difference comprising the following:

(3a) one or more amino acid residues (e.g., 1, 2, 3, 4, 5 or 6 amino acid residues; e.g., amino acid residues from positions 78-83, amino acid residues from positions 78-82, amino acid residues from positions 78-81, or amino acid residues from positions 78-80) of the amino acid residues from positions 78-83 at N-terminus of HBHBcAg protein are deleted or substituted with a linker (e.g., a flexible linker; e.g., a linker set forth in SEQ ID NO: 43);

(3b) one or more amino acid residues of the amino acid residues from positions 18-27, one or more amino acid residues of the amino acid residues from positions 50-69 and/or one or more amino acid residues of the amino acid residues from positions 120-140 at N-terminus of HBHB-cAg protein are each independently substituted with a human T cell epitope (e.g. an MHC I restricted human T cell epitope and/or an MHC II restricted human T cell epitope); and (3c) optionally, 1-40 amino acid residues (e.g., 1-5, 5-10, 10-15, 15-20, 20-25, 25-30, 30-35, or 35-40 amino acid residues) are deleted at C-terminus of HBHBcAg protein.

RBHBcAg-T Carrier

In a preferred embodiment, RBHBcAg protein is a wild type RBHBcAg. In a preferred embodiment, the amino acid sequence of RBHBcAg protein is set forth in SEQ ID NO: 1.

In a preferred embodiment, the difference between RBHBcAg-T carrier and RBHBcAg protein comprises the following: (i) one or more contiguous amino acid residues (e.g., 1, 2, 3, 4, 5 or 6 contiguous amino acid residues) of the amino acid residues from positions 78-83 at N-terminus of RBHBcAg protein are deleted or substituted with a linker; (ii) one or more amino acid residues of the amino acid residues from positions 18-27, one or more amino acid residues of the amino acid residues from positions 50-69 and/or one or more amino acid residues of the amino acid residues from positions 120-140 at N-terminus of RBHB-cAg protein are each independently substituted with a human T cell epitope (e.g. an MHC I or MHC II restricted human T cell epitope); and (iii) optionally, 1-40 amino acid residues (e.g., 1-5, 5-10, 10-15, 15-20, 20-25, 25-30, 30-35, or 35-40 amino acid residues) are deleted at C-terminus of RBHBcAg protein.

About the Difference (i)

In a certain preferred embodiment, the amino acid residues from positions 78-83, the amino acid residues from positions 78-82, the amino acid residues from positions 78-81, the amino acid residues from positions 78-80, the amino acid residues from positions 78-79, the amino acid residues from positions 79-83, the amino acid residues from positions 79-82, the amino acid residues from positions 79-81, the amino acid residues from positions 79-80, the amino acid residues from positions 80-83, the amino acid residues from positions 80-82, the amino acid residues from positions 80-81, the amino acid residues from positions 81-83, the amino acid residues from positions 81-82, the amino acid residues from positions 82-83, the amino acid residue at position 78, the amino acid residue at position 79, the amino acid residue at position 80, the amino acid residue at position 81, the amino acid residue at position 82, or the amino acid residue at position 83, at N-terminus of RBHB-cAg protein can be deleted or substituted with a linker. In a preferred embodiment, the linker, for example, is a flexible linker. Such a flexible linker is well known by a person skilled in the art, for example, GGGGGSGGGGTGSEFGGGGSGGGGS (SEQ ID NO: 43).

About the Difference (ii)

In a certain preferred embodiment, one or more amino acid residues (e.g. 1, 2, 3, 4, 5, 6, 7, 8, 9, 10 amino acid residues) of the amino acid residues from positions 18-27 at N-terminus of RBHBcAg protein are substituted with a human T cell epitope (e.g. an MHC I restricted human T cell epitope and/or an MHC II restricted human T cell epitope). In a certain preferred embodiment, the amino acid residues at positions 18-27, 18-26, 18-25, 18-24, 18-23, 18-22, 18-21, 18-20, 18-19, 19-27, 19-26, 19-25, 19-24, 19-23, 19-22, 19-21, 19-20, 20-27, 20-26, 20-25, 20-24, 20-23, 20-22, 20-21, 21-27, 21-26, 21-25, 21-24, 21-23, 21-22, 22-27, 22-26, 22-25, 22-24, 22-23, 23-27, 23-26, 23-25, 23-24, 24-27, 24-26, 24-25, 25-27, 25-26, 26-27, 27, 26, 25, 24, 23, 22, 21, 20, 19 or 18 at N-terminus of RBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, or 20 amino acid residues) of the amino acid residues from positions 50-69 at N-terminus of RBHB-cAg protein are substituted with a human T cell epitope (e.g. an MHC I restricted human T cell epitope and/or an MHC II restricted human T cell epitope). In a certain preferred embodiment, the amino acid residues at positions 50-69, 50-68, 50-67, 50-66, 50-65, 50-64, 50-63, 50-62, 50-61, 50-60, 50-59, 50-58, 50-57, 50-56, 50-55, 50-54, 50-53, 50-52, 50-51, 51-69, 51-68, 51-67, 51-66, 51-65, 51-64, 51-63, 51-62, 51-61, 51-60, 51-59, 51-58, 51-57, 51-56, 51-55, 51-54, 51-53, 51-52, 52-69, 52-68, 52-67, 52-66, 52-65, 52-64, 52-63, 52-62, 52-61, 52-60, 52-59, 52-58, 52-57, 52-56, 52-55, 52-54, 52-53, 53-69, 53-68, 53-67, 53-66, 53-65, 53-64, 53-63, 53-62, 53-61, 53-60, 53-59, 53-58, 53-57, 53-56, 53-55, 53-54, 54-69, 54-68, 54-67, 54-66, 54-65, 54-64, 54-63, 54-62, 54-61, 54-60, 54-59, 54-58, 54-57, 54-56, 54-57, 54-56, 54-55, 55-69, 55-68, 55-67, 55-66, 55-65, 55-64, 55-63, 55-62, 55-61, 55-60, 55-59, 55-58, 55-57, 55-56, 56-69, 56-68, 56-67, 56-66, 56-65, 56-64, 56-63, 56-62, 56-61, 56-60, 56-59, 56-58, 56-57, 57-69, 57-68, 57-67, 57-66, 57-65, 57-64, 57-63, 57-62, 57-61, 57-60, 57-59, 57-58, 58-69, 58-68, 58-67, 58-66, 58-65, 58-64, 58-63, 58-62, 58-61, 58-60, 58-59, 59-69, 59-68, 59-67, 59-66, 59-65, 59-64, 59-63, 59-62, 59-61, 59-60, 60-69, 60-68, 60-67, 60-66, 60-65, 60-64, 60-63, 60-62, 60-61, 61-69, 61-68, 61-67, 61-66, 61-65, 61-64, 61-63, 61-62, 62-69, 62-68, 62-67, 62-66, 62-65, 62-64, 62-63, 63-69, 63-68, 63-67, 63-66, 63-65, 63-64, 64-69, 64-68, 64-67, 64-66, 64-65, 65-69, 65-68, 65-67, 65-66, 66-69, 66-68, 66-67, 67-69, 67-68, 68-69, 69, 68, 67, 66, 65, 64, 63, 62, 61, 60, 59, 58, 57, 56, 55, 54, 53, 52, 51 or 50 at N-terminus of RBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, 20 or 21 amino acid residues) of the amino acid residues from positions 120-140 at N-terminus of RBHBcAg protein are substituted with a human T cell epitope (e.g. an MHC I restricted human T cell epitope and/or an MHC II restricted human T cell epitope). In a certain preferred embodiment, the amino acid residues at positions 120-140, 120-139, 120-138, 120-137, 120-136, 120-135, 120-134, 120-133, 120-132, 120-131, 120-130, 120-129, 120-128, 120-127, 120-126, 120-125, 120-124, 120-123, 120-122, 120-121, 121-140, 121-139, 121-138, 121-137, 121-136, 121-135, 121-134, 121-133, 121-132, 121-131, 121-130, 121-129, 121-128, 121-127, 121-126, 121-125, 121-124, 121-123, 121-122, 122-140, 122-139, 122-138, 122-137, 122-136, 122-135, 122-134, 122-133, 122-132, 122-131, 122-130, 122-129, 122-128, 122-127, 122-126, 122-125, 122-124, 122-123, 123-140, 123-139, 123-138, 123-137. 123-136, 123-135, 123-134, 123-133, 123-132, 123-131, 123-130, 123-129, 123-128, 123-127, 123-126, 123-125, 123-124, 124-140, 124-139, 124-138, 124-137, 124-136, 124-135, 124-134, 124-133, 124-132, 124-131, 124-130, 124-129, 124-128, 124-127, 124-126, 124-125, 125-140, 125-139, 125-138, 125-137, 125-136, 125-135, 125-134, 125-133, 125-132, 125-131, 125-130, 125-129, 125-128, 125-127, 126-140, 126-139, 126-138, 126-137, 126-136, 126-135, 126-134, 126-133, 126-132, 126-131, 126-130, 126-129, 126-128, 126-127, 127-140, 127-139, 127-138, 127-137, 127-136, 127-135, 127-134, 127-133, 127-132, 127-131, 127-130, 127-129, 127-128, 128-140, 128-139, 128-139, 128-137, 128-136, 128-135, 128-134, 128-133, 128-132, 128-131, 128-130, 128-129, 129-140, 129-139, 129-138, 129-137, 129-136, 129-135, 129-134, 129-133, 129-132, 129-131, 129-130, 130-140, 130-139, 130-138, 130-137, 130-136, 130-135, 130-134, 130-133, 130-132, 130-131, 131-140, 131-139, 131-138, 131-137, 131-136, 131-135, 131-134, 131-133, 131-132, 132-140, 132-139, 132-138, 132-137, 132-136, 132-135, 132-134, 132-133, 133-140, 133-139, 133-138, 133-137, 133-136, 133-135, 133-134, 134-140, 134-139, 134-138, 134-137, 134-136, 134-135, 135-140, 135-139, 135-138, 135-137, 135-136, 136-140, 136-139, 136-138, 136-137, 137-140, 137-139, 137-138, 138-140, 138-139, 139-140, 140, 139, 138, 137, 136, 135, 134, 133, 132, 131, 130, 129, 128, 127, 126, 125, 124, 123, 122, 121 or 120 at N-terminus of RBHBcAg protein are substituted with a human T cell epitope (e.g. an MHC I or MHC 11 restricted human T cell epitope; e.g. a human T cell epitope set forth in SEQ ID NOs: 87-89).

In a certain preferred embodiment, the RBHBcAg-T carrier comprises any one or two of the three substitutions described above. In a certain preferred embodiment, the RBHBcAg-T carrier comprises the three substitutions described above (such a polypeptide carrier is also referred to as RBHBcAg-T3 carrier below). For example, in a certain exemplary embodiment, the amino acid residues at positions 18-27 and 50-69 at N-terminus of the RBHBcAg protein are each independently substituted with a human T cell epitope (e.g. an MHC I or MHC II restricted human T cell epitope). In a certain exemplary embodiment, the amino acid residues at positions 18-27 and 120-140 at N-terminus of the RBHBcAg protein are each independently substituted with a human T cell epitope (e.g. an MHC 1 or MHC 11 restricted human T cell epitope). In a certain exemplary embodiment, the amino acid residues at positions 50-69 and 120-140 at N-terminus of the RBHBcAg protein are each independently substituted with a human T cell epitope (e.g. an MHC I or MHC II restricted human T cell epitope). In a certain exemplary embodiment, the amino acid residues at positions 18-27, 50-69 and 120-140 at N-terminus of the RBHBcAg protein are all substituted with a human T cell epitope (e.g. an MHC I or MHC 11 restricted human T cell epitope). In a certain exemplary embodiment, the amino acid residues at positions 18-27, 50-69 and 120-140 at N-terminus of the RBHBcAg protein are substituted with the human T cell epitopes set forth in SEQ ID NO: 87, 88 and 89, respectively.

About the Difference (iii)

The difference (iii) is not necessary. In other words, in the RBHBcAg-T carrier, there may or may not be a C-terminal deletion of the RBHBcAg protein. In a certain exemplary embodiment, there is not a C-terminal deletion of the RBHBcAg protein in the RBHBcAg-T carrier. In a certain exemplary embodiment, 1-40 amino acid residues are deleted at C-terminus of the RBHBcAg protein. In a certain exemplary embodiment, 1-5, 5-10, 10-15, 15-20, 20-25, 25-30, 30-35, or 35-40 amino acid residues are deleted at C-terminus of the RBHBcAg protein; for example, 1, 2, 3, 4, 5, 6, 7, 8, 9, 10, 11, 12, 13, 14, 15, 16, 17, 18 19, 20, 21, 22, 23, 24, 25, 26, 27, 28, 29, 30, 31, 32, 33, 34, 35, 36, 37, 38, 39, or 40 amino acid residues are deleted.

TBHBcAg-T Carrier

In a preferred embodiment, the TBHBcAg protein is a wild-type TBHBcAg. In a preferred embodiment, the amino acid sequence of the TBHBcAg protein is set forth in SEQ ID NO: 2.

In a preferred embodiment, the difference between the TBHBcAg-T carrier and the TBHBcAg protein comprises the following: (i) one or more contiguous amino acid residues (e.g. 1, 2, 3, 4, or 5 contiguous amino acid residues) of the amino acid residues from positions 80-84 at N-terminus of the TBHBcAg protein are deleted or substituted with a linker; (ii) one or more amino acid residues of the amino acid residues from positions 18-27, one or more amino acid residues of the amino acid residues from positions 54-73 and/or one or more amino acid residues of the amino acid residues from positions 124-144 at N-terminus of the TBHBcAg protein are each independently substituted with a human T cell epitope (e.g. a MHC I or MHC II restricted human T cell epitope); and (iii) optionally, 1-35 amino acid residues (e.g. 1-5, 5-10, 10-15, 15-20, 20-25, 25-30, or 30-35 amino acid residues) are deleted at C-terminus of the TBHBcAg protein.

About the Difference (i)

In a certain preferred embodiment, the amino acid residues at positions 80-84, amino acid residues at positions 80-83, amino acid residues at positions 80-82, amino acid residues at positions 80-81, amino acid residues at positions 81-84, amino acid residues at positions 81-83, amino acid residues at positions 81-82, amino acid residues at positions 82-84, amino acid residues at positions 82-83, amino acid residue at positions 83-84, amino acid residue at position 80, amino acid residue at position 81, amino acid residue at position 82, amino acid residue at position 83, or amino acid residue at position 84 at N-terminus of the TBHBcAg protein can be deleted or substituted with a linker. In a preferred embodiment, the linker is for example a flexible linker. Such a flexible linker is well known to those skilled in the art, for example, GGGGGSGGGGTGSEFGGGGSGGGGS (SEQ ID NO: 43).

About the Difference (ii)

In a certain preferred embodiment, one or more amino acid residues (e.g. 1, 2, 3, 4, 5, 6, 7, 8, 9, 10 amino acid residues) of the amino acid residues from positions 18-27 at N-terminus of TBHBcAg protein are substituted with a human T cell epitope (e.g. an MHC or MHC II restricted human T cell epitope). In a certain preferred embodiment, the amino acid residues at positions 18-27, 18-26, 18-25, 18-24, 18-23, 18-22, 18-21, 18-20, 18-19, 19-27, 19-26, 19-25, 19-24, 19-23, 19-22, 19-21, 19-20, 20-27, 20-26, 20-25, 20-24, 20-23, 20-22, 20-21, 21-27, 21-26, 21-25, 21-24, 21-23, 21-22, 22-27, 22-26, 22-25, 22-24, 22-23, 23-27, 23-26, 23-25, 23-24, 24-27, 24-26, 24-25, 25-27, 25-26, 26-27, 27, 26, 25, 24, 23, 22, 21, 20, 19 or 18 at N-terminus of TBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, or 20 amino acid residues) of the amino acid residues from positions 54-73 at N-terminus of TBHBcAg protein are substituted with a human T cell epitope (e.g. an MHC I or MHC II restricted human T cell epitope). In a certain preferred embodiment, the amino acid residues at positions 54-73, 54-72, 54-71, 54-70, 54-69, 54-68, 54-67, 54-66, 54-65, 54-64, 54-63, 54-62, 54-61, 54-60, 54-59, 54-58, 54-57, 54-56, 54-55, 55-73, 55-72, 55-71, 55-70, 55-69, 55-68, 55-67, 55-66, 55-65, 55-64, 55-63, 55-62, 55-61, 55-60, 55-59, 55-58, 55-57, 55-56, 56-73, 56-72, 56-71, 56-70, 56-69, 56-68, 56-67, 56-66, 56-65, 56-64, 56-63, 56-62, 56-61, 56-60, 56-59, 56-58, 56-57, 57-73, 57-72, 57-71, 57-70, 57-69, 57-68, 57-67, 57-66, 57-65, 57-64, 57-63, 57-62, 57-61, 57-60, 57-59, 57-58, 58-73, 58-72, 58-71, 58-70, 58-69, 58-68, 58-67, 58-66, 58-65, 58-64, 58-63, 58-62, 58-61, 58-60, 58-59, 59-73, 59-72, 59-71, 59-70, 59-69, 59-68, 59-67, 59-66, 59-65, 59-64, 59-63, 59-62, 59-61, 59-60, 60-73, 60-72, 60-71, 60-70, 60-69, 60-68, 60-67, 60-66, 60-65, 60-64, 60-63, 60-62, 60-61, 61-73, 61-72, 61-71, 61-70, 61-69, 61-68, 61-67, 61-66, 61-65, 61-64, 61-63, 61-62, 62-73, 62-72, 62-71, 62-70, 62-69, 62-68, 62-67, 62-66, 62-65, 62-64, 62-63, 63-73, 63-72, 63-71, 63-70, 63-69, 63-68, 63-67, 63-66, 63-65, 63-64, 64-73. 64-72, 64-71, 64-70, 64-69, 64-68, 64-67, 64-66, 64-65, 65-73, 65-72, 65-71, 65-70, 65-69, 65-68, 65-67, 65-66, 66-73, 66-72, 66-71, 66-70, 66-69, 66-68, 66-67, 67-73, 67-72, 67-71, 67-70, 67-69, 67-68, 68-73, 68-72, 68-71, 68-70, 68-69, 69-73, 69-72, 69-71, 69-70, 70-73, 70-72, 70-71, 71-73, 71-72, 72-73, 73, 72, 71, 70, 69, 68, 67, 66, 65, 64, 63, 62, 61, 60, 59, 58, 57, 56, 55 or 54 at N-terminus of TBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, 20 or 21 amino acid residues) of the amino acid residues from positions 124-144 at N-terminus of TBHBcAg protein are substituted with a human T cell epitope (e.g. an MHC I or MHC II restricted human T cell epitope). In a certain preferred embodiment, the amino acid residues at positions 124-144, 124-143, 124-142, 124-141, 124-140, 124-139, 124-138, 124-137, 124-136, 124-135, 124-134, 124-133, 124-132, 124-131, 124-130, 124-129, 124-128, 124-127, 124-126, 124-125, 125-144, 125-143, 125-142, 125-141, 125-140, 125-139, 125-138, 125-137, 125-136, 125-135, 125-134, 125-133, 125-132, 125-131, 125-130, 125-129, 125-128, 125-127, 125-126, 126-144, 126-143, 126-142, 126-141, 126-140, 126-139, 126-138, 126-137, 126-136, 126-135, 126-134, 126-133, 126-132, 126-131, 126-130, 126-129, 126-128, 126-127, 127-144, 127-143, 127-142, 127-141, 127-140, 127-139, 127-138, 127-137, 127-136, 127-135, 127-134, 127-133, 127-132, 127-131, 127-130, 127-129, 127-128, 128-144, 128-143, 128-142, 128-141, 128-140, 128-139, 128-138, 128-137, 128-136, 128-135, 128-134, 128-133, 128-132, 128-131, 128-130, 128-129, 129-144, 129-143, 129-142, 129-141, 129-140, 129-139, 129-138, 129-137, 129-136, 129-135, 129-134, 129-133, 129-132, 129-131, 129-130, 130-144, 130-143, 130-142, 130-141, 130-140, 130-139, 130-138, 130-137, 130-136, 130-135, 130-134, 130-133, 130-132, 130-131, 131-144, 131-143, 131-142, 131-141, 131-140, 131-139, 131-138, 131-137, 131-136, 131-135, 131-134, 131-133, 131-132, 132-144, 132-143, 132-142, 132-141, 132-140, 132-139, 132-138, 132-137, 132-136, 132-135, 132-134, 132-133, 133-144, 133-143, 133-142, 133-141, 133-140, 133-139, 133-138, 133-137, 133-136, 133-135, 133-134, 134-144, 134-143, 134-142, 134-141, 134-140, 134-139, 134-138, 134-137, 134-136, 134-135, 135-144, 135-143, 135-142, 135-141, 135-140, 135-139, 135-138, 135-137, 135-136, 136-144, 136-143, 136-142, 136-141, 136-140, 136-139, 136-138, 136-137, 137-144, 137-143, 137-142, 137-141, 137-140, 137-139, 137-138, 138-144, 138-143, 138-142, 138-141, 138-140, 138-139, 139-144, 139-143, 139-142, 139-141, 139-140. 140-144, 140-143, 140-142, 140-141, 141-144, 141-143, 141-142, 142-144, 142-143, 143-144, 144, 143, 142, 141, 140, 139, 138, 137, 136, 135, 134, 133, 132, 131, 130, 129, 128, 127, 126, 125 or 124 at N-terminus of TBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, the TBHBcAg-T carrier comprises any one or two of the three substitutions described above. In a certain preferred embodiment, the TBHBcAg-T carrier comprises the three substitutions described above (such a polypeptide carrier is also referred to as TBHBcAg-T3 carrier below). For example, in a certain exemplary embodiment, the amino acid residues at positions 18-27 and 54-73 at N-terminus of the TBHBcAg protein are each independently substituted with a human T cell epitope (e.g. an MHC 1 or MHC 11 restricted human T cell epitope). In a certain exemplary embodiment, the amino acid residues at positions 18-27 and 124-144 at N-terminus of the TBHBcAg protein are each independently substituted with a human T cell epitope (e.g. an MHC 1 or MHC 11 restricted human T cell epitope). In a certain exemplary embodiment, the amino acid residues at positions 54-73 and 124-144 at N-terminus of the TBHBcAg protein are each independently substituted with a human T cell epitope (e.g. an MHC I or MHC II restricted human T cell epitope). In a certain exemplary embodiment, the amino acid residues at positions 18-27, 54-73 and 124-144 at N-terminus of the TBHBcAg protein are all substituted with a human T cell epitope (e.g. an MHC I or MHC II restricted human T cell epitope). In a certain exemplary embodiment, the amino acid residues at positions 18-27, 54-73 and 124-144 at N-terminus of the TBHBcAg protein are substituted with human T cell epitopes set forth in SEQ ID NO: 87, 88 and 89, respectively.

About the Difference (iii)

The difference (iii) is not necessary. In other words, in the TBHBcAg-T carrier, there may or may not be a C-terminal deletion of the TBHBcAg protein. In a certain exemplary embodiment, there is not a C-terminal deletion of the TBHBcAg protein in the TBHBcAg-T carrier. In a certain exemplary embodiment, 1-35 amino acid residues are deleted at C-terminus of the TBHBcAg protein. In a certain exemplary embodiment, 1-5, 5-10, 10-15, 15-20, 20-25, 25-30, or 30-35 amino acid residues are deleted at the C-terminus of the TBHBcAg protein; for example, 1, 2, 3, 4, 5, 6, 7, 8, 9, 10, 11, 12, 13, 14, 15, 16, 17, 18 19, 20, 21, 22, 23, 24, 25, 26, 27, 28, 29, 30, 31, 32, 33, 34 or 35 amino acid residues are deleted.

HBHBcAg-T Carrier

In a preferred embodiment, the HBHBcAg protein is a wild-type HBHBcAg. In a preferred embodiment, the amino acid sequence of the HBHBcAg protein is set forth in SEQ ID NO: 3.

In a preferred embodiment, the difference between the HBHBcAg-T carrier and the HBHBcAg protein comprises the following: (i) one or more contiguous amino acid residues (e.g. 1, 2, 3, 4, 5 or 6 contiguous amino acid residues) of the amino acid residues from positions 78-83 at N-terminus of the HBHBcAg protein are deleted or substituted with a linker; (ii) one or more amino acid residues of the amino acid residues from positions 18-27, one or more amino acid residues of the amino acid residues from positions 50-69 and/or one or more amino acid residues of the amino acid residues from positions 120-140 at N-terminus of the HBHBcAg protein are each independently substituted with a human T cell epitope (e.g. a MHC I or MHC II restricted human T cell epitope); and (iii) optionally, 1-40 amino acid residues (e.g. 1-5, 5-10, 10-15, 15-20, 20-25, 25-30, 30-35 or 35-40 amino acid residues) are deleted at C-terminus of the HBHBcAg protein.

About the Difference (i)

In a certain preferred embodiment, the amino acid residues at positions 78-83, amino acids at positions 78-82, amino acid residues at positions 78-81, amino acid residues at positions 78-80, amino acid residues at positions 78-79, amino acid residues at positions 79-83, amino acid residues at positions 79-82, amino acid residues at positions 79-81, amino acid residues at positions 79-80, amino acid residues at positions 80-83, amino acid residues at positions 80-82, amino acid residues at positions 80-81, amino acid residues at positions 81-83, amino acid residues at positions 81-82, amino acid residues at positions 82-83, amino acid residue at position 78, amino acid residue at position 79, amino acid residue at position 80, amino acid residue at position 81, amino acid residue at position 82, or amino acid residue at position 83 at N-terminus of the HBHBcAg protein can be deleted or substituted with a linker. In a preferred embodiment, the linker is for example a flexible linker. Such a flexible linker is well known to those skilled in the art, for example.

GGGGGSGGGGTGSEFGGGGSGGGGS. (SEQ ID NO: 43)

About the Difference (ii)

In a certain preferred embodiment, one or more amino acid residues (e.g. 1, 2, 3, 4, 5, 6, 7, 8, 9, 10 amino acid residues) of the amino acid residues from positions 18-27 at N-terminus of HBHBcAg protein are substituted with a human T cell epitope (e.g. an MHC I restricted human T cell epitope and/or an MHC 11 restricted human T cell epitope). In a certain preferred embodiment, the amino acid residues at positions 18-27, 18-26, 18-25. 18-24, 18-23, 18-22, 18-21, 18-20, 18-19, 19-27, 19-26, 19-25, 19-24, 19-23, 19-22, 19-21, 19-20, 20-27, 20-26, 20-25, 20-24, 20-23, 20-22, 20-21, 21-27, 21-26, 21-25, 21-24, 21-23, 21-22, 22-27, 22-26, 22-25, 22-24, 22-23, 23-27, 23-26, 23-25, 23-24, 24-27, 24-26, 24-25, 25-27, 25-26, 26-27, 27, 26, 25, 24, 23, 22, 21, 20, 19 or 18 at N-terminus of HBHBcAg protein are substituted with a human T cell epitope (e.g. an MHC I or MHC 11 restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, or 20 amino acid residues) of the amino acid residues from positions 50-69 at N-terminus of HBHBcAg protein are substituted with a human T cell epitope (e.g. an MHC I restricted human T cell epitope and/or an MHC II restricted human T cell epitope). In a certain preferred embodiment, the amino acid residues at positions 50-69, 50-68, 50-67, 50-66, 50-65, 50-64, 50-63, 50-62, 50-61, 50-60, 50-59, 50-58, 50-57, 50-56, 50-55, 50-54, 50-53, 50-52, 50-51, 51-69, 51-68, 51-67, 51-66, 51-65, 51-64, 51-63, 51-62, 51-61, 51-60, 51-59, 51-58, 51-57, 51-56, 51-55, 51-54, 51-53, 51-52, 52-69, 52-68, 52-67, 52-66, 52-65, 52-64, 52-63, 52-62, 52-61, 52-60, 52-59, 52-58, 52-57, 52-56, 52-55, 52-54, 52-53, 53-69, 53-68, 53-67, 53-66, 53-65, 53-64, 53-63, 53-62, 53-61, 53-60, 53-59, 53-58, 53-57, 53-56, 53-55, 53-54, 54-69, 54-68, 54-67, 54-66, 54-65, 54-64, 54-63, 54-62, 54-61, 54-60, 54-59, 54-58, 54-57, 54-56, 54-57, 54-56, 54-55, 55-69, 55-68, 55-67, 55-66, 55-65, 55-64, 55-63, 55-62, 55-61, 55-60, 55-59, 55-58, 55-57, 55-56, 56-69, 56-68, 56-67, 56-66, 56-65, 56-64, 56-63, 56-62, 56-61, 56-60, 56-59, 56-58, 56-57, 57-69, 57-68, 57-67, 57-66, 57-65, 57-64, 57-63, 57-62, 57-61, 57-60, 57-59, 57-58, 58-69, 58-68, 58-67, 58-66, 58-65, 58-64, 58-63, 58-62, 58-61, 58-60, 58-59, 59-69, 59-68, 59-67, 59-66, 59-65, 59-64, 59-63, 59-62, 59-61, 59-60, 60-69, 60-68, 60-67, 60-66, 60-65, 60-64, 60-63, 60-62, 60-61, 61-69, 61-68, 61-67, 61-66, 61-65, 61-64, 61-63, 61-62, 62-69, 62-68, 62-67, 62-66, 62-65, 62-64, 62-63, 63-69, 63-68, 63-67, 63-66, 63-65, 63-64, 64-69, 64-68, 64-67, 64-66, 64-65, 65-69, 65-68, 65-67, 65-66, 66-69, 66-68, 66-67, 67-69, 67-68, 68-69, 69, 68, 67, 66, 65, 64, 63, 62, 61, 60, 59, 58, 57, 56, 55, 54, 53, 52, 51 or 50 at N-terminus of HBHBcAg protein are substituted with a human T cell epitope (e.g. an MHC 1 or MHC 11 restricted human T cell epitope; e.g. a human T cell epitope set forth in SEQ ID NOs: 87-89).

In a certain preferred embodiment, one or more amino acid residues (e.g. 1, 2, 3, 4, 5, 6, 7, 8, 9, 10, 11, 12, 13, 14, 15, 16, 17, 18, 19, 20 or 21 amino acid residues) of the amino acid residues from positions 120-140 at N-terminus of HBHBcAg protein are substituted with a human T cell epitope (e.g. an MHC I restricted human T cell epitope and/or an MHC II restricted human T cell epitope). In a certain preferred embodiment, the amino acid residues at positions 120-140, 120-139, 120-138, 120-137, 120-136, 120-135, 120-134, 120-133, 120-132, 120-131, 120-130, 120-129, 120-128, 120-127, 120-126, 120-125, 120-124, 120-123, 120-122, 120-121, 121-140, 121-139, 121-138, 121-137, 121-136, 121-135, 121-134, 121-133, 121-132, 121-131, 121-130, 121-129, 121-128, 121-127, 121-126, 121-125, 121-124, 121-123, 121-122, 122-140, 122-139, 122-138, 122-137, 122-136, 122-135, 122-134, 122-133, 122-132, 122-131, 122-130, 122-129, 122-128, 122-127, 122-126, 122-125, 122-124, 122-123, 123-140, 123-139, 123-138, 123-137, 123-136, 123-135, 123-134, 123-133, 123-132, 123-131, 123-130, 123-129, 123-128, 123-127, 123-126, 123-125, 123-124, 124-140, 124-139, 124-138, 124-137, 124-136, 124-135, 124-134, 124-133, 124-132, 124-131, 124-130, 124-129, 124-128, 124-127, 124-126, 124-125, 125-140, 125-139, 125-138, 125-137, 125-136, 125-135, 125-134, 125-133, 125-132, 125-131, 125-130, 125-129, 125-128, 125-127, 126-140, 126-139, 126-138, 126-137, 126-136, 126-135, 126-134, 126-133, 126-132, 126-131, 126-130, 126-129, 126-128, 126-127, 127-140, 127-139, 127-138, 127-137, 127-136, 127-135, 127-134, 127-133, 127-132, 127-131, 127-130, 127-129, 127-128, 128-140, 128-139, 128-139, 128-137, 128-136, 128-135, 128-134, 128-133, 128-132, 128-131, 128-130, 128-129, 129-140, 129-139, 129-138, 129-137, 129-136, 129-135, 129-134, 129-133, 129-132, 129-131, 129-130, 130-140, 130-139, 130-138, 130-137, 130-136, 130-135, 130-134, 130-133, 130-132, 130-131, 131-140, 131-139, 131-138, 131-137, 131-136, 131-135, 131-134, 131-133, 131-132, 132-140, 132-139, 132-138, 132-137, 132-136, 132-135, 132-134, 132-133, 133-140, 133-139, 133-138, 133-137, 133-136, 133-135, 133-134, 134-140, 134-139, 134-138, 134-137, 134-136, 134-135, 135-140, 135-139, 135-138, 135-137, 135-136, 136-140, 136-139, 136-138, 136-137, 137-140, 137-139, 137-138, 138-140, 138-139, 139-140, 140, 139, 138, 137, 136, 135, 134, 133, 132, 131, 130, 129, 128, 127, 126, 125, 124, 123, 122, 121 or 120 at N-terminus of HBHBcAg protein are substituted with a human T cell epitope (e.g. an MHC I or MHC II restricted human T cell epitope; e.g. a human T cell epitope set forth in SEQ ID NOs: 87-89).

In a certain preferred embodiment, the HBHBcAg-T carrier comprises any one or two of the three substitutions described above. In a certain preferred embodiment, the HBHBcAg-T carrier comprises the three substitutions described above (such a polypeptide carrier is also referred to as HBHBcAg-T3 carrier below). For example, in a certain exemplary embodiment, the amino acid residues at positions 18-27 and 50-69 at N-terminus of the HBHBcAg protein are each independently substituted with a human T cell epitope (e.g. an MHC I or MHC II restricted human T cell epitope). In a certain exemplary embodiment, the amino acid residues at positions 18-27 and 120-140 at N-terminus of the HBHBcAg protein are each independently substituted with a human T cell epitope (e.g. an MHC I or MHC II restricted human T cell epitope). In a certain exemplary embodiment, the amino acid residues at positions 50-69 and 120-140 at N-terminus of the HBHBcAg protein are each independently substituted with a human T cell epitope (e.g. an MHC I or MHC II restricted human T cell epitope). In a certain exemplary embodiment, the amino acid residues at positions 18-27, 50-69 and 120-140 at N-terminus of the HBHBcAg protein are all substituted with a human T cell epitope (e.g. an MHC I or MHC II restricted human T cell epitope). In a certain exemplary embodiment, the amino acid residues at positions 18-27, 50-69 and 120-140 at N-terminus of the HBHBcAg protein are substituted with human T cell epitopes set forth in SEQ ID NO: 87, 88 and 89, respectively.

About the Difference (iii)

The difference (iii) is not necessary. In other words, in the HBHBcAg-T carrier, there may or may not be a C-terminal deletion of the HBHBcAg protein. In a certain exemplary embodiment, there is not a C-terminal deletion of the HBHBcAg protein in the HBHBcAg-T carrier. In a certain exemplary embodiment, 1-40 amino acid residues are deleted at C-terminus of the HBHBcAg protein. In a certain exemplary embodiment, 1-5, 5-10, 10-15, 15-20, 20-25, 25-30, 30-35 or 35-40 amino acid residues are deleted at the C-terminus of the HBHBcAg protein, for example, 1, 2, 3, 4, 5, 6, 7, 8, 9, 10, 11, 12, 13, 14, 15, 16, 17, 18 19, 20, 21, 22, 23, 24, 25, 26, 27, 28, 29, 30, 31, 32, 33, 34, 35, 36, 37, 38, 39 or 40 amino acid residues are deleted.

As known by a person skilled in the art, introduction of a restriction enzyme cleavage site is particularly advantageous. Therefore, in a preferred embodiment, in the nucleic acid molecule of the invention, a restriction enzyme cleavage site is introduced at a position of nucleotides encoding the one or more amino acid residues (e.g. the amino acid residues from positions 78-83 at N-terminus of RBHBcAg protein, the amino acid residues from positions 80-84 at N-terminus of TBHBcAg protein and the amino acid residues from positions 78-83 at N-terminus of HBHBcAg protein) that are deleted. In a preferred embodiment, in the nucleic acid molecule of the invention, a restriction enzyme cleavage site is introduced in the nucleotide sequence encoding the linker and/or at either or both of the termini thereof. In a preferred embodiment, one or more restriction enzyme cleavage sites are introduced in the nucleic acid molecule of the invention and/or at either or both of the termini thereof. A variety of restriction enzyme cleavage sites are known by a person skilled in the art, including, but not limited to, enzyme cleavage sites recognized by restriction enzymes such as EcoR I, BamH I, Hind II, Hind III, Hpa I, Hpa II, Mbo I, and Mbo II.

In a preferred embodiment, the variant has an identity of at least 90%, e.g., an identify of at least 91%, at least 92%, at least 93%, at least 94%, at least 95%, at least 96%, at least 97%, at least 98%, or at least 99%, to the nucleotide sequence encoding the polypeptide carrier.

In a preferred embodiment, the variant is capable of hybridizing to the nucleotide sequence encoding the polypeptide carrier under a stringent condition. In a preferred embodiment, the variant is capable of hybridizing to the nucleotide sequence encoding the polypeptide carrier under a high stringent condition.

In a preferred embodiment, the polypeptide carrier has an amino acid sequence selected from SEQ ID NO: 4-9 and 75-80.

In a preferred embodiment, the nucleic acid molecule comprises a nucleotide sequence selected from SEQ ID NO: 12-17 and 81-86.

In a preferred embodiment, the nucleic acid molecule is used for insertion of a nucleotide sequence encoding a target polypeptide. For example, the nucleotide sequence encoding a target polypeptide is inserted at a position of nucleotides encoding the one or more amino acid residues (e.g. the amino acid residues from positions 78-83 at N-terminus of RBHBcAg protein, the amino acid residues from positions 80-84 at N-terminus of TBHBcAg protein and the amino acid residues from positions 78-83 at N-terminus of HBHBcAg protein) that are deleted, or is inserted in the nucleotide sequence encoding the linker or at either or both of the termini thereof. In a preferred embodiment, in an in-frame manner, the nucleotide sequence encoding a target polypeptide is inserted into the nucleotide sequence encoding the polypeptide carrier. In a preferred embodiment, by virtue of a restriction enzyme cleavage site, the nucleotide sequence encoding a target polypeptide is inserted into the nucleotide sequence encoding the polypeptide carrier.

In a preferred embodiment, the nucleic acid molecule further comprises a nucleotide sequence encoding a target polypeptide, wherein the target polypeptide is heterologous relative to the polypeptide carrier, and the nucleotide sequence encoding the target polypeptide is inserted at a position of nucleotides encoding the one or more amino acid residues (e.g. the amino acid residues from positions 78-83 at N-terminus of RBHBcAg protein, the amino acid residues from positions 80-84 at N-terminus of TBHBcAg protein and the amino acid residues from positions 78-83 at N-terminus of HBHBcAg protein) that are deleted, or is inserted in the nucleotide sequence encoding the linker or at either or both of the termini thereof. In a preferred embodiment, in an in-frame manner, the nucleotide sequence encoding the target polypeptide is inserted in the nucleotide sequence encoding the polypeptide carrier. In a preferred embodiment, by virtue of a restriction enzyme cleavage site, the nucleotide sequence encoding the target polypeptide is inserted in the nucleotide sequence encoding the polypeptide carrier.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV).

In a preferred embodiment, the target polypeptide comprises or is HBsAg of human HBV or an epitope peptide comprising an epitope (e.g., a linear epitope) of HBsAg. In a preferred embodiment, the polypeptide carrier is RBHBcAg carrier or RBHBcAg-T carrier, and the epitope peptide comprises or is an antigenic epitope from HIV, PDL1 or HBV (particularly human HBV) (e.g., an epitope (e.g., a linear epitope) of HBsAg from human HBV). In a preferred embodiment, the polypeptide carrier is TBHBcAg carrier or TBHBcAg-T carrier, and the epitope peptide comprises or is an antigenic epitope from HIV, PDL1 or HBV (particularly human HBV) (e.g., an epitope (e.g., a linear epitope) of HBsAg from human HBV). In a preferred embodiment, the polypeptide carrier is HBHBcAg carrier or HBHBcAg-T carrier, and the epitope peptide comprises or is an antigenic epitope from HIV, PDL1 or HBV (particularly human HBV) (e.g., an epitope (e.g., a linear epitope) of HBsAg from human HBV).

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of said GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the nucleic acid molecule comprises or consists of a nucleotide sequence encoding an amino acid sequence selected from SEQ ID NO: 23-40, 69-74 and 90-96.

In another aspect, the invention relates to a vector comprising the nucleic acid molecule of the invention as defined above.

Vectors for insertion of a target polynucleotide (e.g., the nucleic acid molecule of the invention) are well known in the art, including, but not limited to cloning vectors and expression vectors. In a preferred embodiment, the vector of the invention may be a eukaryotic expression vector or a prokaryotic expression vector. In a preferred embodiment, the vector of the invention is, for example, plasmid, cosmid, or phage, etc.

In another aspect, the invention further relates to a host cell comprising the nucleic acid molecule or vector. Such host cells include, but are not limited to, prokaryotic cells such as *E. coli* cells, and eukaryotic cells such as yeast cells, insect cells, plant cells and animal cells (such as mammalian cells, e.g., mouse cells, human cells, etc.). The host cell of the invention may also be a cell line, such as 293T cell.

In another aspect, the invention relates to a method for presenting a target polypeptide, comprising:

(1) inserting a nucleotide sequence encoding the target polypeptide into the nucleic acid molecule of the invention (particularly, into the nucleotide sequence encoding the polypeptide carrier), so as to obtain a nucleic acid molecule encoding a recombinant protein; and (2) expressing the nucleic acid molecule encoding the recombinant protein in the step (1) to produce a recombinant protein.

In a preferred embodiment, the target polypeptide is heterologous relative to the polypeptide carrier. In a preferred embodiment, the nucleotide sequence encoding the target polypeptide is inserted at a position of nucleotides encoding the one or more amino acid residues (e.g. the amino acid residues from positions 78-83 at N-terminus of RBHBcAg protein, the amino acid residues from positions 80-84 at N-terminus of TBHBcAg protein and the amino acid residues from positions 78-83 at N-terminus of HBHBcAg protein) that are deleted, or is inserted in the nucleotide sequence encoding the linker or at either or both of the termini thereof. In a preferred embodiment, in an in-frame manner, the nucleotide sequence encoding the target polypeptide is inserted in the nucleotide sequence encoding the polypeptide carrier. In a preferred embodiment, by virtue of a restriction enzyme cleavage site, the nucleotide sequence encoding the target polypeptide is inserted in the nucleotide sequence encoding the polypeptide carrier.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV).

In a preferred embodiment, the target polypeptide comprises or is HBsAg of human HBV or an epitope peptide comprising an epitope (e.g., a linear epitope) of HBsAg. In a preferred embodiment, the polypeptide carrier is RBHBcAg carrier or RBHBcAg-T carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is TBHBcAg carrier or TBHBcAg-T carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is HBHBcAg carrier or HBHBcAg-T carrier, and the epitope peptide comprises or is an antigenic epitope from HIV, PDL1 or HBV (particularly human HBV). e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of said GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the nucleic acid molecule encoding the recombinant protein comprises or consists of a nucleotide sequence encoding an amino acid sequence selected from SEQ ID NO: 23-40, 69-74 and 90-96.

In another aspect, the invention relates to a recombinant protein, comprising a polypeptide carrier and a target polypeptide, wherein, the polypeptide carrier has the same meanings as defined above, and, the target polypeptide is inserted in the polypeptide carrier.

In a preferred embodiment, the target polypeptide is inserted at a position of the one or more amino acid residues (e.g. the amino acid residues from positions 78-83 at N-terminus of RBHBcAg protein, the amino acid residues from positions 80-84 at N-terminus of TBHBcAg protein and the amino acid residues from positions 78-83 at N-terminus of HBHBcAg protein) that are deleted, or inserted in the linker or at either or both of the termini thereof.

In a preferred embodiment, the target polypeptide comprises or is an antigen or an epitope peptide comprising an antigenic epitope. In a preferred embodiment, the target polypeptide is an epitope peptide, for example, an epitope peptide comprising an antigenic epitope from HIV, PDL1 or HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier or RBHBcAg-T carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is TBHBcAg carrier or TBHBcAg-T carrier, and the epitope peptide comprises or is an antigenic epitope from HIV, PDL1 or HBV (particularly human HBV), e.g., an epitope (e.g., a linear epitope) of HBsAg from human HBV. In a preferred embodiment, the polypeptide carrier is HBHBcAg carrier or HBHBcAg-T carrier, and the epitope peptide comprises or is an antigenic epitope from HIV, PDL1 or HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide comprises or is HIV GP120 protein or an epitope peptide comprising an epitope (e.g., a linear epitope) of GP120 protein. In a preferred embodiment, the epitope peptide comprises or is the amino acids from positions 361-375 of GP120 protein. In a preferred embodiment, the target polypeptide comprises or is human PD-L1 protein or an epitope peptide comprising an epitope (e.g., a linear epitope) of human PD-L1 protein. In a preferred embodiment, the epitope peptide comprises or is the amino acids from positions 147-160 of human PD-L1 protein.

In a preferred embodiment, the target polypeptide has an amino acid sequence selected from SEQ ID NO: 20-22 and 60-62. In a preferred embodiment, the polypeptide carrier has an amino acid sequence selected from SEQ ID NO: 4-9 and 75-80. In a preferred embodiment, the recombinant protein comprises or consists of an amino acid sequence selected from SEQ ID NO: 23-40, 69-74 and 90-96.

In another aspect, the invention relates to a virus-like particle, comprising or consisting of the recombinant protein of the invention.

In another aspect, the invention relates to a pharmaceutical composition (e.g., a vaccine), comprising the recombinant protein of the invention or the virus-like particle of the invention, and optionally, one or more pharmaceutically acceptable vehicles or excipients (e.g., adjuvants). In a preferred embodiment, the recombinant protein of the invention or the virus-like particle of the invention is present in an effective amount in the pharmaceutical composition. For example, the pharmaceutical composition of the invention may comprise the recombinant protein or the virus-like particle in an amount effective for the prevention or treatment of HBV infection or a disease associated with HBV infection (e.g., hepatitis B).

In another aspect, the invention relates to a method for preventing or treating HBV infection or a disease associated with HBV infection (e.g., hepatitis B), comprising administering to a subject in need thereof the recombinant protein or virus-like particle or pharmaceutical composition of the invention, wherein the target polypeptide comprises an antigenic epitope from HBV (particularly human HBV). In a preferred embodiment, the target polypeptide is an epitope peptide comprising an antigenic epitope from HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier or RBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier or TBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier or HBHBcAg-T carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of said HBsAg protein. In a preferred embodiment, the HBV is selected from HBV genotype A, B.

C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40, 69-74 and 90-96.

In a preferred embodiment, the recombinant protein or virus-like particle or pharmaceutical composition of the invention is administered in an amount effective for preventing or treating HBV infection or a disease associated with HBV infection (e.g., hepatitis B).

In another aspect, the invention relates to use of the recombinant protein or virus-like particle in the manufacture of a medicament for preventing or treating HBV infection or a disease associated with HBV infection (e.g., hepatitis B), wherein the target polypeptide comprises an antigenic epitope from HBV (particularly human HBV). In a preferred embodiment, the target polypeptide is an epitope peptide comprising an antigenic epitope from HBV (particularly human HBV). In a preferred embodiment, the target polypeptide comprises or is HBsAg of human HBV or an epitope peptide comprising an epitope (e.g., a linear epitope) of HBsAg.

In a preferred embodiment, the polypeptide carrier is RBHBcAg carrier or RBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier or TBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier or HBHBcAg-T carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40, 69-74 and 90-96.

In a preferred embodiment, the polypeptide carrier is RBHBcAg carrier or RBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is TBHBcAg carrier or TBHBcAg-T carrier, and the epitope peptide comprises or is an antigenic epitope from HBV (particularly human HBV), e.g., an epitope (e.g., a linear epitope) of HBsAg from human HBV. In a preferred embodiment, the polypeptide carrier is HBHBcAg carrier or HBHBcAg-T carrier, and the epitope peptide comprises or is an antigenic epitope from HBV (particularly human HBV), e.g., an epitope (e.g., a linear epitope) of HBsAg from human HBV.

In a preferred embodiment, the target polypeptide comprises or is HBsAg protein of human HBV or an epitope peptide comprising an epitope (e.g., a linear epitope) of HBsAg protein. In a preferred embodiment, the HBV is selected from HBV genotype A, B, C and D. In a preferred embodiment, the epitope of HBsAg protein is the amino acids from positions 113-135 of HBsAg protein.

In a preferred embodiment, the target polypeptide has an amino acid sequence selected from SEQ ID NO: 22 and 60-62. In a preferred embodiment, the recombinant protein comprises or consists of an amino acid sequence selected from SEQ ID NO: 35-40, 69-74 and 90-96.

In another aspect, the invention relates to a method for preventing or treating HIV infection or a disease associated with HIV infection (e.g., AIDS), comprising administering to a subject in need thereof the recombinant protein or virus-like particle or pharmaceutical composition of the invention, wherein the target polypeptide comprises an antigenic epitope of HIV. In a preferred embodiment, the target polypeptide is an epitope peptide comprising an antigenic epitope from HIV. In a preferred embodiment, the target polypeptide comprises or is HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In a preferred embodiment, the recombinant protein or virus-like particle or pharmaceutical composition of the invention is administered in an amount effective for preventing or treating HIV infection or a disease associated with HIV infection (e.g., AIDS).

In another aspect, the invention relates to use of the recombinant protein or virus-like particle of the invention in the manufacture of a medicament for preventing or treating HIV infection or a disease associated with HIV infection (e.g., AIDS), wherein the target polypeptide comprises an antigenic epitope from HIV. In a preferred embodiment, the target polypeptide is an epitope peptide comprising an antigenic epitope from HIV. In a preferred embodiment, the target polypeptide comprises or is selected from HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In another aspect, the invention relates to the recombinant protein or virus-like particle or pharmaceutical composition of the invention, for use in the prevention or treatment of HIV infection or a disease associated with HIV infection (e.g., AIDS), wherein the target polypeptide comprises an antigenic epitope from HIV. In a preferred embodiment, the target polypeptide is an epitope peptide comprising an antigenic epitope from HIV. In a preferred embodiment, the target polypeptide comprises or is HIV GP120 protein or an epitope peptide comprising an epitope (e.g., a linear epitope) of GP120 protein.

In a preferred embodiment, the epitope peptide comprises or is the amino acids from positions 361-375 of GP120 protein. In a preferred embodiment, the target polypeptide has an amino acid sequence set forth in SEQ ID NO: 20. In a preferred embodiment, the recombinant protein comprises or consists of an amino acid sequence selected from SEQ ID NO: 23-28.

In another aspect, the invention relates to a method for preventing or treating cancer (e.g., non-small cell lung cancer), comprising administering to a subject in need thereof the recombinant protein or virus-like particle or pharmaceutical composition of the invention, wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In a preferred embodiment, the recombinant protein or virus-like particle or pharmaceutical composition of the invention is administered in an amount effective for preventing or treating cancer (e.g., non-small cell lung cancer).

In another aspect, the invention relates to use of the recombinant protein or virus-like particle in the manufacture of a medicament for preventing or treating cancer (e.g., non-small cell lung cancer), wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In another aspect, the invention relates to the recombinant protein or virus-like particle or pharmaceutical composition, for use in the prevention or treatment of cancer (e.g., non-small cell lung cancer), wherein the target polypeptide comprises an antigenic epitope of human PD-L1 protein. In a preferred embodiment, the target polypeptide is an epitope peptide comprising an antigenic epitope of human PD-L1 protein. In a preferred embodiment, the target polypeptide comprises or is human PD-L1 protein or an epitope peptide comprising an epitope (e.g., a linear epitope) of human PD-L1 protein.

In a preferred embodiment, the epitope peptide comprises or is the amino acids from positions 147-160 of human PD-L1 protein. In a preferred embodiment, the target polypeptide has an amino acid sequence set forth in SEQ ID NO: 21. In a preferred embodiment, the recombinant protein comprises or consists of an amino acid sequence selected from SEQ ID NO: 29-34.

In another aspect, the invention relates to a polynucleotide encoding the recombinant protein and a vector comprising the polynucleotide.

Vectors for insertion of a target polynucleotide (e.g., the nucleic acid molecule of the invention) are well known in the art, including, but not limited to cloning vectors and expression vectors. In a preferred embodiment, the vector of the invention may be a eukaryotic expression vector or a prokaryotic expression vector. In a preferred embodiment, the vector of the invention is, for example, plasmid, cosmid, or phage, etc.

In another aspect, the invention further relates to a host cell comprising the polynucleotide or vector. Such host cells include, but are not limited to, prokaryotic cells such as *E. coli* cells, and eukaryotic cells such as yeast cells, insect cells, plant cells and animal cells (such as mammalian cells, e.g., mouse cells, human cells, etc.). The host cell of the invention may also be a cell line, such as 293T cell.

In another aspect, the invention further relates to a method for preparing the recombinant protein, comprising culturing the host cell of the invention under the condition suitable for expressing the recombinant protein, and, recovering the recombinant protein.

Definitions and Explanations of the Relevant Terms in the Invention

In the invention, unless otherwise specified, the scientific and technical terms used herein have the meanings as generally understood by a person skilled in the art. Moreover, the laboratory operating steps of cell culture, molecular genetics, nucleic acid chemistry and immunology used herein are the routine steps widely used in the corresponding fields. In addition, in order to better understand the invention, the definitions and explanations of the relevant terms are provided as follows.

As used herein, the terms "roundleaf bat HBV core antigen protein (RBHBcAg)" and "RBHBcAg protein" refer to a core antigen protein from roundleaf bat HBV (RBHBV), which is well known by a person skilled in the art (see, for example, NCBI GENBANK Accession Number: KC790373.1).

As used herein, when the amino acid sequence of RBHBcAg protein is mentioned, it is described by reference to the sequence set forth in SEQ ID NO: 1. For example, the expression "amino acid residues from positions 78-83 at N-terminus of RBHBcAg protein" refers to amino acid residues from positions 78-83 of the polypeptide set forth in SEQ ID NO: 1. However, a person skilled in the art understands that mutations or variations (including, but not limited to, substitution, deletion and/or addition, e.g., RBHBcAg protein of a different genotype or gene subtype) may occur naturally in or be introduced artificially into the amino acid sequence of RBHBcAg protein without affecting the biological properties thereof. Therefore, in the invention, the term "RBHBcAg protein" intends to include all such sequences, including the sequence set forth in SEQ ID NO: 1 and its natural or artificial variants. In addition, when sequence fragments of RBHBcAg protein are described, they include not only the sequence fragments of SEQ ID NO: 1, but also the corresponding sequence fragments of its natural or artificial variants. For example, the expression "amino acid residues from positions 78-83 at N-terminus of RBHBcAg protein" includes amino acid residues from positions 78-83 of SEQ ID NO: 1, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the term "wild type RBHBcAg" refers to a naturally occurring core antigen protein in roundleaf bat HBV.

As used herein, the term "RBHBcAg carrier" and "RBHBcAg-T carrier" refers to a polypeptide carrier derived from RBHBcAg protein. As described in detail above, the difference between RBHBcAg carrier and RBHBcAg protein comprises the following: (a) one or more amino acid residues of the amino acid residues from positions 78-83 at N-terminus of RBHBcAg protein are deleted or substituted with a linker; and (b) optionally, 1-40 amino acid residues are deleted at C-terminus of RBHBcAg protein. The difference between RBHBcAg-T carrier and RBHBcAg protein comprises the following: (a) one or more amino acid residues in the amino acid residues from positions 78-83 at N-terminus of RBHBcAg protein are deleted or substituted with a linker; (b) one or more amino acid residues of the amino acid residues from positions 18-27, one or more amino acid residues of the amino acid residues from positions 50-69 and/or one or more amino acid residues of the amino acid residues from positions 120-140 at N-terminus of RBHBcAg protein are each independently substituted with a human T cell epitope; and (c) optionally, 1-40 amino acid residues are deleted at C-terminus of RBHBcAg protein.

As used herein, the terms "tent-making bat HBV core antigen (TBHBcAg)" and "TBHBcAg protein" refer to a core antigen protein from tent-making bat HBV (TBHBV), which is well known by a person skilled in the art (see, for example, NCBI GENBANK Accession Number: KC790378.1).

As used herein, when the amino acid sequence of TBHBcAg protein is mentioned, it is described by reference to the sequence set forth in SEQ ID NO: 2. For example, the expression "amino acid residues from positions 80-84 at N-terminus of TBHBcAg protein" refers to amino acid residues from positions 80-84 of the polypeptide set forth in SEQ ID NO: 2. However, a person skilled in the art understands that mutations or variations (including, but not limited to, substitution, deletion and/or addition, e.g., TBHBcAg protein of a different genotype or gene subtype) may occur naturally in or be introduced artificially into the amino acid sequence of TBHBcAg protein without affecting the biological properties thereof. Therefore, in the invention, the term "TBHBcAg protein" intends to include all such sequences, including the sequence set forth in SEQ ID NO: 2 and its natural or artificial variants. In addition, when sequence fragments of TBHBcAg protein are described, they include not only the sequence fragments of SEQ ID NO: 2, but also the corresponding sequence fragments of its natural or artificial variants. For example, the expression "amino acid residues from positions 80-84 at N-terminus of TBHBcAg protein" includes amino acid residues from positions 80-84 of SEQ ID NO: 2, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the term "wile type TBHBcAg" refers to a naturally occurring core antigen protein in tent-making bat HBV.

As used herein, the term "TBHBcAg carrier" and "TBHBcAg-T carrier" refers to a polypeptide carrier derived from TBHBcAg protein. As described in detail above, the difference between TBHBcAg carrier and TBHBcAg protein comprises the following: (a) one or more amino acid residues of the amino acid residues from positions 80-84 at N-terminus of TBHBcAg protein are deleted or substituted with a linker; and (b) optionally, 1-35 amino acid residues are deleted at C-terminus of TBHBcAg protein. The difference between the TBHBcAg-T carrier and the TBHBcAg protein comprises the following: (a) one or more amino acid residues in the amino acid residues from positions 80-84 at N-terminus of the TBHBcAg protein are deleted or substituted with a linker; (b) one or more amino acid residues of the amino acid residues from positions 18-27, one or more amino acid residues of the amino acid residues from positions 54-73 and/or one or more amino acid residues of the amino acid residues from positions 124-144 at N-terminus of the TBHBcAg protein are each independently substituted with a human T cell epitope; and (c) optionally, 1-35 amino acid residues are deleted at C-terminus of the TBHBcAg protein.

As used herein, the terms "horseshoe bat HBV core antigen (HBHBcAg)" and "HBHBcAg protein" refer to a core antigen protein from horseshoe bat HBV (HBHBV), which is well known by a person skilled in the art (see, for example, NCBI GENBANK Accession Number: KC790377.1).

As used herein, when the amino acid sequence of HBHBcAg protein is mentioned, it is described by reference to the sequence set forth in SEQ ID NO: 3. For example, the expression "amino acid residues from positions 78-83 at N-terminus of HBHBcAg protein" refers to amino acid residues from positions 78-83 of the polypeptide set forth in SEQ ID NO: 3. However, a person skilled in the art understands that mutations or variations (including, but not limited to, substitution, deletion and/or addition, e.g., HBHBcAg protein of a different genotype or gene subtype) may occur naturally in or be introduced artificially into the amino acid sequence of HBHBcAg protein without affecting the biological properties thereof. Therefore, in the invention, the term "HBHBcAg protein" intends to include all such sequences, including the sequence set forth in SEQ ID NO: 3 and its natural or artificial variants. In addition, when sequence fragments of HBHBcAg protein are described, they include not only the sequence fragments of SEQ ID NO: 3, but also the corresponding sequence fragments of its natural or artificial variants. For example, the expression "amino acid residues from positions 78-83 at N-terminus of HBHBcAg protein" includes amino acid residues from positions 78-83 of SEQ ID NO: 3, and the corresponding fragments of its variants (natural or artificial variants).

According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the term "wile type HBHBcAg" refers to a naturally occurring core antigen protein in horseshoe bat HBV.

As used herein, the term "HBHBcAg carrier" and "HBHBcAg-T carrier" refers to a polypeptide carrier derived from HBHBcAg protein. As described in detail above, the difference between HBHBcAg carrier and HBHBcAg protein comprises the following: (a) one or more amino acid residues of the amino acid residues from positions 78-83 at N-terminus of HBHBcAg protein are deleted or substituted with a linker; and (b) optionally, 1-40 amino acid residues are deleted at C-terminus of HBHBcAg protein. The difference between the HBHBcAg-T carrier and the HBHBcAg protein comprises the following: (a) one or more amino acid residues in the amino acid residues at positions 78-83 at N-terminus of the HBHBcAg protein are deleted or substituted with a linker; (b) one or more amino acid residues of the amino acid residues from positions 18-27, one or more amino acid residues of the amino acid residues from positions 50-69 and/or one or more amino acid residues of the amino acid residues from positions 120-140 at N-terminus of the HBHBcAg protein are each independently substituted with a human T cell epitope; and (c) optionally, 1-40 amino acid residues are deleted at C-terminus of the HBHBcAg protein.

As used herein, the terms "human HBV HBcAg" and "Hu-HBcAg" refer to the core antigen protein of human hepatitis B virus, which is well known by a person skilled in the art (see, for example, NCBI GENBANK Accession Number: AAO63517.1). As used herein, when the amino acid sequence of human HBV HBcAg is mentioned, it is described by the sequence set forth in NCBI GENBANK Accession Number: AAO63517.1.

As used herein, the terms "human HBV HBsAg" and "Hu-HBsAg" refer to the surface antigen protein of human hepatitis B virus, which is well known by a person skilled in the art (see, for example, NCBI GENBANK Accession Number: AAF24729, 1).

As used herein, when the amino acid sequence of human HBV HBsAg is mentioned, it is described by reference to the sequence set forth in SEQ ID NO: 44 (i.e., NCBI GENBANK Accession Number: AAF24729.1). For example, the expression "amino acid residues from positions 113-135 of HBsAg protein" refers to amino acid residues from positions 113-135 of the polypeptide set forth in SEQ ID NO: 44. However, a person skilled in the art understands that mutations or variations (including, but not limited to, substitution, deletion and/or addition, e.g., HBsAg protein of a different genotype or gene subtype) may occur naturally in or be introduced artificially into the amino acid sequence of HBsAg protein without affecting the biological properties thereof. Therefore, in the invention, the term "HBsAg protein" intends to include all such sequences, including the sequence set forth in SEQ ID NO: 44 and its natural or artificial variants. In addition, when sequence fragments of HBsAg protein are described, they include not only the sequence fragments of SEQ ID NO: 44, but also the corresponding sequence fragments of its natural or artificial variants. For example, the expression "amino acid residues from positions 113-135 of HBsAg protein" includes amino acid residues from positions 113-135 of SEQ ID NO: 44, and the corresponding fragments of its variants (natural or artificial variants). According to the invention, the expression "corresponding sequence fragments" or "corresponding fragments" refers to the fragments that are located at equal positions of sequences when the sequences are subjected to optimized alignment, namely, the sequences are aligned to obtain a highest percentage of identity.

As used herein, the expression "Y amino acid residues deleted at C-terminus of X protein" means that the last Y amino acid residues at C-terminus of X protein are completely deleted. For example, the expression "1-40 amino acid residues deleted at C-terminus of RBHBcAg protein" means that the last 1-40 amino acid residues at C-terminus of RBHBcAg protein are completely deleted.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the biological activity of a protein or polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having D-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the term "hybridization" refers to the process of forming a double stranded nucleic acid by annealing two single-stranded nucleic acid molecules having complementary sequences based on the principle of complementary base pairing under certain conditions (e.g. suitable temperature, ionic strength, etc.). Nucleic acid hybridization may occur between DNA-DNA, as well as between DNA-RNA or RNA-RNA, as long as they have complementary sequences for base pairing. With respect to the further detailed description of nucleic acid hybridization, please refer to, for example, Henegariu O et al., (1999). "Custom fluorescent-nucleotide synthesis as an alternative method for nucleic acid labeling", Nature Biotechnology 18:345-348; Ezaki T et al., 1989. Fluorometric Deoxyribonucleic Acid-Deoxyribonucleic Acid Hybridization in Microdilution Wells as an Alternative to Membrane Filter Hybridization in which Radioisotopes Are Used to Determine Genetic Relatedness among Bacterial Strains. Int. J. of Systemic Bacteriology 29 (3): 224-229; and Herrington C et al., 1998. PCR 3: PCR in situ hybridization: a practical approach, Volume 3. Oxford: Oxford University Press.

In order to ensure the specificity of nucleic acid hybridization, a stringent condition or a high stringent condition is generally used. Stringent conditions and high stringent conditions are well known in the field of molecular biology. For example, a stringent condition may refer to hybridization in 6×sodium chloride/sodium citrate (SSC), at about 45° C., followed by washing in 0.2×SSC/0.1% SDS, at about 50-65° C. for one or more times. A high stringent condition may refer to hybridization in 6×SSC at about 45° C. followed by washing in 0.1×SSC/0.2% SDS, at about 68° C. for one or more times. With respect to the other stringent conditions or high stringent conditions known by a person skilled in the art, please refer to, example, Ausubel, F. M. et al. (ed.), 1989, Current Protocols in Molecular Biology, Vol. 1, Green Publishing Associates, Inc., and John Wiley & Sons, Inc., New York, pages 6.3.1-6.3.6 and 2.10.3.

As used herein, the term "linker" refers to a short peptide for linking two molecules (e.g., proteins). Such linkers are well known by a person skilled in the art, including, but not limited to a flexible linker, such as $(Gly)_4$, $(Gly)_4$-Ser, and $((Gly)_4$-Ser$)_3$.

In the invention, the terms "polypeptide" and "protein" have the same meanings, which can be used interchangeably. Moreover, in the invention, amino acids are generally expressed as one-letter codes and three-letter codes. For example, alanine may be expressed as A or Ala.

As used herein, the term "restriction enzyme cleavage site" refers to an enzyme cleavage site recognized by a restriction enzyme. Such restriction enzyme cleavage sites are well known by a person skilled in the art, including, but not limited to the enzyme cleavage sites recognized by restriction enzymes such as EcoR I, BamH I, Hind II, Hind III, Hpa I, Hpa II, Mbo I, and Mbo II.

As used herein, the term "antigenic epitope", "antigen epitope" and "epitope" refer to a part on an antigen that is specifically bound by an immunoglobulin or antibody. "Epitope" is also called "antigenic determinant" in the art. An epitope or antigenic determinant generally consists of chemically active surface groups of a molecule, such as amino acids, carbohydrates or saccharide sidechains, and generally has a specific 3D structural characteristic and a specific charge characteristic. For example, an epitope generally comprises at least 3, 4, 5, 6, 7, 8, 9, 10, 11, 12, 13, 14 or 15 contiguous or non-contiguous amino acids in its unique conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are linearly present along the primary amino acid sequence of the protein. In a conformational epitope, the interaction sites are spaced from each other by amino acid residues of the protein.

As used herein, the term "T cell epitope" refers to an epitope that is recognized by a T cell receptor (TCR). Accordingly, a human T cell epitope refers to an epitope that is recognized by a human T cell receptor (TCR). As generally understood by those skilled in the art, a TCR generally does not recognize a conformational epitope, but only recognizes a linear epitope consisting of contiguous amino acid residues (e.g., a small polypeptide of about 10-20 amino acids). Moreover, such an epitope needs to be bound with an MHC molecule so that it can be recognized by a TCR. Thus, depending on the type of the MHC molecule bound, human T cell epitopes can be classified into MHC I and MHC II restricted human T cell epitopes, which bind to MHC class I molecules and MHC class II molecules, respectively. In the present context, an exemplary MHC I restricted human T cell epitope is set forth in SEQ ID NO: 87 (See Zhang H P, Yan H P, Zhang Y H, et al. Detection of antigen-epitope-specific cytotoxic T lymphocytes in patients with hepatitis B virus infection by enzyme linked immunospot assay[J]. Zhonghua yu fang yi xue za zhi [Chinese journal of preventive medicine], 2009, 43(8): 690-694); an exemplary MHC II restricted human T cell epitope is set forth in SEQ ID NOs: 88-89 (See J Immunol. 2000 Feb. 1; 164(3):1625-33 and Proc. Nati. Acad. Sci. USA Vol. 85, pp. 1610-1614, March 1988). However, it will be readily understood that as a linear epitope is irrelevant to the spatial structure, configuration and conformation, one skilled in the art can also choose other human T cell epitopes to conduct the present invention. The invention is not limited by a specific human T cell epitope.

As used herein, the term "HBsAg epitope" refers to a part on HBsAg that can be specifically bound by an immunoglobulin or antibody. The structure and function of HBsAg of human HBV have been well studied. Moreover, many papers have reported the epitopes on HBsAg of human HBV. See, for example, WO 97/39029 A2; WO 85/04103 A1; Xiaoxing Qiu et al., The Journal of Immunology, 1996, Vol. 156, pages 3350-3356; WO 2013/185558 A1, etc.

As used herein, the term "epitope peptide" refers to a peptide fragment on an antigen that can form an epitope or act as an epitope. Under some conditions, an epitope peptide alone can be specifically recognized/bound by an antibody against the epitope. Under some other conditions, an epitope peptide has to be fused to a polypeptide carrier to facilitate the epitope peptide to be specifically recognized by an antibody. The epitope comprised in an epitope peptide may be a linear epitope, or a conformational epitope. When an epitope peptide comprises a linear epitope, it may comprise or is a contiguous amino acid segment (i.e., a peptide fragment) forming the epitope in an antigen. When an epitope peptide comprises a conformational epitope, it may comprise or is a contiguous amino acid segment (i.e., a peptide fragment) covering all the amino acid residues involved in the conformational epitope. In some embodiments of the invention, an epitope peptide preferably has a length of no more than 500 amino acid residues, for example, a length of no more than 400 amino acid residues, a length of no more than 300 amino acid residues, a length of no more than 200 amino acid residues, a length of no more than 100 amino acid residues, a length of no more than 90 amino acid residues, a length of no more than 80 amino acid residues, a length of no more than 70 amino acid residues, a length of no more than 60 amino acid residues, a length of no more than 50 amino acid residues, a length of no more than 40 amino acid residues, a length of no more than 30 amino acid residues, or a length of no more than 25 amino acid residues.

As used herein, the term "polypeptide carrier" refers to such a carrier protein that may act as a carrier of an epitope peptide, i.e., may have the epitope peptide inserted at a specific position (for example, within the protein, or at N-terminus or C-terminus of the protein) therein, so that the epitope peptide can be presented and thus can be recognized by an antibody or immune system. Such carrier proteins have been reported in the previous papers, including, for example, HPV L1 protein (into which the epitope peptide may be inserted between the amino acids from positions 130 to 131 or between the amino acids from positions 426 to 427 of the protein; see Slupetzky, K. et al., Chimeric papillomavirus-like particles expressing a foreign epitope on capsid surface loops[J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16[J]. J Virol, 2003, 77: 8386-8393), CRM197 protein (the epitope peptide may be linked to the N-terminus or C-terminus of the protein or a fragment thereof), and so on. As discussed above, the invention provides a new class of polypeptide carriers for presenting target polypeptides, which are particularly suitable for presenting an epitope peptide comprising an antigenic epitope from human hepatitis B virus (e.g., an epitope of HBsAg from human HBV). In an embodiment of the invention, a linker (e.g., a flexible or rigid linker) may be used between an epitope peptide and a polypeptide carrier, to promote their folding, respectively.

As used herein, the term "recombinant protein" only means that the protein described is not a naturally occurring protein, and is not intended to restrict the means of producing or obtaining the protein. The recombinant protein of the invention may be produced by any known methods, including, but not limited to, genetic engineering methods and artificial synthesis methods.

As used herein, the term "virus-like particle" refers to a hollow particle formed by one or more structural proteins of a certain virus, which does not comprise viral nucleic acid, cannot be self-replicated, but is the same as or similar to a true virion in terms of morphology and structure.

As used herein, the term "a pharmaceutically acceptable carrier and/or excipient" refers to a carrier and/or excipient that is pharmacologically and/or physiologically compatible to a subject and active ingredients, which is well known in the art (see, e.g., Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, non-ionic surfactants (e.g., Tween-80); and ionic strength enhancers include, but are not limited to, NaCl.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments currently. Aluminum hydroxide adjuvant is used in clinical trials more commonly.

As used herein, the term "E. coli expression system" refers to an expression system consisting of E. coli (strains) and a vector, wherein the E. coli (strains) include, but are not limited to: GI698, ER2566, BL21 (DE3), B834 (DE3), and BLR (DE3), which are available on the market.

As used herein, the term "vector" refers to a nucleic acid vehicle which can have a polynucleotide inserted therein. When the vector allows for the expression of the protein encoded by the polynucleotide inserted therein, the vector is called an expression vector.

The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as a vector, include, but are not limited to, retrovirus (including lentivirus), adenovirus, adeno-associated virus, herpes virus (such as herpes simplex virus), pox virus, baculovirus, papillomavirus, and papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, a prokaryotic cell such as E. coli or Bacillus subtilis, a fungal cell such as yeast cell or Aspergillus, an insect cell such as S2 Drosophila cell or Sf9, and an animal cell such as fibroblast, CHO cell, COS cell, NSO cell, HeLa cell, BHK cell, HEK 293 cell or human cell.

As used herein, the term "subject" refers to a mammal, for example, a primate mammal, such as human.

As used herein, the term "an effective amount" refers to an amount that is sufficient to achieve or at least partially achieve a desired effect. For example, an effective amount for preventing a disease (e.g., HBV infection, or a disease associated with HBV infection) refers to an amount that is sufficient to prevent, suppress or delay the development of the disease (e.g., HBV infection, or a disease associated with HBV infection); a therapeutically effective amount refers to an amount that is sufficient to cure or at least partially suppress a disease and its complications in a patient with the disease. Determination of such an effective amount is completely within the ability of a person skilled in the art. For example, an amount effective for a therapeutic use depends on the severity degree of a disease to be treated, general state of the immune system in a patient, general conditions of a patient, such as age, body weight and gender, administration routes of drugs, additional therapies used simultaneously, and the like.

Beneficial Effects of the Invention

The technical solutions of the invention have the following beneficial effects over the prior art:

(1) The invention provides a new polypeptide carrier, which has a broad applicability, can be used to efficiently present various target polypeptides (e.g., antigen epitopes/antigen peptide fragments), and induce generation of a specific immune response to a target polypeptide in a host. Such a target polypeptide (e.g., an antigenic epitope/antigen peptide fragment) includes, but is not limited to, an antigenic epitope/antigen peptide fragment from HIV (e.g., an antigenic epitope/antigen peptide fragment from HIV GP120 protein; for example, a polypeptide comprising the amino acids from positions 361-375 of GP120 protein), an antigenic epitope/antigen peptide fragment from human PD-L1 protein (e.g., a polypeptide comprising amino acids from positions 147-160 of human PD-L1 protein), and an antigenic epitope/antigen peptide fragment from human HBV (e.g., an antigenic epitope/antigen peptide fragment of HBsAg protein from human HBV; e.g., a polypeptide comprising the amino acids from positions 113-135 of HBsAg protein).

(2) The polypeptide carriers of the invention are particularly suitable for presenting antigen epitopes from human hepatitis B virus (e.g., epitopes in HBsAg from human HBV), are able to induce a very strong and specific immune response for cleaning HBsAg in a subject, with an efficacy significantly better than that of the existing hepatitis B vaccines (e.g., vaccines comprising the same epitope and constructed by using HBcAg of human HBV as a polypeptide carrier).

(3) The polypeptide carrier carrying a human T cell epitope according to the present invention is capable of inducing an enhanced immune response in the human body, for example, stimulating secretion of IFNγ by human immune cells, and thus is particularly advantageous.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantageous aspects of the invention are obvious for a person skilled in the art.

DESCRIPTION OF THE DRAWINGS

FIG. 1 shows a scheme of cloning solutions in which recombinant proteins are constructed by inserting a target polypeptide (a target antigen peptide fragment) into RBHBcAg carrier, TBHBcAg carrier and HBHBcAg carrier of the invention.

FIG. 3A: the target polypeptide used was SEQ ID NO: 20, and the titer of anti-GP120 antibodies was determined; FIG. 3B: the target polypeptide used was SEQ ID NO: 21, and the titer of anti-PD-L1 antibodies was determined; FIG. 3C: the target polypeptide used was SEQ ID NO: 22, and the titer of anti-HBsAg antibodies was determined.

FIG. 10 shows a scheme of cloning solutions in which recombinant proteins are constructed by inserting a target polypeptide (a target antigen peptide fragment) into RBHB-cAg-T3 carrier, TBHBcAg-T3 carrier and HBHBcAg-T3 carrier of the invention.

FIG. 11 shows SDS-PAGE results of 2 recombinant proteins (RBHBcAg189-T3-SEQ22 and RBHBcAg149-T3-SEQ22) constructed in the Example 7, and the Transmission Electron Microscope (TEM) results of the virus-like particles formed by said recombinant proteins.

SEQUENCE INFORMATION

Figure 2:
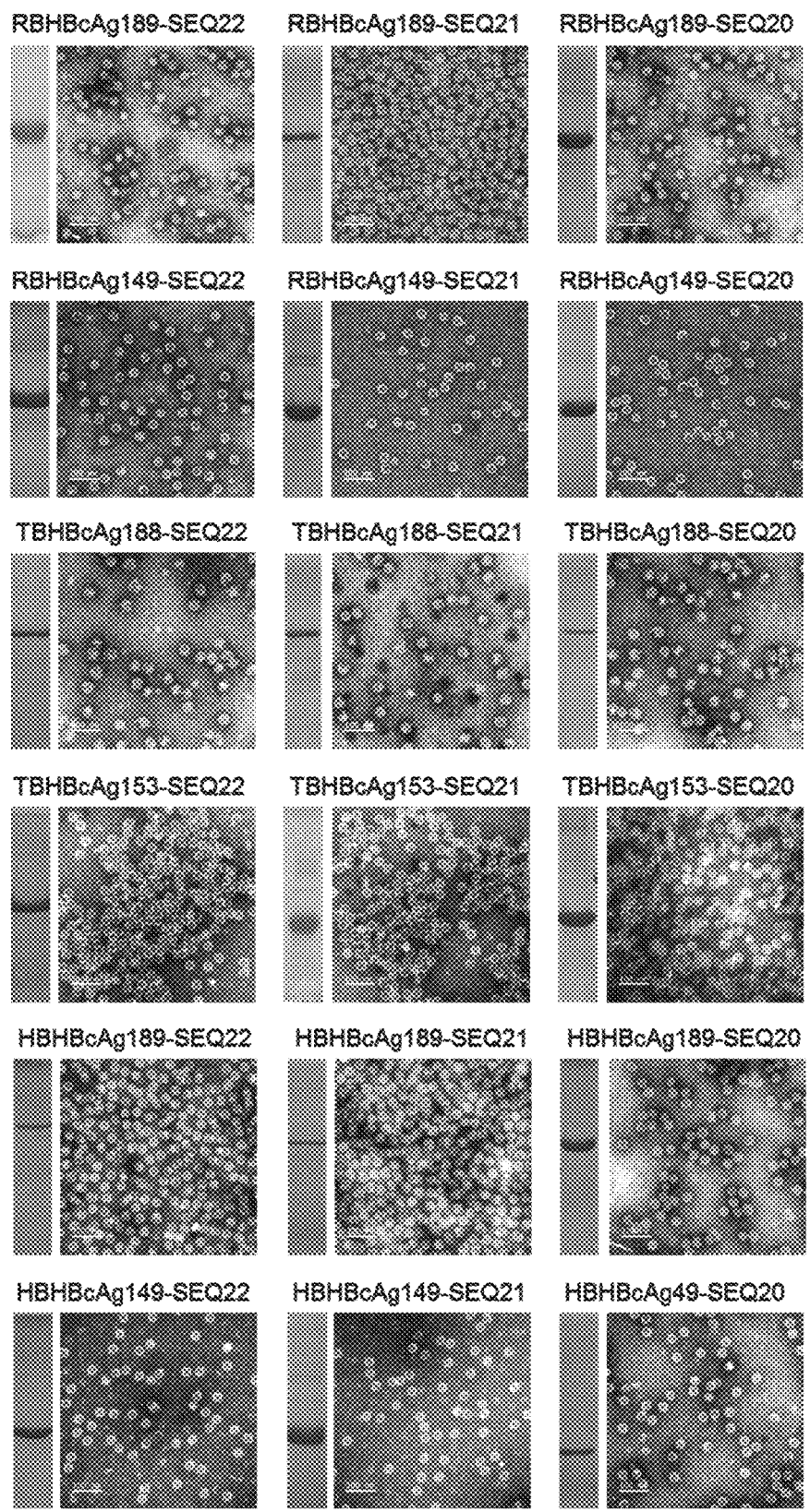
FIG. 2 shows the SDS-PAGE results of 18 recombinant proteins constructed in Example 2, and the Transmission Electron Microscope (TEM) results of the virus-like particles formed by the recombinant proteins.

Information on a part of sequences (SEQ ID NO: 1-44 and 75-96) involved in the invention is provided in the following Table 1.

TABLE 1

| SEQ ID NO | Name | Sequence information |
|---|---|---|
| 1 | RBHBcAg | MDIDPYKEFGASSQLISFLPEDFFPNLAELVETTTALYEEELVGKEHCSPHHTALR SLLNCWGETVRLITWVRNSVEGPLIQDAIVQQVQASVGLRMRQLMWFHLSCLT FGQPTVIEFLVSFGTWIRTPQAYRPPNAPILSTLPEHTIVRRRGGSRATRSPRRRTP SPRRRRSQSPRRRRSQSPASSNC |
| 2 | TBHBcAg | MENLERLDIYKEFGVSDVLVSPLPDDFFPTLQQLLESVNALYEDELTGPNHCSPH HTALRHLIMCGVELRDFIDWMHEQGLSPDADALLAGYLRSKYLKHITKAIWYH LSCLTFGKQTVHEYLVSFGTWIRTPAAYRPVNAPILTTLPETSVIRRRPASRRSTPS PRRRRSQSPRRRRSPSPRPASNC |
| 3 | HBHBcAg | MDIDPYKEFGASSQLVSFLPADFFPALNDLVETTSVALYEEDLVGKEHCSPHHAAL RALLNCWEETVRLITWVRATVEGQPVQDAIIGYVQTTVGLRMRQQIWFHLSCLT FGQQTVIEFLVSFGTWMRTPAAYRPPNAPILSTLPEHTVIRRRGNPRAPRSPRRRT PSPRRRRSQSPRRRRSQSPAPSNC |
| 4 | RBHBcAg189 | MDIDPYKEFGASSQLISFLPEDFFPNLAELVETTTALYEEELVGKEHCSPHHTALR SLLNCWGETVRLITWVRNSVEGGGGGSGGGGTGSEFGGGGSGGGGSQDAIVQQ VQASVGLRMRQLMWFHLSCLTFGQPTVIEFLVSFGTWIRTPQAYRPPNAPILSTL PEHTIVRRRGGSRATRSPRRRTPSPRRRRSQSPRRRRSQSPASSNC |
| 5 | RBHBcAg149 | MDIDPYKEFGASSQLISFLPEDFFPNLAELVETTTALYEEELVGKEHCSPHHTALR SLLNCWGETVRLITWVRNSVEGGGGGSGGGGTGSEFGGGGSGGGGSQDAIVQQ VQASVGLRMRQLMWFHLSCLTFGQPTVIEFLVSFGTWIRTPQAYRPPNAPILSTL PEHTIV |

TABLE 1-continued

Sequence information of SEQ ID NO: 1-44 and 75-96

| SEQ ID NO | Name | Sequence information |
|---|---|---|
| 6 | TBHBcAg188 | MENLERLDIYKEFGVSDVLVSFLPDDFFPTLQQLLESVNALYEDELTGPNHCSPK HTALRHLIMCGVELRDFIDWMHEQGGGGSGGGGTGSEFGGGGSGGGGSDAD ALLAGYLRSKYLKHITKAIWYHLSCLTFGKQTVHEYLVSFGTWIRTPAAYRPVN APILTTLPETSVIRRRPASRRSTPSPRRRRSQSPRRRRSPSPRPASNC |
| 7 | TBHBcAg153 | MENLERLDIYKEFGVSDVLVSFLPDDFFPTLQQLLESVNALYEDELTGPNHCSPH HTALRHLIMCGVELRDFIDWMHEQGGGGSGGGGTGSEFGGGGSGGGGSDAD ALLAGYLRSKYLKHITKAIWYHLSCLTFGKQTVHEYLVSFGTWIRTPAAYRPVN APILTTLPETSVI |
| 8 | HBHBcAg189 | MDIDPYKEFGASSQLVSFLPADFFPALNDLVETSVALYEEDLVGKEHCSPHHAAL RALLNCWEETVRLITWVRATVEGGGGSGGGGTGSEFGGGGSGGGGSQDAIIG YVQTTVGLRMRQQIWFHLSCLTFGQQTVIEFLVSFGTWMRTPAAYRPPNAPILST LPEHTVIRRRGNPRAPRSPRRRTPSPRRRRSQSPRRRRSQSPAPSNC |
| 9 | HBHBcAg149 | MDIDPYKEFGASSQLVSFLPADFFPALNDLVETSVALYEEDLVGKEHCSPHHAAL RALLNCWEETVRLITWVRATVEGGGGSGGGGTGSEFGGGGSGGGGSQDAIIG YVQTTVGLRMRQQIWFHLSCLTFGQQTVIEFLVSFGTWMRTPAAYRPPNAPILST |
| 10 | HBcAg183 | MDIDPYKEFGASVELLSFLPSDFFPSIRDLLDTASALYREALESPEHCSPHHTALR QAILCWGELMNLATWVGSNLEDGGGGSGGGGTGSEFGGGGSGGGGSRELVVS YVNVNMGLKIRQLLWFHISCLTFGRETVLEYLVSFGVWIRTPPAYRPQNAPILSTL PETTVVRRRGRSPRRRTPSPRRRRSQSPRRRRSQSRESQC |
| 11 | HBcAg149 | MDIDPYKEFGASVELLSFLPSDFFPSIRDLLDTASALYREALESPEHCSPHHTALR QAILCWGELMNLATWVGSNLEDGGGGSGGGGTGSEFGGGGSGGGGSRELVVS YVNVNMGLKIRQLLWFHISCLTFGRETVLEYLVSFGVWIRTPPAYRPQNAPILSTL PETTVV |
| 12 | RBHBcAg189 | ATGGACATTGATCCTTATAAAGAATTTGGAGCTTCATCTCAACTGATCTCTTTC TTGCCTGAGGACTTTTTCCCAAACCTTGCAGAATTGGTCGAGACCACCACAG CXCTCTATGAAGAAGAATTAGTAGGTAAGGAGCATTGCTCCCCTCACCATACT GCTTTACGATCCTTGCTAAATTGCTGGGGAGAGACTGTTAGATTAATAACTTG GGTCAGGAACTCTGTGGAGGGAGGTGGAGGTGGTTCTGGAGGTGGTGGTAC TGGATCCGAATTCGGTGGTGGAGGTTCAGGAGGAGGTGGTTCCAAGATGCC ATTGTCCAGCAAGTTCAGGCCTCGGTGGGCCTGCGCATGAGACAGTTAATGT GGTTCCATCTCTCATGCCTAACATTTGGACAGCCCACTGTCATAGAATTTCTGG TCTCTTTTGGAACATGGATCAGAACCCCGCAAGCTTACAGACCCCCTAATGCA CCCATTCTCTCGACTGTTCCGGAGCATAGAATCGTTAGGAGAAGAGGAGGTTC ACGCGCTACTAGGTCCCCCCGAAGGCGCACTCCCTCTCCTCGCCGACGCAGA TCTCAATCGCCGCGTCGCCGCAGATCTCAGTCTCCAGCTTCCTCCAACTGCTA A |
| 13 | RBHBcAg149 | ATGGACATTGATCCTTATAAAGAATTTGGAGCTTCATCTCAACTGATCTCTTTC TTGCCTGAGGACTTTTTCCCAAACCTTGCAGAATTGGTCGAGACCACCACAG CTCTCTATGAAGAAGAATTAGTAGGTAAGGAGCATTGCTCCCCTCACCATACT GCTTTACGATCCTTGCTAAATTGCTGGGGAGAGACTGTTAGATTAATAACTTG GGTCAGGAACTCTGTGGAGGGAGGTGGAGGTGGTTCTGGAGGTGGTGGTAC TGGATCCGAATTCGGTGGTGGAGGTTCAGGAGGAGGTGGTTCCAAGATGCC ATTGTCCAGCAAGTTCAGGCCTCGGTGGGCCTGCGCATGAGACAGTTAATGT GGTTCCATCTCTCATGCCTAACATTTGGACAGCCCACTGTCATAGAATTTCTGG TCTCTTTTGGAACATGGATCAGAACCCCGCAAGCTTACAGACCCCCTAATGCA CCCATTCTCTCGACTCTTCCGGAGCATACAATCGTT |
| 14 | TBHBcAg188 | ATGAAAAACCTTGAAAGACTGACATCTATAAAGAATTTGGAGTCTCTGATGT CTTGGTGTCTTTCTTACCTGATGATTTCTTTCCAACTTTACAGCAACTTTTGGA ATCAGTGAATGCCCTATATQAGGATGAACTCACTGGGCCTAATCACTGTTCTC CCCATCATACTGCCTTAAGGCACTTGATTATGTGTGGGGTAGAATTAAGAGATT TTATTGATTGGATGCATGAACAGGGGGGTGGAGGTGGTTCTGGAGGTGGTGG TACTGGATCCGAATTCGGTGGTGGAGGTTCAGGAGGAGGTGGTTCCGATGCA GACGCTCTTTTGGCTGGTTACCTTCGATCCAAATATCTTAAACATATTACCAAG GGTATTTGGTATCATTTAAGGTGTTTGAGCTTTGGTAAGGAAAGAGTGCATGAA TACCTGGTATCCTTTGGCACCTGGATCAGAACCCCAGCTGCATATAGACCAGT GAATGCACCCATTCTCACCACTCTTCCGGAAACTTCAGTTATCAGAAGAAGG CCTGCCTCCAGAAGATCTACTCCCTCTCCTCGCAGACGCCGATCTCAATCACC GCGCCGCCGCCGCTCTCCATCTCCAAGACCAGCAAGCAATTGCTGA |
| 15 | TBHBcAg153 | ATGAAAAACCTTGAAAGACTTGACATCTATAAAGAATTTGGAGTCTCTGATGT CTTGGTGTCTTTCTTACCTGATGATTTCTTTCCAACTTTACAGCAACTTTTGGA ATCAGTGAATGCGCTATATGAGGATGAAGTCACTGGGCCTAATGAGTGTTGTC CCCATCATACTGCCTTAAGGCACTTGATTATGTGTGGGGTAGAATTAAGAGATT TTATTGATTGGATGCATGAACAGGGGGGTGGAGGTGGTTCTGGAGGTGGTGG TACTGGATCCGAATTCGGTGGTGGAGGTTCAGGAGGAGGTGGTTCCGATGCA GACGCTCTTTTGGCTGGTTACCTTCGATCCAAATATCTTAAACATATTACCAAG GCTATTTGGTATCATTTAAGCTGTTTGACCTTTGGTAAGCAAACAGTGCATGAA |

TABLE 1-continued

Sequence information of SEQ ID NO: 1-44 and 75-96

| SEQ ID NO | Name | Sequence information |
|---|---|---|
|  |  | TACCTGGTATCCTTTGGCAGCTGGATCAGAACCGCAGCTGCATATAGACCAGT<br>GAATGCACCCATTCTCACCACTCTTCCGGAAACTTCAGTTATC |
| 16 | HBHBcAg189 | ATGGACATTGATCCTTATAAAGAGTTCGGTGCTTCATCTCAACTTGTCTCCTTT<br>TTGCCTGCTGACTTCTTTCCCGCCTTGAACGACCTGGTGGAAACTTCGGTGGC<br>CTTATATGAGGAAGACCTTGTAGGTAAGGAGCATTGCTCCCCTCATCATGCAG<br>CCTTAAGGGCCCTACTTAATTGCTGGGAGGAAACAGTCAGACTGATTACCTG<br>GGTCCGTGCGACAGTAGAGGGAGGTGGAGGTGGTTCTGGAGGTGGTGGTAC<br>TGGATCCGAATTCGGTGGTGGAGGTTCAGGAGGAGGTGGTTCCCAGGATGCC<br>ATCATCGGTTATGTCCAGACTACGGTGGGCCTACGCATGAGACAACAGATCTG<br>GTTCCATCTCTCATGCCTTACTTTTGGGCAGCAGACTGTGATAGAGTTCCTGG<br>TCTCATTTGGGACATGGATGAGAACTCCAGCCGCCTATAGACCCCGCAATGCA<br>CCCATTTTATCAACTCTTCCAGAGCACACAGTCATTAGGAGAAGAGGAAATGC<br>GCGTGCTCCTAGGTCCCCCAGAAGGCGCACTCCCTCTCCTCGCCGACGCAGA<br>TCTCAATCTCCGCGTCGCCGGAGATCTCAATCTCCAGCTCCCTCCAACTGCTA<br>A |
| 17 | HBHBcAg149 | ATGGACATTGATCCTTATAAAGAGTTCGGTGCTTCATCTCAACTTGTCTCCTTT<br>TTGCCTGCTGACTTCTTTCCCGCCTTGAACGACCTGGTGGAAACTTCGGTGGC<br>CTTATATGAGGAAGACCTTGTAGGTAAGGAGCATTGCTCCCCTCATCATGCAG<br>CCTTAAGGGCCCTACTTAATTGCTGGGAGGAAACAGTCAGACTGATTACCTG<br>GGTCCGTGCCACAGTAGAGGGAGGTGGAGGTGGTTCTGGAGGTGGTGGTAC<br>TGGATCCGAATTCGGTGGTGGAGGTTCAGGAGGAGGTGGTTCCCAGGATGCC<br>ATCATCGGTTATGTCCAGACTACGGTGGGCCTACGCATGAGACAACAGATCTG<br>GTTCCATCTCTCATGCCTTACTTTTGGGCAGCAGACTGTGATAGAGTTCCTGG<br>TCTCATTTGGGACATGGATGAGAACTCCAGCCGCCTATAGACCCCCAATGCA<br>CCCATTTTATCAACTCTTCCAGAGCACACAGTCATT |
| 18 | HBcAg183 | ATGGACATTGATCCATATAAAGAATTTGGAGCTTCTGTGGAGTTACTCTCTTTT<br>TTGCCTTCCGACTTCTTTCCTTCTATCCGAGATCTCCTCGACACCGCCTCTGGT<br>CTGTATGGGGAGGCCTTAGAGTCTCCGGAACATTGTTCACCTCACCATACGGC<br>ACTCAGGCAAGCTATTCTGTGTTGGGGTGAGTTGATGAATCTAGCCACCTGGG<br>TGGGAAGTAATTTGGAAGATGGTGGAGGTGGTTCTGGAGGTGGTGGTACTGG<br>ATCCGAATTCGGTGGTGGAGGTTCAGGAGGAGGTGGTTCCAGGGAACTAGTA<br>GTCAGCTATGTCAACGTTAATATGGGCCTAAAAATCAGACAACTATTGTGGTT<br>TCACATTTCCTGTCTTACTTTTGGGAGAGAAAGTGTTGTTGAATATTTGGTGTG<br>TTTTGGAGTGTGGATTCGCACTCCTCCTGCATATAGACCACAAAATGCCCCCTA<br>TCTTATCAACACTTCCGGAAACTACTGTTGTTCGTCGCGAGGCCGTAGCCCG<br>CGACGACGTACCCCGAGCCCGCGTCGACGTCGCAGCCAGAGCCCGCGCCGT<br>CGTCGCAGCCAGAGCCGTGAAAGCCAGTGCTAA |
| 19 | HBcAg149 | ATGGACATTGATCCATATAAAGAATTTGGAGCTTCTGTGGAGTTACTCTCTTTT<br>TTGCCTTCCGACTTCTTTCCTTCTATCCGAGATCTCCTCGACACCGCCTCTGCT<br>CTGTATCGGGAGGGCTTAGAGTCTCCGGAACATTGTTCAGGTCAGCATACGGC<br>ACTCAGGCAAGCTATTCTGTGTTGGGGTGAGTTGATGAATCTAGCCACCTGGG<br>TGGGAAGTAATTTGGAAGATGGTGGAGGTGGTTCTGGAGGTGGTGGTACTGG<br>ATCCGAATTCGGTGGTGGAGGTTCAGGAGGAGGTGGTTCCAGGGAACTAGTA<br>GTCAGCTATGTCAACGTTAATATGGGCCTAAAAATCAGACAACTATTGTGGTT<br>TCACATTTGCTGTCTTACTTTTGGGAGAGAAAGTGTTCTTGAATATTTGGTGTC<br>TTTTGGAGTGTGGATTCGCACTCCTCCTGCATATAGACCACAAAATGCCCCTA<br>TCTTATCAACACTTCCGGAAACTACTGTTGTT |
| 20 | HIV-GP120-<br>aa 361-375 | FKQSSGGDPEIVTHS |
| 21 | hPDL1-<br>aa147-160 | TSEHELTCQAEGYP |
| 22 | HBsAg-<br>aa113-135 | SSTTSTGPCKTCTTPAQGTSMFP |
| 23 | RBHBcAg189-<br>SEQ 20 | MDIDPYKEFGASSQLISFLPEDFFPNLAELVETTTALYEEELVGKEHCSPHHTALR<br>SLLNCWGETVRLITWVRNSVEGGGGSGGGGTGSFKQSSGGDPEIVTHSEFGG<br>GGSGGGGSQDAIVQQVQASVGLRMRQLMWFHLSCLTFGQPTVIEFLVSFGTWIR<br>TPQAYRPPNAPTLSTLPEHTTVRRRGGSRATRSPRRRTPSPRRRRSQSPRRRRSQSP<br>ASSNC |
| 24 | RBHBcAg149-<br>SEQ 20 | MDIDPYKEFGASSQLLSFLPEDFFPNLAELVETTTALYEEELVGKEHCSPHHTALR<br>SLLNCWGETVRLITWVRNSVEGGGGSGGGGTGSFKQSSGGDPEIVTHSEFGG<br>GGSGGGGSQDAIVQQVQASVGLRMRQLMWFHLSCLTFGQPTVIEFLVSFGTWIR<br>TPQAYRPPNAPILSTLPEHTIV |
| 25 | TBHBcAg188-<br>SEQ 20 | MENLERLDIYKEFGVSDVLVSFLPDDFFPTLQQLLESVNALYEDELTGPNHCSPH<br>HTALRHLIMCGVELRDFIDWMHEQGGGGSGGGGTGSFKQSSGGDPEIVTHSEF |

TABLE 1-continued

Sequence information of SEQ ID NO: 1-44 and 75-96

| SEQ ID NO | Name | Sequence information |
|---|---|---|
|  |  | GGGGSGGGGSDADALLAGYLRSKYLKHITKAIWYHLSCLTFGKQTVHEYLVSF GTWIRTPAAYRPVNAPILTTLPETSVIRRRPASRRSTPSPRRRRSQSPRRRRSPSPRP ASNC |
| 26 | TBHBcAg153-SEQ 20 | MENLERLDIYKEFGVSDVLVSFLPDDFFPTLQQLLESVNALYEDELTGPNHCSPH HTALRHLIMCGVELRDFIDWMHEQGGGGGSGGGGTGSFKQSSGGDPEIVTHSEF GGGGSGGGGSDADALLAGYLRSKYLKHITKAIWYHLSCLTFGKQTVHEYLVSF GTWIRTPAAYRPVNAPILTTLPETSVI |
| 27 | HBHBcAg189-SEQ 20 | MDIDPYKEFGASSQLVSFLPADFFPALNDLVETSVALYEEDLVGKEHCSPHHAAL RALLNCWEETVRLITWVRATVEGGGGGSGGGGTGSFKQSSGGDPEIVTHSEFGG GGSGGGGSQDAIIGYVQTTVGLRMRQQIWFHLSCLTFGQQTVIEFLVSFGTWMR TPAAYRPPNAPILSTLPEHTV1RRRGNPRAPRSPRRRTPSPRRRRSQSPRRRRSQSP APSNC |
| 28 | HBHBcAg149-SEQ 20 | MDIDPYKEFGASSQLVSFLPADFFPALNDLVETSVALYEEDLVGKEHCSPHHAAL RALLNCVVEETVRLITWVRATVEGGGGGSGGGGTGSFKQSSGGDPEIVTHSEFGG GGSGGGGSQDAIIGYVQTTVGLRMRQQIWFHLSCLTFGQQTVIEFLVSFGTWMR TPAAYRPPNAPILSTLPEHTVI |
| 29 | RBHBcAg189-SEQ 21 | MDIDPYKEFGASSQLISFLPEDFFPNLAELVETTTALYEEELVGKEHCSPHHTALR SLLNCWGETVRLJTWVRNSVEGGGGGSGGGGTGSTSEHELTCQAEGYPEFGGG GSGGGGSQDAIVQQVQASVGLRMRQLMWFHLSCLTFGQPTVIEFLVSFGTWIRT PQAYRPPNAPELSTLPEHTIVRRRGGSRATRSPRRRTPSPRRRRSQSPRRRRSQSPA SSNC |
| 30 | RBHBcAg149-SEQ 21 | MDIDPYKEFGASSQLISFLPEDFFPNLAELVETTTALYEEELVGKEHCSPHHTALR SLLNCWGETVRLITWVRNSVEGGGGGSGGGGTGSTSEHELTCQAEGYPEFGGG GSGGGGSQDAIVQQVQASVGLRMRQLMWFHLSCLTFGQPTVIEFLVSFGTWIRT PQAYRPPNAPJLSTLPEHTIV |
| 31 | TBHBcAg188-SEQ 21 | MENLERLDIYKEFGVSDVLVSFLPDDFFPTLQQLLESVNALYEDELTGPNHCSPH HTALRHLIMCGVELRDFIDWMHEQGGGGGSGGGGTGSTSEHELTCQAEGYPEF GGGGSGGGGSDADALLAGYLRSKYLKHITKAIWYHLSCLTFGKQTVHEYLVSF GTWIRTPAAYRPVNAPILTTLPETSVIRRRPASRRSTPSPRRRRSQSPRRRRSPSPRP ASNC |
| 32 | TBHBcAg153-SEQ 21 | MENLERLDIYKEFGVSDVXVSFLPDDFFPTLQQLLESVNALYEDELTGPNHCSPH HTALRHLIMCGVELRDFIDWMHEQGGGGGSGGGGTGSTSEHELTCQAEGYPEF GGGGSGGGGSDADALLAGYLRSKYLKHITKArWYHLSCLTFGKQTVHEYLVSF GTWIRTPAAYRPVNAPILTTLPETSVI |
| 33 | HBHBcAg189-SEQ 21 | MDIDPYKEFGASSQLVSFLPADFFPALNDLVETSVALYEEDLVGKEHCSPHHAAL RALLNCWEETVRLITWVRATVEGGGGGSGGGGTGSTSEHELTCQAEGYPEFGG GGSGGGGSQDAIIGYVQTTVGLRMRQQIWFHLSCLTFGQQTVIEFLVSFGTWMR TPAAYRPPNAPfLSTLPEHTVIRRRGNPRAPRSPRRRTPSPRRRRSQSPRRRRSQSP APSNC |
| 34 | HBHBcAg149-SEQ 21 | MDIDPYKEFGASSQLVSFLPADFFPALNDLVETSVALYEEDLVGKEHCSPHHAAL RALLNCWEETVRUTWVRATVEGGGGGSGGGGTGSTSEHELTCQAEGYPEFGG GGSGGGGSQDAIIGYVQTTVGLRMRQQIWFHLSCLTFGQQTVIEFLVSFGTWMR TPAAYRPPNAPILSTLPEHTVI |
| 35 | HBHBcAg189-SEQ 22 | MDIDPYKEFGASSQLISFLPEDFFPNLAELVETTTALYEEELVGKEHCSPHHTALR SLLNCWGETVRLITWVRNSVEGGGGGSGGGGTGSSSTTSTGPCKTCTTPAQGTS MFPEFGGGGSGGGGSQDAIVQQVQASVGLRMRQLMWFHLSCLTFGQPTVIEFL VSFGTWIRTPQAYRPPNAPILSTLPEHTIVRRRGGSRAIRSPRRRTPSPRRRRSQSP RRRRSQSPASSNC |
| 36 | RBHBcAg149-SEQ 22 | MDIDPYKEFGASSQLISFLPEDFFPNLAELVETTTALYEEELVGKEHCSPHHTALR SLLNCVVGETVRLITWVRNSVEGGGGGSGGGGTGSSSTTSTGPCKTCTTPAQGTS MFPEFGGGGSGGGGSQDAIVQQVQASVGLRMRQLMWFHLSCLTFGQPTVIEFL VSFGTWIRTPQAYRPPNAPILSTLPEHTIV |
| 37 | TBHBcAg188-SEQ 22 | MENLERLDIYKEFGVSDVLVSFLPDDFFPTLQQLLESVNALYEDELTGPNHCSPH HTALRHLIMCGVELRDFIDWMHEQGGGGGSGGGGTGSSSTTSTGPCKTCTTPAQ GTSMFPEFGGGGSGGGGSDADALLAGYLRSKYLKHITKAIWYHLSCLTFGKQT VHEYLVSFGTWIRTPAAYRPVNAPILTTLPETSVIRRRPASRRSTPSPRRRRSQSPR RRRSPSPRPASNC |
| 38 | TBHBcAg153-SEQ 22 | MENLERLDIYKEFGVSDVLVSFLPDDFFPTLQQLLESVNALYEDELTGPNHCSPH HTALRHLIMCGVELRDFIDWMHEQGGGGGSGGGGTGSSSTTSTGPCKTCTTPAQ GTSMFPEFGGGGSGGGGSDADALLAGYLRSKYLKHITKAIWYHLSCLTFGKQT VHEYLVSFGTWIRTPAAYRPVNAPILTTLPETSVI |

TABLE 1-continued

Sequence information of SEQ ID NO: 1-44 and 75-96

| SEQ ID NO | Name | Sequence information |
|---|---|---|
| 39 | HBHBcAg189-SEQ 22 | MDIDPYKEFGASSQLVSFLPADFFPALNDLVETSVALYEEDLVGKEHCSPHHAAL RALLNCWEETVRLITWVRATVEGGGGSGGGGTGSSSTTSTGPCKTCTTPAQGT SMFPEFGGGGSGGGGSQDAIIGYVQTTVGLRMRQQIWFHLSCLTFGQQTVIEFL VSFGTWMRTPAAYRPPNAPILSTLPEHTVIRRRGNPRAPRSPRRRTPSPRRRRSQS PRRRRSQSPAPSNC |
| 40 | HBHBcAg149-SEQ 22 | MDIDPYKEFGASSQLVSFLPADFFPALNDLVETSVALYEEDLVGKEHCSPHHAAL RALLNCWEETVRLITWVRATVEGGGGSGGGGTGSSSTTSTGPCKTCTTPAQGT SMFPEFGGGGSGGGGSQDAJTGYVQTTVGLRMRQQIWFHLSCLTFGQQTVIEFL VSFGTWMRTPAAYRPPNAPILSTLPEHTVI |
| 41 | HBcAg183-SEQ 22 | MDIDPYKEFGASVELLSFLPSDFFPSIRDLLDTASALYREALESPEHCSPHHTALR QAILCWGELMNLATWVGSNLEDGGGGSGGGGTGSSSTTSTGPCKTCTTPAQGT SMFPEFGGGGSGGGGSRELVVSYVNVNMGLKIRQLLWFHISCLTFGRETVLEYL VSFGVWIRTPPAYRPQNAPILSTLPETTVVRRRGRSPRRRTPSPRRRRSQSPRRRR SQSRESQC |
| 42 | HBcAg149-SEQ 22 | MDIDPYKEFGASVELLSFLPSDFFPSIRDLIDTASALYREALESPEHCSPHHTALFI QAILCWGELMNLATWVGSNLEDGGGGSGGGGTGSSSTTSTGPCKTCITPAQGT SMFPEFGGGGSGGGGSRELVVSYVNVNMGLKIRQLLWFHISCLTFGRETVLEYL VSFGVWIRTPPAYRPQNAPILSTLPETTVV |
| 43 | Linker | GGGGGSGGGGTGSEFGGGGSGGGGS |
| 44 | HBsAg | MENIASGLLGPLLVLQAGFFLLTKILTIPQSLDSWWTSLNFLGGTPVCLGQNSQS QISSHSPTCCPPICPGYRWMCLRRFIIFLCILLLCLIFLLVLLDYQGMLPVCPLIPGS STTSTGPCKTCTTPAQGTSMFPSCCCTKPTDGNCTCIPIPSSWAFAKYLWEWASV RFSWLSLLVPFVQWFVGLSPTVWLSVIWMMWFWGPSLYNILSPFMPLLPIFFCL WVYI |
| 75 | RBHBcAg189-T3 | MDJDPYKEFGASSQLISFLPSDFFPSVAELVETTTALYEEELVGKEHCSPHHTALR QAILCWGELMTLATWVRNSVEGGGGCSGGGGTGSEFGGGGSGGCGSQDAIVQ QVQASVGLRMRQLMWFHLSCLTFGQPTVIEFLVSFGVWIRTPPAYRPPNAPILST LPEHTVIRRRGGSRATRSPRRRTPSPRRRRSQSPRRRRSQSPASSNC |
| 76 | TBHBcAg188-T3 | MENLERDIYKEFGVSDFLPSDFFPSVFPTLQQLLESVNALYEDELTGPNHCSPH HTALRQAILCWGELRDFIDWMHEQGGGGGSGGGGTGSEFGGGGSGGGGSDAD ALLAGYLRSKYLKHITKAIVVYHLSCLTFGKQTVHEYLVSFGVWIRTPPAYRPPN APILTTLPETSVIRRRPASRRSTPSPRRRRSQSPRRRRSPSPRPASNC |
| 77 | HBHBcAg189-T3 | MDIDPYKEFGASSQLVSFLPSDFFPSVNDLVETSVALYEEDLVGKEHCSPHHTAL RQAILCWGELMTLATWVRATVEGGGGSGGGGTGSEFGGGGSGGGGSQDAIIG YVQTTVGLRMRQQIWFHLSCLTFGQQTVIEFLVSFGVVYIRTPPAYRPPNAPILST LPEHTVIRRRGNPRAPRSPRRRTPSPRRRRSQSPRRRRSQSPAPSNC |
| 78 | RBHBcAg149-T3 | MDIDPYKEFGASSQLISFLPSDFFPSVAELVETTTALYEEELVGKEHCSPHHTALR QAILCWGELMTLATWVRNSVEGGGGSGGGGTGSEFGGGGSGGGGSQDAIVQ QVQASVGLRMRQLMWFHLSCLTFGQPTVIEFLVSFGVWIRTPPAYRPPNAPILST LPEHTVI |
| 79 | TBHBcAg153-T3 | MENLERLDIYKEFGVSDFLPSDFFPSVFPTLQQLLESVNALYEDELTCPNHCSPH HTALRQAILCWGELRDFIDWMHEQGGGGGSGGGGTGSEFGGGGSGGGGSDAD ALLAGYLRSKYLKHITKAIWYHLSCLTFGKQTVHEYLVSFGVWIRTPPAYRPPN APILTTLPETSVI |
| 80 | HBHBcAg149-T3 | MDIDPYKEFGASSQLVSFLPSDFFPSVNDLVETSVALYEEDLVGKEHCSPHHTAL RQAILCWGELMTLATWVRATVEGGGGSGGGGTGSEFGGGGSGGGGSQDAIIG YVQTTVGLRMRQQIWFHLSCLTFGQQTV1EFLVSFGVWIRTPPAYRPPNAPILST LPEHTVI |
| 81 | RBHBcAg189-T3 | ATGGACATCGACCCGTACAAAGAATTCGGTGCTTCTTCTCAGCTGATCTCTTT CCTGCCGTCTGACTTCTTCCCGTCTGTTGCTGAACTGGTTGAAACCACCACCG CTCTGTACGAAGAAGAACTGGTTGGTAAAGAACACTGCTCTCCGCACCACAC CGCTCTGCGTCAGGCTATCCTGTGCTGGGGTGAACTGATGACCCTGGCTACC TGGGTTCGTAACTCTGTTGAAGGTGGTGGTGGTGGTTCTGGTGGTGGTGGTA CCGGTTCTGAATTCGGTGGTGGTGGTTCTGGTGGTGGTGGTTCTCAGGACGC TATCGTTCAGCAGGTTCAGGCTTCTGTTGGTCTGCGTATGCGTGAGCTGATGT GGTTCCACCTGTCTTGCCTGACCTTCGGTCAGCCGACCGTTATCGAATTCCTG GTTTGTTTCGGTGTTTGGATCCGTAGGCCGCCGGCTTACCGTCCGCCGAAGGC TCCGATCCTGTCTACCCTGCCGGAACACACCGTTATCCGTCGTCGTGGTAAC CGCGTGCTCCGCGTTCTCCGCGTCGTCGTACCCCGTCTCCGCGTCGTCGTCG TTCTCAGTCTCCGCGTCGTCGTCGTTCTCAGTCTCCGGCTCCGTCTAACTGCT AA |

TABLE 1-continued

Sequence information of SEQ ID NO: 1-44 and 75-96

| SEQ ID NO | Name | Sequence information |
|---|---|---|
| 82 | TBHBcAg188-T3 | ATGGAAAACCTGGAACGTCTGGACATCTACAAAGAATTCGGTGTTTCTGACT TCCTGCCGTCTGACTTCTTCCCGTCTGTTTTCCCGACCCTGCAGCAGCTGCTG GAATCTGTTAACGCTCTGTACGAAGACGAACTGACCGGTCCGAACCACTGCT CTCCGCACCACACCGCTCTGCGTCAGGCTATCCTGTGCTGGGGTGAACTGCG TGACTTCATCGACTGGATGCACGAACAGGGTGGTGGTGGTGGTTCTGGTGGT GGTGGTACCGGTTCTGAATTCGGTGGTGGTGGTTCTGGTGGTGGTGGTTCTG ACGCTGACGCTCTGCTGGCTGGTTACCTGCGTTCTAAATACCTGAAACACAT CACCAAAGCTATCTGGTACCACCTGTCTTGCCTGACCTTCGGTAAACAGACC GTTCACGAATACCTGGTTTCTTTCGGTGTTTGGATCCGTACCCCGCCGGCTTA CCGTCCGCCGAACGCTCCGATCCTGACCACCCTGCCGGAAAGCTCTGTTATC CGTCGTCGTCCGGCTTCTCGTCGTTCTACCCCGTCTCCGCGTCGTCGTCGTTC TCAGTCTCCGCGTCGTCGTCGTTCTCCGTCTCCGCGTCCGGCTTCTAACTGC |
| 83 | HBHBcAg189-T3 | ATGGACATCGACCCGTACAAAGAATTCGGTGCTTCTTCTCAGCTGGTTTCTTT CCTGCCGTCTGACTTCTTCCCGTCTGTTAACGACCTGGTTGAAACCTCTGTTG CTCTGTACGAAGAAGACCTGGTTGGTAAAGAACACTGCTCTCCGCACCACAC CGCTCTGCCTCAGGCTATCCTGTGCTGGGGTGAACTGATGACCCTGGCTACC TGGGTTCGTGCTACCGTTGAAGGTGGTGGTGGTGGTTCTGGTGGTGGTGGTA CCGGTTCTGAATTCGGTGGTGGTGGTTCTGGTGGTGGTGGTTCTCAGGACGC TATCATCGGTTACGTTCAGACCACCGTTGGTCTGCGTATGCGTCAGCAGATC TGGTTCCACCTGTCTTGCCTGACCTTCGGTCAGCAGACCGTTATCGAATTCCT GGTTTCritCGGTGTTTGGATCCGTACCCCGCCGGCTTACCGTCCGCCGAACG CTCCGATCCTGTCTACCCTGCCGGAACACACCGTTATCCGTCGTCGTGGTAA CCCGCGTGCTCCGCGTTCTCCGCGTCGTCGTACCCCGTCTCCGCGTCGTCGTC GTTCTCAGTCTCCGCGTCGTCGTCGTTCTCAGTCTCCGGCTCCGTCTAACTGC |
| 84 | RBHBcAg149-T3 | ATGGACATCGACCCGTACAAAGAATTCGGTGCTTCTTCTCAGCTGATCTCTTT CCTGCCGTCTGACTTCTTCCCGTCTGTTGCTGAACTGGTTGAAACCACCACCG CTCTGTACGAAGAAGAACTGGTTGGTAAAGAACACTGCTCTCCGCACCACAC CGCTCTGCGTCAGGCTATCCTGTGCTGGGGTGAACTGATGACCCTGGCTACC TGGGTTCGTAACTCTGTTGAAGGTGGTGGTGGTGGTTCTGGTGGTGGTGGTA CCGGTTCTGAATTCGGTGGTGGTGGTTCTGGTGGTGGTGGTTCTCAGGACGC TATCGTTCAGCAGGTTCAGGCTTCTGTTGGTCTGCGTATGCGTCAGCTGATGT GGTTCCACCTGTCTTGCCTGACCTTCGGTCAGCCGACCGTTATCGAATTCCTG GTTTCTTTCGGTGTTTGGATCCGTACCCCGCCGGCTTACCGTCCGCCGAACGC TCCGATCCTGTCTACCCTGCCGGAACACACCGTTATCTAA |
| 85 | TBHBcAg153-T3 | ATGGAAAACCTGGAACGTCTGGACATCTACAAAGAATTCGGTGTTTCTGACT TCCTGCCGTCTGACTTCTTCCCGTCTGTTTTCCCGACCCTGCAGCAGCTGCTG GAATCTGTTAACGCTCTGTACGAAGACGAACTGACCGGTCCGAACCACTGCT CTCCGCACCACACCGCTCTGCGTCAGGCTATCCTGTGCTGGGGTGAACTGCG TGACTTCATCGACTGGATGCACGAACAGGGTGGTGGTGGTGGTTCTGGTGGT GGTGGTAGCGGTTCTGAATTCGGTGGTGGTGGTTGTGGTGGTGGTGGTTCTG ACGCTGACGCTCTGCTGGCTGGTTACCTGCGTTCTAAATACCTGAAACACAT CACCAAAGCTATCTGGTACCACCTGTCTTGCCTGACCTTCGGTAAACAGACC GTTCACGAATACCTGGTTTCTTTCGGTGTTTGGATCCGTACCCCGCCGGCTTA CCGTCCGCCGAACGCTCCGATCCTGACCACCCTGCCGGAAACCTCTGTTATC |
| 86 | HBHBcAg149-T3 | ATGGACATCGACCCGTACAAAGAATTCGGTGCTTCTTCTCAGCTGGTTTCTTT CCTGCCGTCTGACTTCTTCCCGTCTGTTAACGACCTGGTTGAAACCTCTGTTG CTCTGTACGAAGAAGACCTGGTTGGTAAAGAACACTGCTCTCCGCACCACAC CGCTCTGCGTCAGGCTATCCTGTGCTGGGGTGAACTGATGACCCTGGCTACC TGGGTTCGTGCTACCGTTGAAGGTGGTGGTGGTGGTTCTGGTGGTGGTGGTA CCGGTTCTGAATTCGGTGGTGGTGGTTCTGGTGGTGGTGGTTCTCAGGACGC TATCATCGGTTACGTTCAGACCACCGTTGGTCTGCGTATGCGTCAGCAGATC TGGTTCCACCTGTCTTGCCTGACCTTCGGTCAGCAGACCGTTATCGAATTCCT GGTTTCTTTCGGTGTTTGGATCCGTACCCCGCCGGCTTACCGTCCGCCGAACG CTCCGATCCTGTCTACCCTGCCGGAACACACCGTTATC |
| 87 | T cell epitope | FLPSDFFPSV |
| 88 | T cell epitope | PHHTALRQAILCWGELMTLA |
| 89 | T cell epitope | VSFGVWIRTPPAYRPPNAPIL |
| 90 | RBHBcAg189-T3-SEQ 22 | MDIDPYKEFGASSQLISFLPSDFFPSVAELVETTTALYEEELVGKEHCSPHHTALR QA1LCWGELMTLATWVRNSVEGGGGGSGGGGTGSSSTTSTGPCKTCTTPAQGT SMFPEFGGGGSGGGGSQDAIVQQVQASVGLRMRQLMWFHLSCLTFGQPTVIEF LVSFGVWIRTPPAYRPPNAPILSTLPEHTVIRRRGNPRAPRSPRRRTPSPRRRRSQ SPRRRRSQSPAPSNC |
| 91 | RBHBcAg149-T3-SEQ 22 | MDIDPYKEFGASSQLISFLPSDFFPSVAELVETTTALYEEELVGKEHCSPHHTALR QAILCWGELMTLATWVRNSVEGGGGGSGGGGTGSSSTTSTGPCKTCTTPAQGT |

TABLE 1-continued

Sequence information of SEQ ID NO: 1-44 and 75-96

| SEQ ID NO | Name | Sequence information |
|---|---|---|
| | | SMFPEFGGGGSGGGGSQDAIVQQVQASVGLRMRQLMWFHLSCLTFGQPTVIEF<br>LVSFGVWIRTPPAYRPPNAPILSTLPEHTVI |
| 92 | TBHBcAg188-<br>T3-SEQ 22 | MENLERLDIYKEFGVSDFLPSDFFPSVFPTLQQLLESVNALYEDELTGPNHCSPH<br>HTALRQAILCWGELRDFIDWMHEQGGGGSGGGGTGSSSTTSTGPCKTCTTPA<br>QGTSMFPEFGGGGSGGGGSDADALLAGYLRSKYLKHITKAIWYHLSCLTFGKQ<br>TVHEYLVSFGVWIRTPPAYRPPNAPILTTLPETSVIRRRPASRRSTPSPRRRRSQSP<br>RRRRSPSPRPASNC |
| 93 | TBHBcAg153-<br>T3-SEQ 22 | MENLERLDIYKEFGVSDFLPSDFFPSVFPTLQQLLESVNALYEDELTGPNHCSPH<br>HTALRQAILCWGELRDFIDWMHEQGGGGSGGGGTGSSSTTSTGPCKTCTTPA<br>QGTSMFPEFGGGGSGGGGSDADALLAGYLRSKYLKHITKAIWYHLSCLTFGKQ<br>TVHEYLVSFGVWIRTPPAYRPPNAPILTTLPETSVI |
| 94 | HBHBcAg189-<br>T3-SEQ 22 | MDIDPYKEFGASSQLVSFLPSDFFPSVNDLVETSVALYEEDLVGKEHCSPHHTAL<br>RQAILCWGELMTLATWVRATVEGGGGSGGGGTGSSSTTSTGPCKTCTTPAQG<br>TSMFPEFGGGGSGGGGSQDAIIGYVQTTVGLRMRQQIWFHLSCLTFGQQTVIEF<br>LVSFGVWIRTPPAYRPPNAPILSTLPEHTVIRRRGNPRAPRSPRRRTPSPRRRRSQ<br>SPRRRRSQSPAPSNC |
| 95 | HBHBcAg149-<br>T3-SEQ 22 | MDIDPYKEFGASSQLVSFLPSDFFPSVNDLVETSVALYEEDLVGKEHCSPHHTAL<br>RQAILCWGELMTLATWVRATVEGGGGSGGGGTGSSSTTSTGPCKTCTTPAQG<br>TSMFPEFGGGGSGGGGSQDAIIGYVQTTVGLRMRQQIWFHLSCLTFGQQTVIEF<br>LVSFGVWJRTPPAYRPPNAPILSTLPEHTVI |
| 96 | RBHBcAg149n-<br>T3-SEQ 22 | MDIDPYKEFGASSQLISFLPSDFFPSVAELVETTTALYEEELVGKEHCSPHHTALR<br>QAILCWGELMTLATWVRNSVEGSSTTSTGPCKTCTTPAQGTSMFPQDAIVQQV<br>QASVGLRMRQLMWFHLSCLTFGQPTVIEFLVSFGVWIRTPPAYRPPNAPILSTLP<br>EHTVI |

Specific Modes for Carrying Out the Invention

The invention is illustrated by reference to the following examples (which are intended to describe the invention rather than limiting the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. Those skilled in the art understand that the examples are used for illustrating the present invention, but not intended to limit the protection scope of the present invention.

Example 1. Construction of Plasmids Encoding Polypeptide Carriers

In the Example, plasmids encoding polypeptide carriers were constructed.

1.1 Preparation of Nucleotide Sequences Encoding Polypeptide Carriers

Based on three bat-derived HBV core antigens (i.e., RBHBcAg protein, TBHBcAg protein, and HBHBcAg protein), the following polypeptide carriers were designed:

RBHBcAg189 carrier, which differs from RBHBcAg protein (SEQ ID NO: 1) in that the amino acid residues from positions 78-81 of RBHBcAg protein are substituted with a linker set forth in SEQ ID NO: 43; the amino acid sequence of RBHBcAg189 carrier is set forth in SEQ ID NO: 4, and the nucleotide sequence of RBHBcAg189 carrier is set forth in SEQ ID NO: 12;

TBHBcAg188 carrier, which differs from TBHBcAg protein (SEQ ID NO: 2) in that the amino acid residues from positions 80-83 of TBHBcAg protein are substituted with a linker set forth in SEQ ID NO: 43; the amino acid sequence of TBHBcAg188 carrier is set forth in SEQ ID NO: 6, the nucleotide sequence of TBHBcAg188 carrier is set forth in SEQ ID NO: 14;

HBHBcAg189 carrier, which differs from HBHBcAg protein (SEQ ID NO: 3) in that the amino acid residues from positions 78-81 of HBHBcAg protein are substituted with a linker set forth in SEQ ID NO: 43; the amino acid sequence of HBHBcAg189 carrier is set forth in SEQ ID NO: 8, and the nucleotide sequence of HBHBcAg189 carrier is set forth in SEQ ID NO: 16.

In addition, based on HBcAg protein of human HBV, HBcAg183 carrier was also designed, as a control. HBcAg183 carrier differs from HBcAg protein of human HBV in that the amino acid residues from positions 79-81 of HBcAg protein of human HBV are substituted with a linker set forth in SEQ ID NO: 43; the amino acid sequence of HBcAg183 carrier is set forth in SEQ ID NO: 10, and the nucleotide sequence of HBcAg183 carrier is set forth in SEQ ID NO: 18.

With respect to the nucleotide sequences of said four carriers, their whole gene synthesis was performed by Sangon Biotech (Shanghai) Co., Ltd.

1.2 Preparation of Plasmids Encoding Polypeptide Carriers

By using the synthesized nucleotide sequences as templates, and using the primers in Table 2, the full-length genes and truncates (i.e., gene fragments truncated at C-terminus) of said 4 carriers were amplified by PCR, respectively. 8 PCR products were obtained, i.e., the gene encoding RBHBcAg189 carrier (SEQ ID NO: 12; the amino acid sequence encoded thereby is SEQ ID NO: 4), the gene encoding RBHBcAg149 carrier (SEQ ID NO: 13; the amino acid sequence encoded thereby is SEQ ID NO: 5), the gene encoding TBHBcAg188 carrier (SEQ ID NO: 14; the amino acid sequence encoded thereby is SEQ ID NO: 6), the gene encoding TBHBcAg153 (SEQ ID NO: 15; the amino acid sequence encoded thereby is SEQ ID NO: 7), the gene encoding HBHBcAg189 carrier (SEQ ID NO: 16; the amino acid sequence encoded thereby is SEQ ID NO: 8), the gene encoding HBHBcAg149 carrier (SEQ ID NO: 17; the amino acid sequence encoded thereby is SEQ ID NO: 9), the gene encoding HBcAg183 carrier (SEQ ID NO: 18; the amino acid sequence encoded thereby is SEQ ID NO: 10), and the gene encoding HBcAg149 carrier (SEQ ID NO: 19; the amino acid sequence encoded thereby is SEQ ID NO: 11).

pTO-T7 vector (Luo Wenxin, Zhang Jun, Yang Haijie, et al., Construction and Application of an *Escherichia coli* High Effective Expression Vector with an Enhancer [J], Chinese Journal of Biotechnology, 2000, 16(5): 578-581) was subjected to double enzyme digestion by NdeI and HindIII, to obtain a linear vector. By Gibson assembly cloning method (New England Biolabs (UK) Ltd), 8 PCR products obtained were ligated to the linear vector, and transformed into DH5a competent bacteria. The transformed bacteria were spread on a plate and cultured, monoclonal colonies were then selected, and the plasmids were extracted and sequenced. It was confirmed by sequencing that 8 plasmids comprising the nucleotide sequences encoding the polypeptide carriers were obtained.

The primers involved in the PCR are shown in Table 2.

TABLE 2

Primer sequences

| SEQ ID NO: | Primer name | Sequence |
|---|---|---|
| 45 | RBHBcAg149/189F | ACTTAAGAAGGAGATATACATATGATGGACATTGATCCTTATAAAG |
| 46 | RBHBcAg149R | GTGGTGCTCGAGGCGGCCGCAAGCTTTTAAACGATTGTATGCTCCGGAAGAGTCGA |
| 47 | RBHBcAg189R | GTGGTGCTCGAGGCGGCCGCAAGCTTTTAGCAGTTGGAGGAAGCTGGAGACTGAGATCTGCGGCGAC |
| 48 | TBHBcAg153/188F | ACTTTAAGAAGGAGATATACATATGATGGAAAACCTTGAAAGACTTG |
| 49 | TBHBcAg153R | GTGGTGCTCGAGGCGGCCGCAAGCTTTTAGATAACTGAAGTTTCCGGAAGAGTG |
| 50 | TBHBcAg188R | GTGGTGCTCGAGGCGGCCGCAAGCTTTTAGCAATTGCTTGCTGGTCTTG |
| 51 | HBHBcAg149/189F | ACTTTAAGAAGGAGATATACATATGATGGACATTGATCCTTATAAAG |
| 52 | HBHBcAg149R | GTGGTGCTCGAGGCGGCCGCAAGCTTTTAAATGACTGTGTGCTCTGGAAGAGTTGA |
| 53 | HBHBcAg189R | GTGGTGCTCGAGGCGGCCGCAAGCTTTTAGCAGTTGGAGGGAGCTGGAGATTGAGATCTCCGGCGAC |

Example 2. Preparation of Recombinant Proteins

In the Example, a nucleotide sequence encoding a target polypeptide was inserted into the plasmid constructed in Example 1, and a recombinant protein comprising the target polypeptide and the polypeptide carrier was obtained. The scheme of cloning solutions, in which recombinant proteins are constructed by inserting a target polypeptide (a target antigen peptide fragment) into RBHBcAg carrier, TBHBcAg carrier and HBHBcAg carrier of the invention, is shown in FIG. 1.

2.1 Construction of Expression Plasmids of Recombinant Proteins Comprising a Target Polypeptide and a Polypeptide Carrier In the Example, 3 target polypeptides were used to verify the versatility of the polypeptide carrier of the invention for presenting peptide fragments. Said 3 target polypeptides were: polypeptide HIV-GP120-aa361-375 (i.e., the amino acids from positions 361-375 of HIV GP120 protein, its amino acid sequence is set forth in SEQ ID NO: 20); polypeptide hPDL1-aa147-160 (i.e., the amino acids from positions 147-160 of human PD-L1 protein, its amino acid sequence is set forth in SEQ ID NO: 21); and polypeptide HBsAg-aa113-135 (i.e., the amino acids from positions 113-135 of hepatitis B surface antigen (HBsAg) from human HBV, its amino acid sequence is set forth in SEQ ID NO: 22).

The sense and antisense sequences coding said 3 target polypeptides (as shown in Table 3) were synthesized directly, and annealed, so as to obtain the gene fragments having cohesive end and encoding the target polypeptides.

TABLE 3

Sense and antisense sequences coding 3 target polypeptides

| SEQ ID NO: | Primer name | Sequence |
|---|---|---|
| 54 | hPDL1-aa147-160F | GATCCACCTCTGAACATGAACTGACATGTCAGGCTGAGGGCTACCCCG |
| 55 | hPDL1-aa147-160R | AATTCGGGGTAGCCCTCAGCCTGACATGTCAGTTCATGTTCAGAGGTG |
| 56 | HIV-GP120-aa361-375F | GATCCTTCAAACAGTCTTCTGGTGGTGACCCGGAAATCGTTACCCACTCTG |
| 57 | HIV-GP120-aa361-375R | AATTCAGAGTGGGTAACGATTTCCGGGTCACCACCAGAAGACTGTTTGAAG |
| 58 | HBsAg-aa113-135F | GATCCTCATCAACAACCAGCACCGGACCATGCAAAACCTGCACAACTCCTGCTCAAGGAACCTCTATGTTTCCCG |
| 59 | HBsAg-aa113-135R | AATTCGGGAAACATAGAGGTTCCTTGAGCAGGAGTTGTGCAGGTTTTGCATGGTCCGGTGCTGGTTGTTGATGAG |

The 6 plasmids (RBHBcAg189, RBHBcAg149, TBHBcAg188, TBHBcAg153, HBHBcAg189 and HBHBcAg149) obtained in Example 1 were subjected to double enzyme digestion by BamHI and EcoRI, to obtain 6 linear vectors. Then, the 3 gene fragments having cohesive end and encoding the target polypeptides, as prepared above, were ligated to the linear vectors, to obtain the expression plasmids encoding recombinant proteins (18 in total: RBHBcAg189-SEQ20, RBHBcAg149-SEQ20, TBHBcAg188-SEQ20, TBHBcAg153-SEQ20, HBHBcAg189-SEQ20, HBHBcAg149-SEQ20, RBHBcAg189-SEQ21, RBHBcAg149-SEQ21, TBHBcAg188-SEQ21, TBHBcAg153-SEQ21, HBHBcAg189-SEQ21, HBHBcAg149-SEQ21, RBHBcAg189-SEQ22, RBHBcAg149-SEQ22, TBHBcAg188-SEQ22, TBHBcAg153-SEQ22, HBHBcAg189-SEQ22, and HBHBcAg149-SEQ22).

2.2 Expression, Purification and Assembly of Recombinant Proteins

The 18 expression plasmids constructed in the previous step, were used to express and purify the recombinant proteins encoded by the expression plasmids via the same method. RBHBcAg149-SEQX (SEQX represents SEQ20, SEQ21 or SEQ22) was used as an example to describe the expression and purification of the recombinant proteins.

(2.2.1) Preparation of bacterial strains for expressing recombinant proteins: the expression plasmid RBHB-cAg149-SEQX obtained in 2.1 was transformed into *E. coli* strain ER2566, so as to obtain the expression bacterial strain.

(2.2.2) Expression of the recombinant protein RBHB-cAg149-SEQX: the expression bacterial strain was seeded in a 500 mL triangular flask, and was cultured at 37° C. on a shaking table until OD was about 1.0; later, isopropyl-beta-D-thiogalactoside (IPTG) was added at a final concentration of 0.5 mM, and the expression was further performed at 25° C. for 6 h.

(2.2.3) Purification of the recombinant protein RBHB-cAg149-SEQX:

(2.2.3.1) Ultrasonic disruption of bacteria: the bacteria in 2.2.2 were harvested by centrifugation, and were subjected to ultrasonic disruption. Sonication buffer: 20 mM phosphate buffer (PH6.0)+300 mM NaCl.

(2.2.3.2) Primary purification of the recombinant protein: the mixture obtained after ultrasonic disruption was incubated in a 65° C. water bath for 30 min, and the supernatant was then collected by centrifugation; saturated ammonium sulfate was added to the supernatant at a volume ratio of 1:1, and the precipitate was collected by centrifugation a suitable volume of buffer (20 mM phosphate buffer (pH=7.4)+150 mM NaCl) was added to resuspend the precipitate, so as to obtain the primarily purified recombinant protein RBHB-cAg149-SEQX.

(2.2.3.3) Purification of the recombinant protein by chromatography: in accordance with the instructions of manufacturer, the protein obtained in 2.2.3.2 was further purified by Sepharose 4FF(GE) molecular sieve column chromatography, so as to obtain the purified recombinant protein. The purified target protein was detected by SDS-PAGE, and the VLP formed by the recombinant protein was observed by Transmission Electron Microscope (TEM).

FIG. 2 shows the SDS-PAGE results of the 18 recombinant proteins as constructed, and the TEM results of the virus-like particles formed by the recombinant proteins. The results show that all the 18 recombinant proteins as obtained had a purity of above 85%, and could be assembled into virus-like particles with a diameter of about 30 nm. These results show that the polypeptide carriers constructed in the invention have a broad versatility, can be used to present various target polypeptides, and can form VLPs.

Example 3. Evaluation on Immunogenicity of Virus-Like Particles

In the Example, the inventors verified the immunogenicity of the virus-like particles formed by the recombinant proteins prepared in Example 2. All such virus-like particles can induce generation of antibodies that specifically bind to target antigens in organisms.

3.1 Immunization of Mice

BALB/C mice were immunized with the 18 virus-like particles prepared in Example 2, respectively. The immunization process was as followed: the immunoadjuvant used was aluminum hydroxide adjuvant; the immunizing dose was 3 ug/dose; the immunization was performed by intramuscular injection at lateral thigh of hindlimb; the immune procedure was primary immunization+booster immunization 2 weeks later (i.e. two times in total).

3.2 Detection of Titer of Antibodies that Specifically Bind to Target Antigens in Sera 3.2.1 Preparation of Reaction Plates The antigens for coating reaction plates were the target antigens corresponding to said three target polypeptides, i.e., HIV-1 gp120 protein (purchased from Sino Biological Inc., Catalog No. 11233-V08H), human PD-L1 protein (purchased from Sino Biological Inc.), and human hepatitis B virus surface antigen recombinantly expressed in CHO cells (HBsAg, purchased from Beijing Wantai Biological Pharmacy).

3 recombinant proteins were diluted with pH9.6 50 mM CB buffer ($NaHCO_3/Na_2CO_3$ buffer, at a final concentration of 50 mM, pH=9.6), respectively, at a final concentration of 2 μg/mL, to obtain the coating solutions. To each well of a 96-well ELISA plate, 100 μL coating solution was added, and the wells were coated at 2-8° C. for 16-24 h, and then further coated at 37° C. for 2 h. After that, PBST washing solution (20 mM PB7.4, 150 mM NaCl, 0.1% Tween20) was used to wash wells once; and 200 μL blocking solution (20 mM $Na_2HPO_4/NaH_2PO_4$ buffer solution containing 20% bovine calf serum and 1%/0 casein, pH=7.4) was then added to each well, and the wells were blocked at 37° C. for 2 h. The blocking solution was discarded. After that, the ELISA plate was dried, and packaged into an aluminum foil bag, which was stored at 2-8° C. for further use.

3.2.2 ELISA Detection of Anti-HBsAg Antibody Titer in Serum

Collection of serum samples: blood was collected from the eye orbit of mice at Week 0, 2, and 4, the serum was separated and cryopreserved at −20° C., until detection.

Sample dilution: a mouse serum was diluted with PBS solution containing 20% newborn bovine serum at 7 dilution gradients, i.e. 1:100, 1:500, 1:2500, 1:12500, 1:62500, 1:312500, and 1:1562500.

ELISA detection: to each well of the coated ELISA plate, 100 μL diluted serum sample was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 100 μL GAM-HRP reaction solution was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 50 μL TMB color developing agent (provided by Beijing Wantai Biological Pharmacy) was added, and incubated at 37° C. for 15 min. After the incubation, to each well of the ELISA plate, 50 μL stop solution (provided by Beijing Wantai Biological Pharmacy) was added, and the OD450/630 value for each well was read by an ELISA instrument.

Calculation of antibody titer: samples, the read values of which were within 0.2-2.0, were analyzed; a regression curve was plotted with the dilution fold and the read value, and the dilution fold of the sample, at which the read value was 2-fold of the background value, was calculated; and the dilution fold of the sample was used as the titer of the specific antibody in serum.

Figure 3:
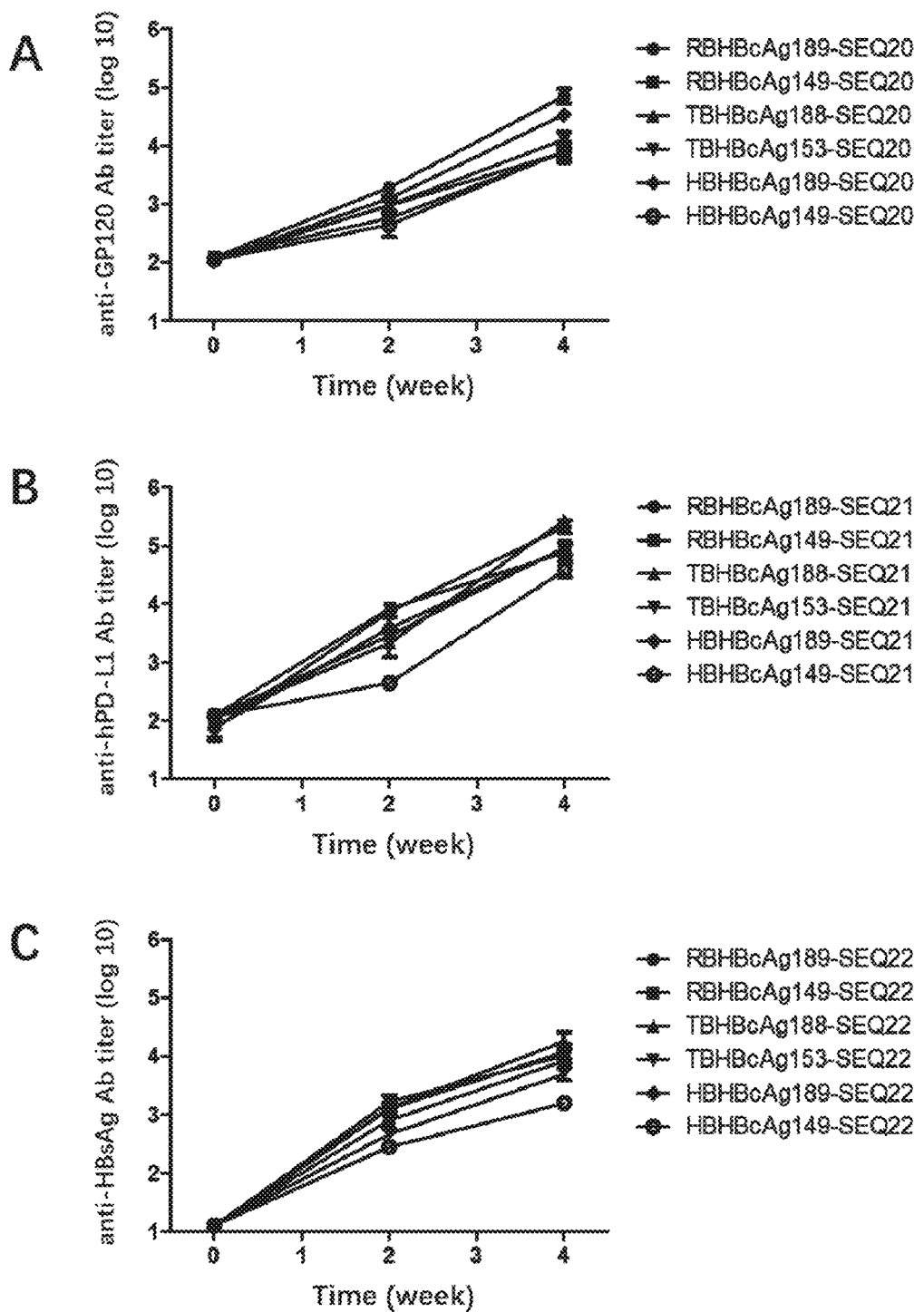
FIG. 3 shows changes in titer of antibodies against the target polypeptides in the recombinant proteins in mouse sera over time, after the immunization of BALB/C mice with the virus-like particles formed by 18 recombinant proteins constructed in Example 2. Longitudinal axis: antibody titer (log 10); horizontal axis: time (week).

FIG. 3 shows changes in titer of antibodies against the target antigen in mouse sera over time, after the immunization of BALB/C mice with the virus-like particles formed by 18 recombinant proteins, respectively. FIG. 3A: the target polypeptide used was SEQ ID NO: 20, and the titer of anti-GP120 antibodies was determined; FIG. 3B: the target polypeptide used was SEQ ID NO: 21, and the titer of anti-PD-L1 antibodies was determined; FIG. 3C: the target polypeptide used was SEQ ID NO: 22, and the titer of anti-HBsAg antibodies was determined. The results show that all the virus-like particles formed by 18 recombinant proteins have good immunogenicity, and can induce the generation of high-titer antibodies that specifically bind to target antigens in mice.

Example 4. Evaluation on Anti-HBV Therapeutic Effects of Virus-Like Particles Presenting HBsAg Epitope (SEQ ID NO: 22)

In the Example, the inventors evaluated the anti-HBV therapeutic effects of the virus-like particles presenting the same epitope peptide (SEQ ID NO: 22), as constructed based on different polypeptide carriers.

4.1 Immunization of Mice

According to the methods described in Example 1-2, 2 recombinant proteins (i.e., HBcAg183-SEQ22, its amino acid sequence is set forth in SEQ ID NO: 41; and HBcAg149-SEQ22, its amino acid sequence is set forth in SEQ ID NO: 42), presenting HBsAg epitope (SEQ ID NO: 22) and constructed based on HBcAg of human HBV, were prepared, and the virus-like particles formed by the 2 recombinant proteins were prepared.

Later, 5 virus-like particles presenting HBsAg epitope (SEQ ID NO: 22) prepared in Example 2, and 2 virus-like particles prepared in the Example were evaluated for the anti-HBV therapeutic effects in a HBV transgenic mouse model.

The immunization method was as followed: the immunoadjuvant used was aluminum hydroxide adjuvant; and the immunizing dose was 12 μg/dose; the immunization was performed by intramuscular injection at lateral thigh of hindlimb: the immune procedure was immunization at Week 0, 2, 3, 4, 5, and 6, (i.e. six times in total).

4.2 Detection of Antibody Titer and Virological Index in Serum

According to the method as described in Example 3.2, the Anti-HBsAg antibody titer in serum was determined, and the virological index (i.e., the level of HBV DNA and HBsAg) in mouse serum was determined.

4.3 Analysis of Therapeutic Effects of Recombinant Proteins

Figure 4:
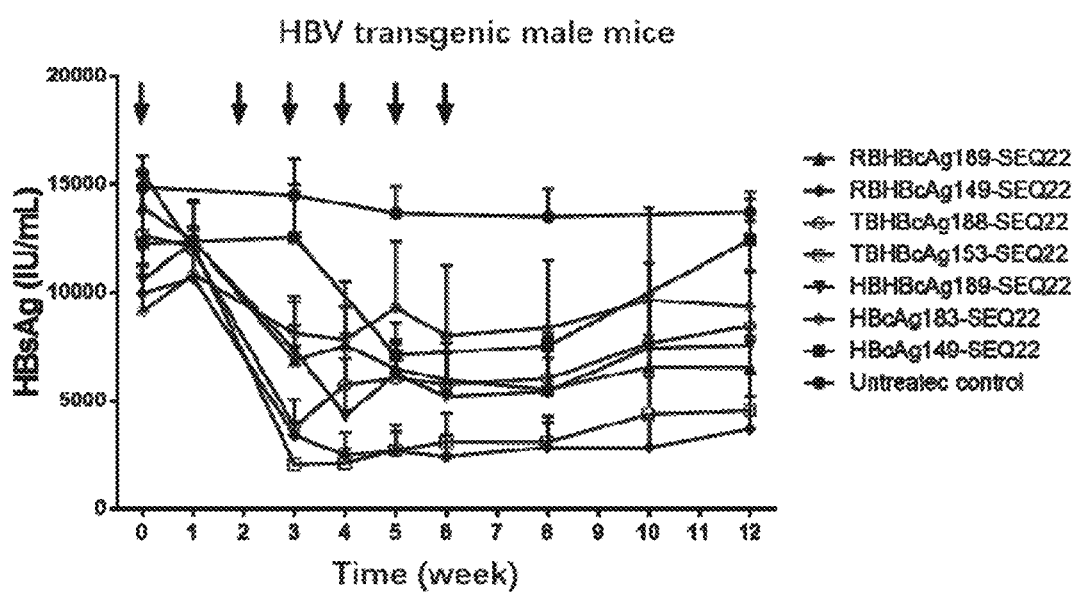
FIG. 4 shows changes in HBsAg level in mouse sera over time, after the treatment of HBV transgenic male (FIG. 4A) and female (FIG. 4B) mice with different virus-like particles presenting the same epitope peptide (SEQ ID NO: 22). Longitudinal axis: HBsAg level (IU/ml); horizontal axis: time (week). The arrows indicate the time points of administering virus-like particles to mice.
Figure 4:
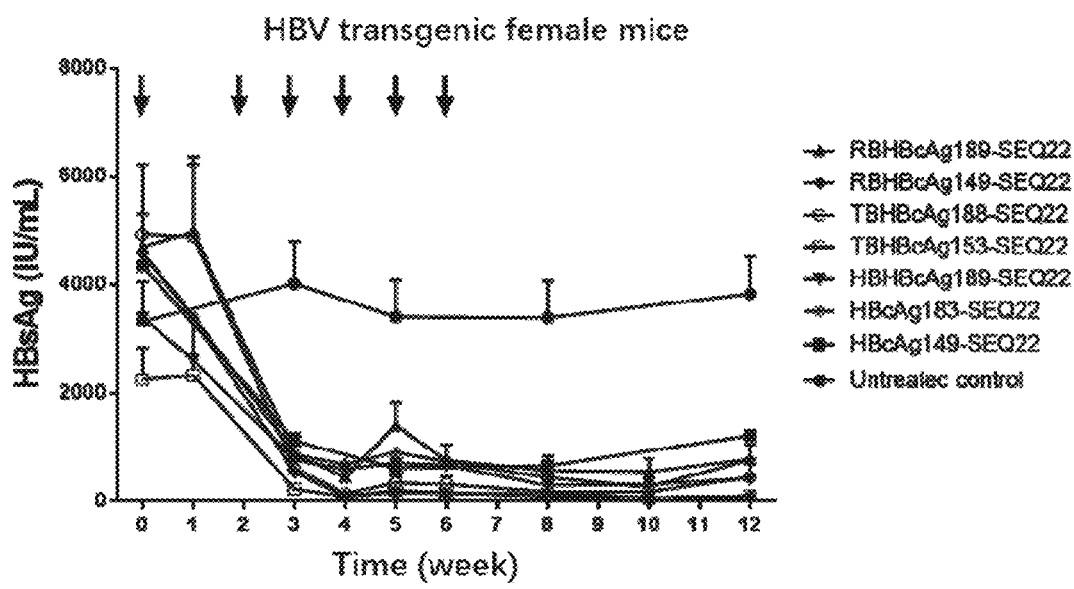
Figure 5:
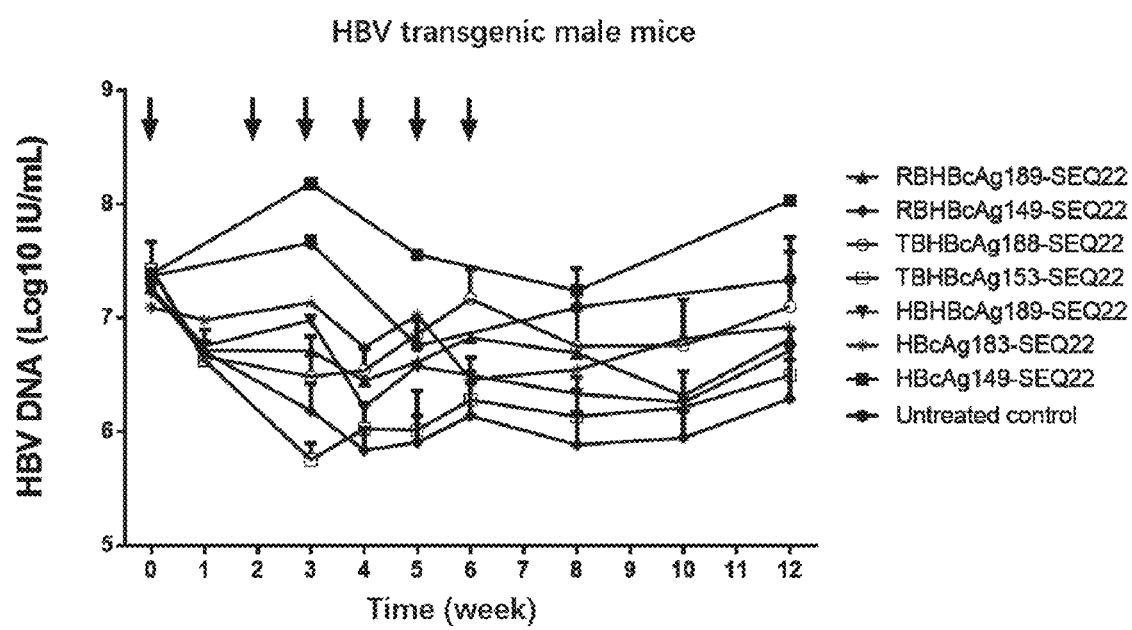
FIG. 5 shows changes in HBV DNA level in mouse sera over time, after the treatment of HBV transgenic male mice with different virus-like particles presenting the same epitope peptide (SEQ ID NO: 22). Longitudinal axis: HBV DNA level (Log 10 IU/ml); horizontal axis: time (week). The arrows indicate the time points of administering virus-like particles to mice.
Figure 6:
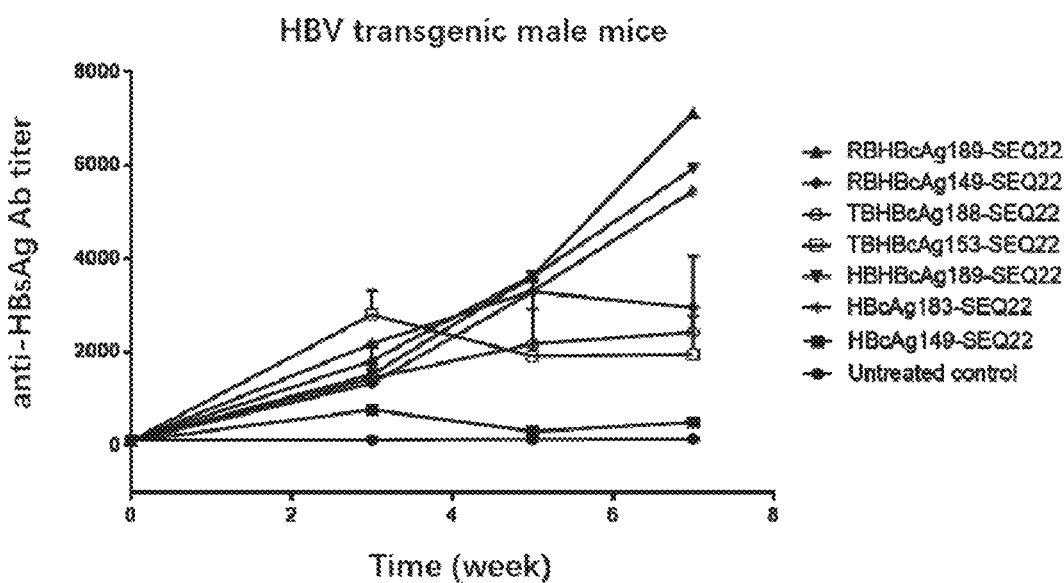
FIG. 6 shows changes in titer of anti-HBsAg antibodies in mouse sera over time, after the treatment of HBV transgenic male (FIG. 6A) and female (FIG. 6B) mice with different virus-like particles presenting the same epitope peptide (SEQ ID NO: 22). Longitudinal axis: the titer of anti-HBsAg antibodies; horizontal axis: time (week).
Figure 6:
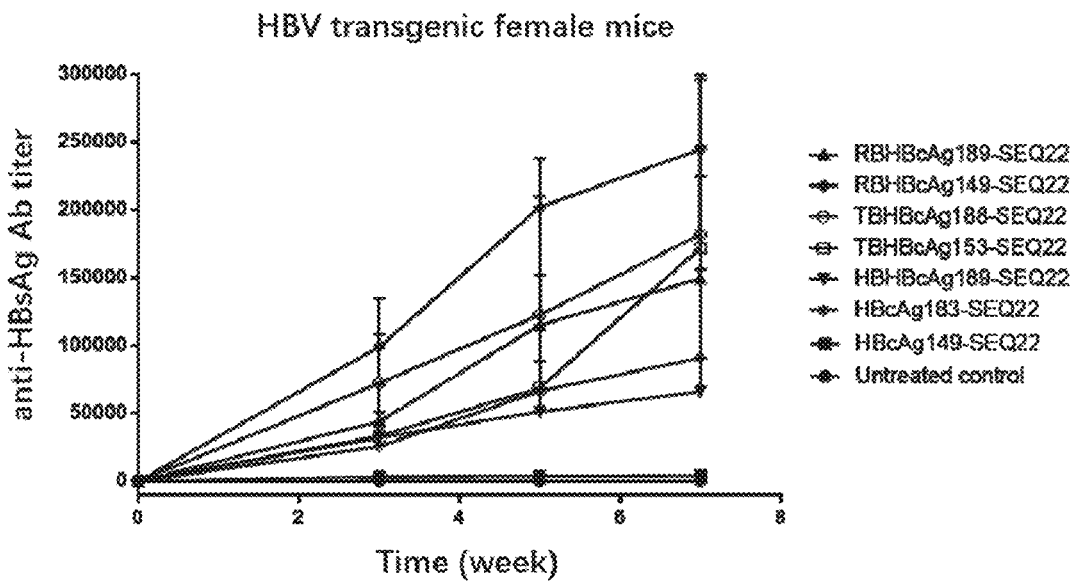

The detection results are shown in FIG. 4-6. FIG. 4 shows changes in HBsAg level in mouse sera over time, after the treatment of HBV transgenic male (FIG. 4A) and female (FIG. 4B) mice with different virus-like particles presenting the same epitope peptide (SEQ ID NO: 22). FIG. 5 shows changes in HBV DNA level in mouse sera over time, after the treatment of HBV transgenic male mice with different virus-like particles presenting the same epitope peptide (SEQ ID NO: 22). FIG. 6 shows changes in titer of anti-HBsAg antibodies in mouse sera over time, after the treatment of HBV transgenic male (FIG. 6A) and female (FIG. 6B) mice with different virus-like particles presenting the same epitope peptide (SEQ ID NO: 22).

The results show that in the groups receiving immunotherapy with VLP, Anti-HBsAg antibodies were detected in mouse sera after immunization, and the level of HBV DNA and HBsAg decreased to different extents in mouse sera. By comparison, no Anti-HBsAg antibodies were generated in the sera of control mice (which were not immunized with VLP), and no decrease in the level of HBV DNA and HBsAg in sera was observed.

These results show that all the 6 polypeptide carriers, constructed based on bat hepatitis B virus core protein, can be used to effectively present the epitope peptide (e.g., HBsAg-aa113-135) of HBsAg from human HBV, can form VLPs, and induce generation of high-titer anti-HBsAg antibodies in organisms, thereby inhibiting the level of HBV DNA and HBsAg (i.e., HBV DNA and HBsAg decreased significantly) in mice. In addition, the experimental data in FIG. 4-6 also shows that the virus-like particles, based on the polypeptide carriers (e.g. RBHBcAg149 and TBHBcAg153) of the invention, have particularly significant anti-HBV therapeutic effects, better than the virus-like particle constructed based on HBcAg of human HBV.

Therefore, the experimental results in the Example show: (1) the polypeptide carriers of the invention can form VLPs, are suitable for presenting various target polypeptides, and can induce generation of high-titer antibodies against target polypeptides in organisms; (2) the polypeptide carriers of the invention are particularly suitable for presenting epitopes of human HBV (e.g., an epitope of HBsAg of human HBV), can induce generation of high-titer antibodies against HBsAg in organisms, and can clean or inhibit the level of HBV DNA and HBsAg in vivo, with an efficacy better than that of the polypeptide carrier constructed based on HBcAg of human HBV. Thus, the recombinant proteins presenting human HBV epitopes according to the invention are potential in treating HBV infection, and are particularly suitable for inducing effective, specific and therapeutic anti-HBV immunization.

Example 5. Preparation and Evaluation of Virus-Like Particles Presenting an Epitope of HBsAg from Different HBV Genotypes The HBsAg epitope (SEQ ID NO: 22) used in Example 2-4 was from HBV genotype B. In order to confirm the broad versatility of the polypeptide carrier of the invention for various HBV genotypes, the inventors also used RBHBcAg149 and TBHBcAg153 as exemplary polypeptide carriers, to construct the recombinant proteins presenting an epitope of HBsAg from different HBV genotypes (genotype A. C and D), and evaluated the ability of the constructed recombinant proteins to be assembled into virus-like particles, the immunogenicity of the virus-like particle produced, and the therapeutic effect thereof against HBV infection.

5.1 Construction of Expression Plasmids Encoding Recombinant Proteins Comprising a Target Polypeptide and a Polypeptide Carrier In the Example, in addition to the HBsAg epitope (from HBV genotype B, SEQ ID NO: 22) used in Example 2-4, the target polypeptide further includes the HBsAg epitope (amino acids from positions 113-135) from HBV genotype A, C and D, designated as: HBsAg-aa113-135-A, HBsAg-aa113-135-C and HBsAg-aa113-135-D. and their sequences (SEQ ID NO: 60-62) are shown in Table 4.

TABLE 4

Sequences of amino acids from positions 113-135 of HBsAg protein fromHBV genotype A, C and D

| SEQ ID NO | Name | Sequence information |
|---|---|---|
| 60 | HBsAg-aa113-135-A | STTTSTGPCKTCTTPAQGNSMFP |

TABLE 4-continued

Sequences of amino acids from positions 113-135 of HBsAg protein fromHBV genotype A, C and D

| SEQ ID NO | Name | Sequence information |
|---|---|---|
| 61 | HBsAg-aa113-135-C | TSTTSTGPCKTCTIPAQGTSMFP |
| 62 | HBsAg-aa113-135-D | SSTTSTGPCRTCTTPAQGTSMYP |

The sense and antisense sequences (as shown in Table 5) coding said 3 target polypeptides were synthesized directly, and annealed, to obtain the gene fragments having cohesive end and encoding the target polypeptides.

TABLE 5

Sense and antisense sequences coding 3 target polypeptides

| SEQ ID NO: | Primer name | Sequence information |
|---|---|---|
| 63 | HBsAg-aa113-135-AF | GATCCTCTACCACCACCTCTACCGGTCCGTG CAAAACCTGCACCACCCCGGCTCAGGGTAAC TCTATGTTCCCGG |
| 64 | HBsAg-aa113-135-AR | AATTCCGGGAACATAGAGTTACCCTGAGCCG GGGTGGTGCAGGTTTTGCACGGACCGGTAGA GGTGGTGGTAGAG |
| 65 | HBsAg-aa113-135-CF | GATCCACCTCTACCACCTCTACCGGTCCGTG CAAAACCTGCACCATCCCGGCTCAGGGTACC TCTATGTTCCCGG |
| 66 | HBsAg-aa113-135-CR | AATTCCGGGAACATAGAGGTACCCTGAGCCG GGATGGTGCAGGTTTTGCACGGACCGGTAGA GGTGGTAGAGGTG |
| 67 | HBsAg-aa113-135-DF | GATCCTCTTCTACCACCTCTACCGGTCCGTG CCGTACCTGCACCACCCCGGCTCAGGGTACC TCTATGTACCCGG |
| 68 | HBsAg-aa113-135-DR | AATTCCGGGTACATAGAGGTACCCTGAGCCG GGGTGGTGCAGGTACGGCACGGACCGGTAGA GGTGGTAGAAGAG |

As described in Example 2, the 3 gene fragments having cohesive end and encoding the target polypeptides as prepared above were ligated to linear vectors RBHBcAg149 and TBHBcAg153, respectively, so as to obtain the expression plasmids encoding the recombinant proteins (6 in total: RBHBcAg149-SEQ60, RBHBcAg149-SEQ61, RBHBcAg149-SEQ62, TBHBcAg153-SEQ60, TBHBcAg153-SEQ61, and TBHBcAg153-SEQ62). The amino acid sequences of the recombinant proteins encoded by the expression plasmids are shown in Table 6.

TABLE 6

Amino acid sequences of 6 recombinant proteins

| SEQ. ID NO: | Recombinant protein | Sequence information |
|---|---|---|
| 69 | RBHBcAg149-SEQ 60 | MDIDPYKEFGASSQLISFLPEDFFPNLAELVET TTALYEEELVGKEHCSPHHTALRSLLNCWGETV RLITWVRNSVEGGGGGSGGGGTGSSTTTSTGPC KTCTTPAQGNSMFPEFGGGGSGGGGSQDAIVQQ VQASVGLRMRQLMWFHLSCLTFGQPTVIEFLVS FGTWIRTPQAYRPPNAPILSTLPEHTIV |
| 70 | RBHBcAg149-SEQ 61 | MDIDPYKEFGASSQLISFLPEDFFPNLAELVET TTALYEEELVGKEHCSPHHTALRSLLNCWGETV RLITWVRNSVEGGGGGSGGGGTGSTSTTSTGPC KTCTIPAQGTSMFPEFGGGGSGGGGSQDAIVQQ VQASVGLRMRQULMWFHLSCLTFGQPTVIEFLV SFGTWIRTPQAYRPPNAPILSTLPEHTIV |
| 71 | RBHBcAg149-SEQ 62 | MDIDPYKEFGASSQLISFLPEDFFPNLAELVET TTALYEEELVGKEHCSPHHTALRSLLNCWGETV RLITWVRNSVEGGGGGSGGGGTGSSSTTSTGPC RTCTTPAQGTSMYPEFGGGGSGGGGSQDAIVQQ VQASVGLRMRQLMWFHLSCLTFGQPVIEFLVSF GTWIRTPQAYRPPNAPILSTLPEHTIV |
| 72 | TBHBc-Ag153-SEQ 60 | MENLERLDIYKEFGVSDVLVSFLPDDFFPTLQQ LLESVNALYEDELTGPNHCSPHHTALRHLIMCG VELRDFIDWMHEQGGGGGSGGGGTGSSTTTSTG PCKTCTTPAQGNSMFPEFGGGGSGGGGSDADAL LAGYLRSKYLKHITKAIWYHLSCLTIFGKQTVH EYLVSFGTWIRTPAAYRPVNAPILTTLPETSVI |
| 73 | TBHBcAg153-SEQ 61 | MENLERLDIYKEFGVSDVLVNSFLPDDFFPTLQ QLLESVNALYEDELTGPNHCSPHHTALRHLIMC GVELRDFIDWMHEQGGGGSGGGGTGSTSTTST GPCKTCTIPAQGTSMFPEFGGGGSGGGGSDADA LLAGYLRSKYLKHITKAIWYHLSCLTFGKQTVH EYLVSFGTWIRTPAAYRPVNAPILTTLPETSVI |
| 74 | TBHBcAg153-SEQ 62 | MENLERLDIYKEFGVSDVLVSFLPDDFFPTLQQ ILESVNALYEDELTGPNHCSPHHTALRHLIMCG VELRDFIDWMHEQGGGGGSGGGGTGSSSTTSTG PCRTCTTPAQGTSMYPEFGGGGSGGGGSDADAL LAGYLRSKYLKHITKAIWYHLSCLTFGKQTVHE YLVSFGTWIRTPAAYRPVNAPILTTLPETSVI |

5.2 Expression, Purification and Assembly of Recombinant Proteins

As described in Example 2, by using the 6 expression plasmids constructed in the previous step, the recombinant proteins encoded by the expression plasmids were expressed and purified. Later, the VLPs formed by the recombinant proteins were observed by Transmission Electron Microscope (TEM).

Figure 7:
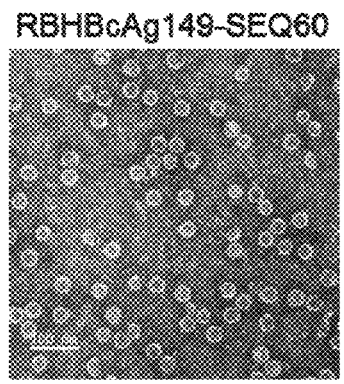
FIG. 7 shows the TEM results of the virus-like particles formed by 6 recombinant proteins constructed in Example 5.
Figure 7:
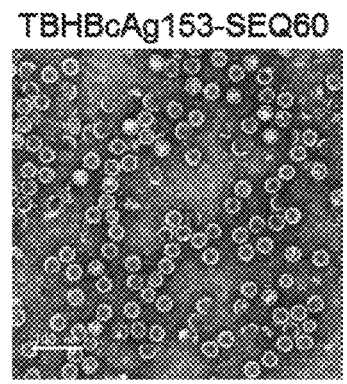
Figure 7:
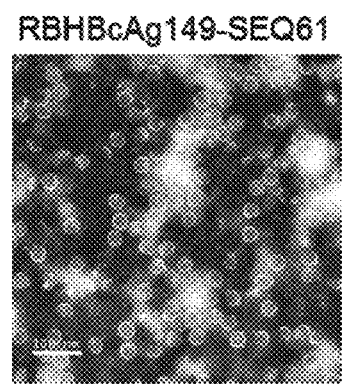
Figure 7:
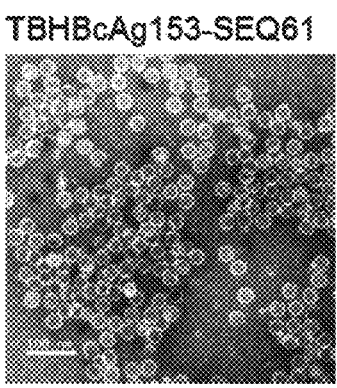
Figure 7:
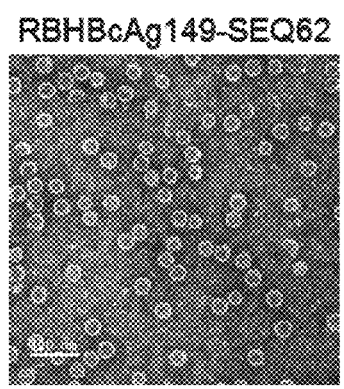
Figure 7:
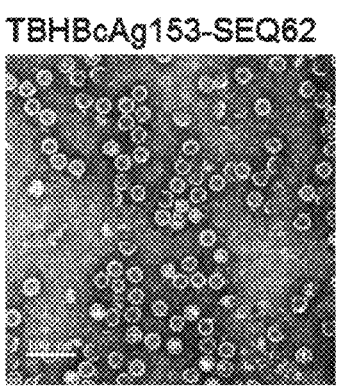

FIG. 7 shows the TEM results of the virus-like particles formed by the 6 recombinant proteins constructed. The results show that all the 6 recombinant proteins obtained can be assembled into virus-like particles with a diameter of about 30 nm. These results show that the polypeptide carriers constructed in the invention have a broad versatility, can be used to present epitope peptides (e.g., aa113-135 of HBsAg protein) from various HBV genotypes, and can form VLPs well.

5.3 Evaluation of Immunogenicity of Virus-Like Particles

By using the method described in Example 3, the virus-like particles, formed by the 6 recombinant proteins as constructed above and the recombinant proteins RBHBcAg149-SEQ22 and TBHBcAg153-SEQ22 in Example 2, were evaluated for their immunogenicity. The experimental results are shown in FIG. 8.

Figure 8:
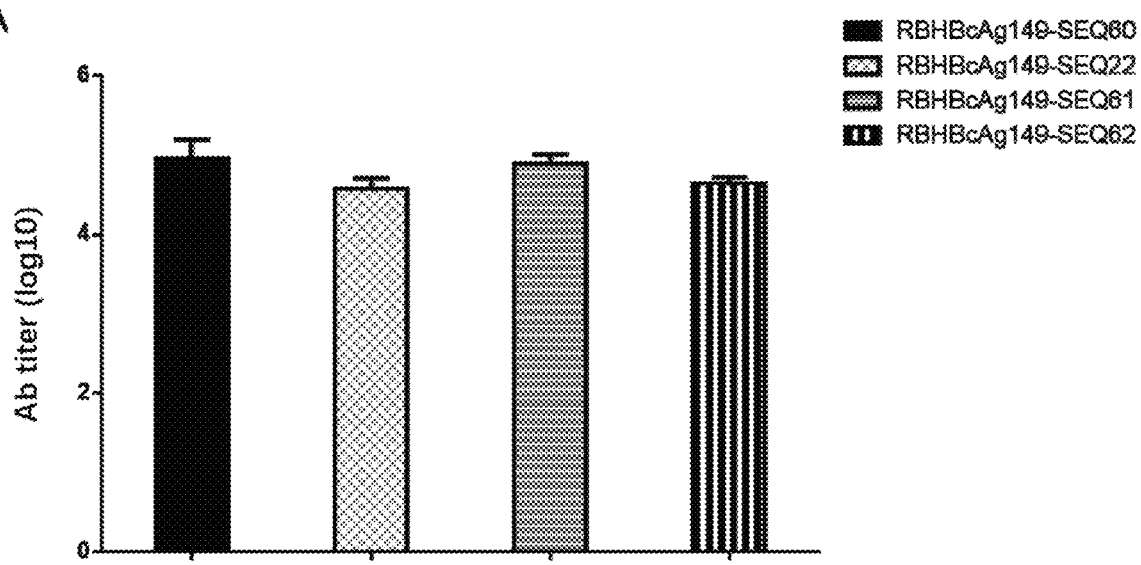
FIG. 8 shows the titers of antibodies against the corresponding target polypeptides (SEQ ID NO: 60, 22, 61, and 62) in mouse sera, three weeks after the immunization of BALB/C mice with the virus-like particles formed by 8 recombinant proteins; wherein the epitope peptide (SEQ ID NO: 60) of HBsAg protein from HBV genotype A was used to determine the antibody titers in sera of mice immunized with RBHBcAg149-SEQ60 and TBHBcAg153-SEQ60; the epitope peptide (SEQ ID NO: 22) of HBsAg protein from HBV genotype B was used to determine the antibody titers in sera of mice immunized with RBHBcAg149-SEQ22 and TBHBcAg153-SEQ22; the epitope peptide (SEQ ID NO: 61) of HBsAg protein from HBV genotype C was used to determine the antibody titers in sera of mice immunized with RBHBcAg149-SEQ61 and TBHBcAg153-SEQ61; and the epitope peptide (SEQ ID NO: 62) of HBsAg protein from HBV genotype D was used to determine the antibody titers in sera of mice immunized with RBHBcAg149-SEQ62 and TBHBcAg153-SEQ62. The results show that all the virus-like particles formed by the 8 recombinant proteins have good immunogenicity, and can induce generation of high-titer antibodies that specifically bind to target antigens in mice.
Figure 8:
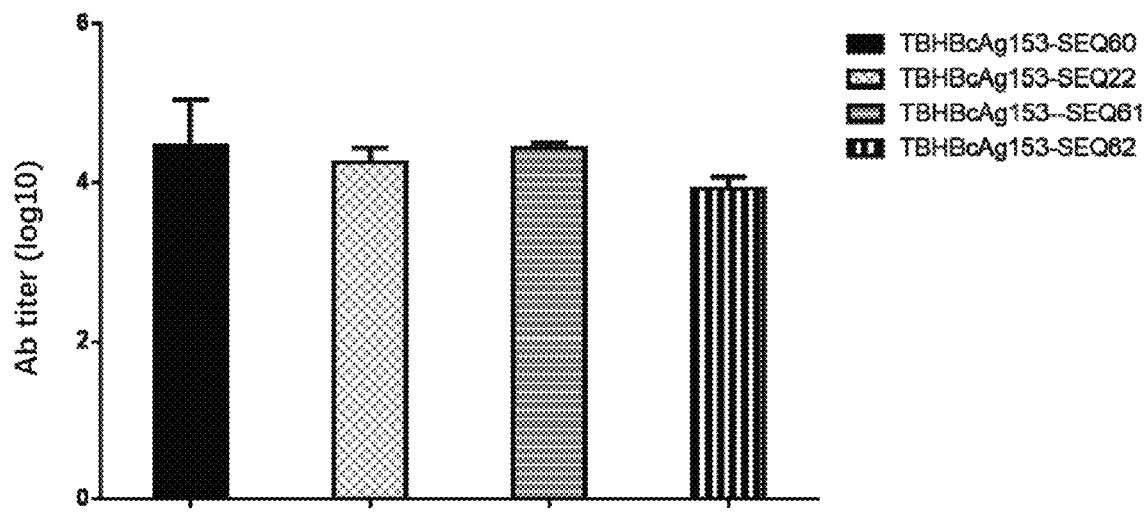

FIG. 8 shows the titers of antibodies against the corresponding target polypeptides (SEQ ID NO: 60, 22, 61, and 62) in mouse sera, three weeks after the immunization of BALB/C mice with the virus-like particles formed by the 8 recombinant proteins; wherein the epitope peptide (SEQ ID NO: 60) of HBsAg protein from HBV genotype A was used to determine the antibody titers in sera of mice immunized with RBHBcAg149-SEQ60 and TBHBcAg153-SEQ60; the epitope peptide (SEQ ID NO: 22) of HBsAg protein from HBV genotype B was used to determine the antibody titers in sera of mice immunized with RBHBcAg149-SEQ22 and TBHBcAg153-SEQ22; the epitope peptide (SEQ ID NO: 61) of HBsAg protein from HBV genotype C was used to determine the antibody titers in sera of mice immunized with RBHBcAg149-SEQ61 and TBHBcAg153-SEQ61; and the epitope peptide (SEQ ID NO: 62) of HBsAg protein from HBV genotype D was used to determine the antibody titers in sera of mice immunized with RBHBcAg149-SEQ62 and TBHBcAg153-SEQ62. The results show that the virus-like particles formed by the 8 recombinant proteins have good immunogenicity, and can induce generation of high-titer antibodies that specifically bind to target epitopes in mice.

5.4 Evaluation on Anti-HBV Therapeutic Effects of Virus-Like Particles

By using the method as described in Example 4, the virus-like particles formed by 4 recombinant proteins (SEQ ID NO: 36, 69, 70, and 71) were evaluated for the anti-HBV therapeutic effects. The experimental results are shown in FIG. 9.

Figure 9:
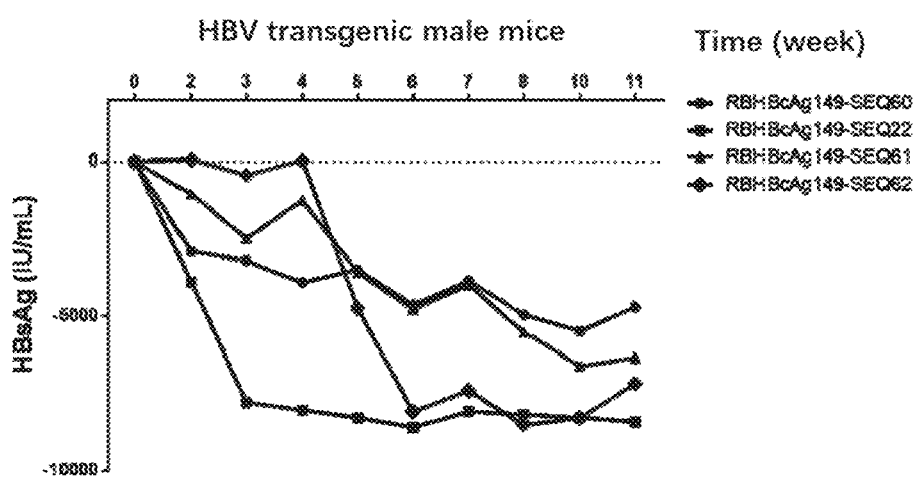
FIG. 9 shows changes in HBsAg level in mouse sera, after the treatment of HBV transgenic male (FIG. 9A) and female (FIG. 9B) mice with the virus-like particles formed by 4 recombinant proteins (SEQ ID NO: 36, 69, 70, and 71), wherein, longitudinal axis: HBsAg level (IU/ml); horizontal axis: time (week).
Figure 9:
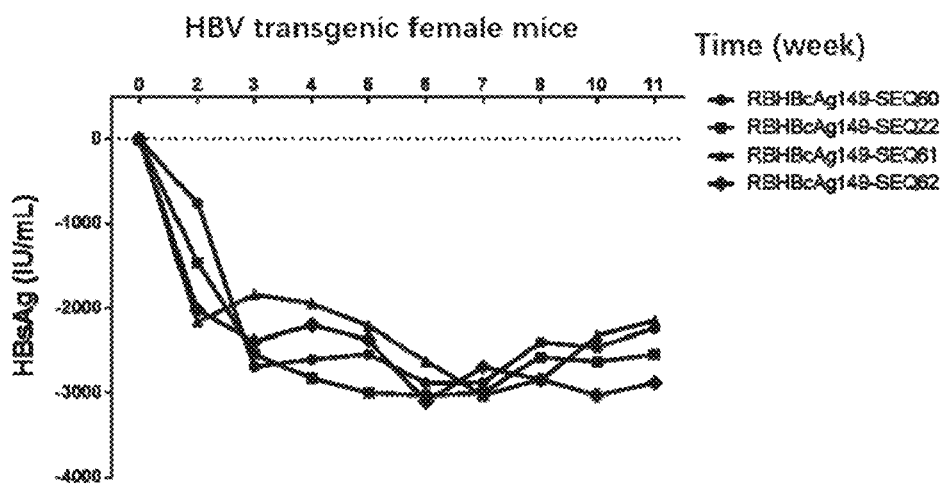
Figure 12:
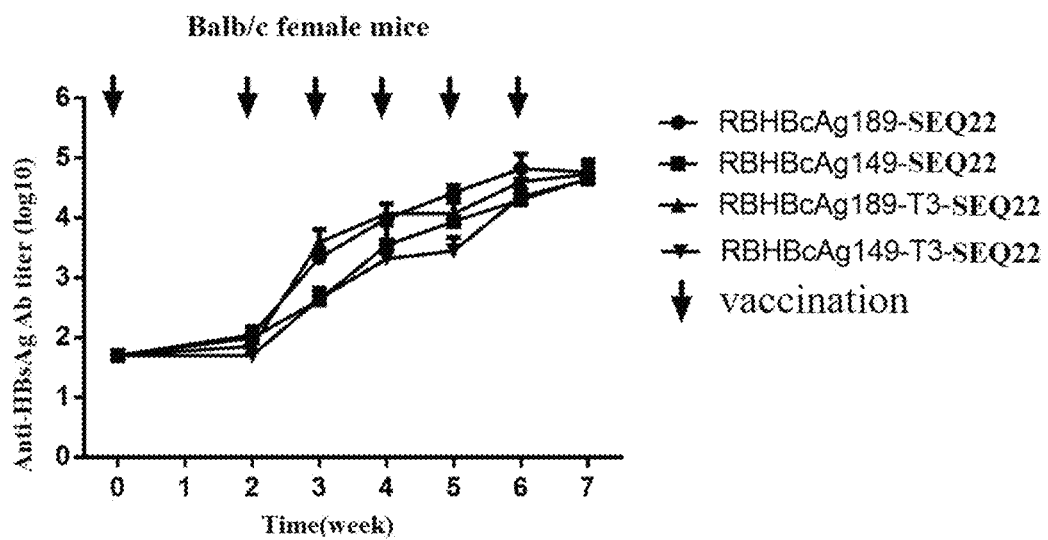
FIG. 12 shows changes in titer of antibodies against the target polypeptide HBsAg in the recombinant proteins in mouse sera over time, after immunization of BALB/C mice with the virus-like particles formed by the recombinant proteins RBHBcAg189-T3-SEQ22 and RBHBcAg149-T3-SEQ22 in Example 7 and the virus-like particles formed by the recombinant proteins RBHBcAg189-SEQ22 and RBHBcAg149-SEQ22 in Example 2, respectively. Longitudinal axis: anti-HBsAg antibody titer (log 10); horizontal axis: time (week). The arrows indicate the time points for administering virus-like particles to mice (vaccination). The results show that all 4 virus-like particles have good immunogenicity and can induce high titers of antibodies that specifically bind to the target antigen HBsAg in mice.
Figure 13:
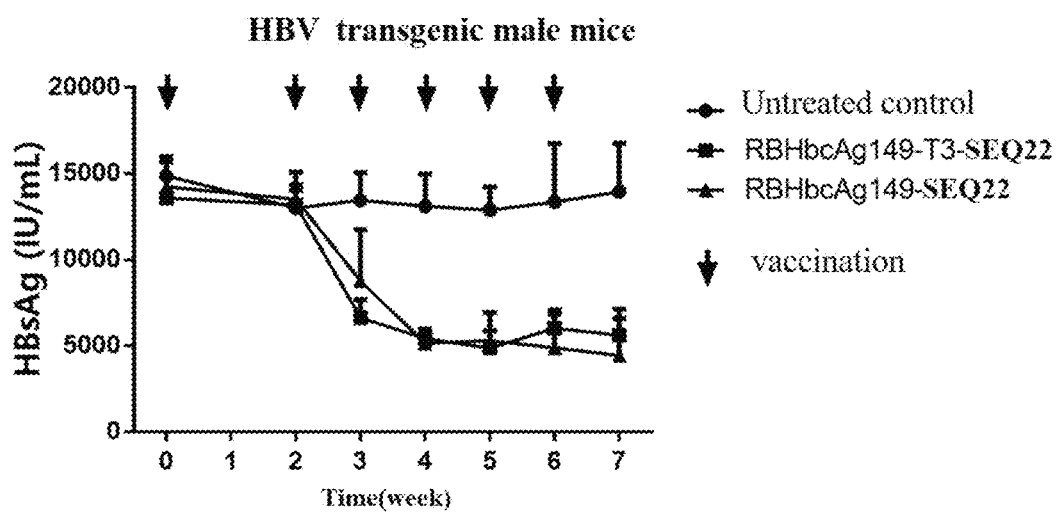
FIG. 13 shows changes in HBsAg level in mouse sera over time, after treatment of HBV transgenic male (FIG. 13A) and female (FIG. 13B) mice with 2 different virus-like particles presenting the same epitope peptide (SEQ ID NO: 22). Longitudinal axis: HBsAg level (IU/ml); horizontal axis: time (week). The arrows indicate the time points for administering virus-like particles to mice (vaccination). The results show that after administration to HBV transgenic mice, both virus-like particles can cause a decrease of the HBsAg level in mouse sera, and the 2 VLPs exhibit comparable effects.
Figure 13:
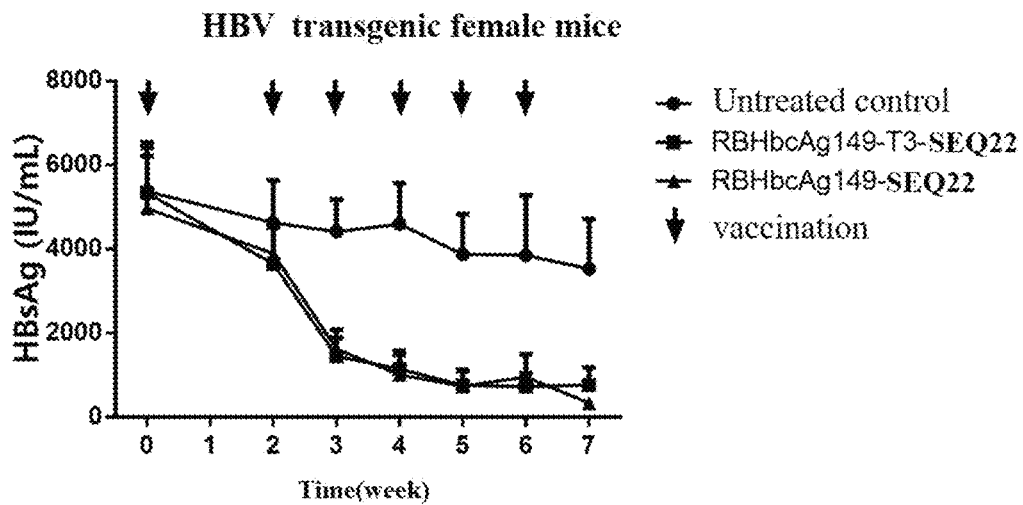
Figure 14:
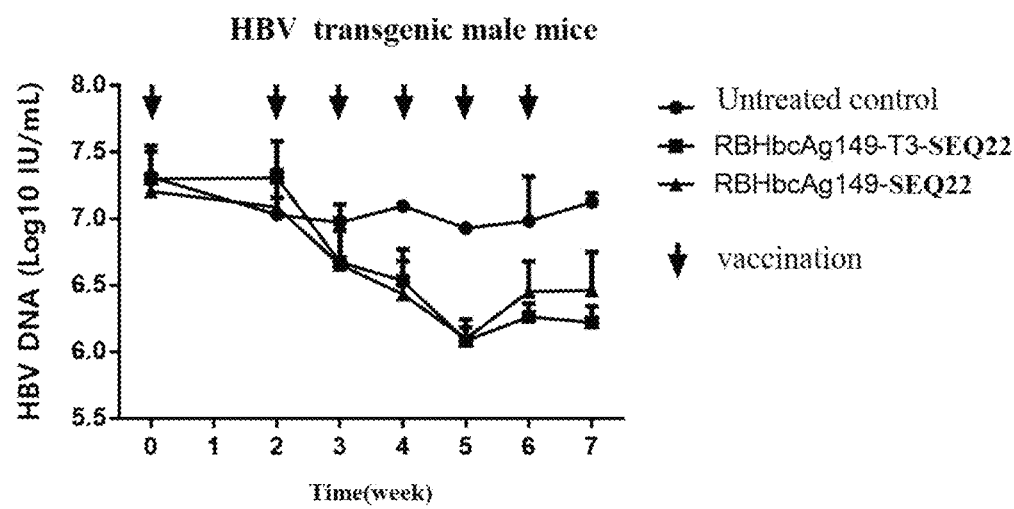
FIG. 14 shows changes in HBV DNA level in mouse sera over time, after treatment of HBV transgenic male (FIG. 14A) and female (FIG. 14B) mice with 2 virus-like particles presenting the same epitope peptide (SEQ ID NO: 22). Longitudinal axis: HBV DNA level (Log 10 IU/ml); horizontal axis: time (week). The arrows indicate the time points for administering virus-like particles to mice (vaccination). The results show that after administration to HBV transgenic mouse, both virus-like particles can cause a decrease in the level of HBV DNA in mouse sera, and the 2 VLPs exhibit comparable effects.
Figure 14:
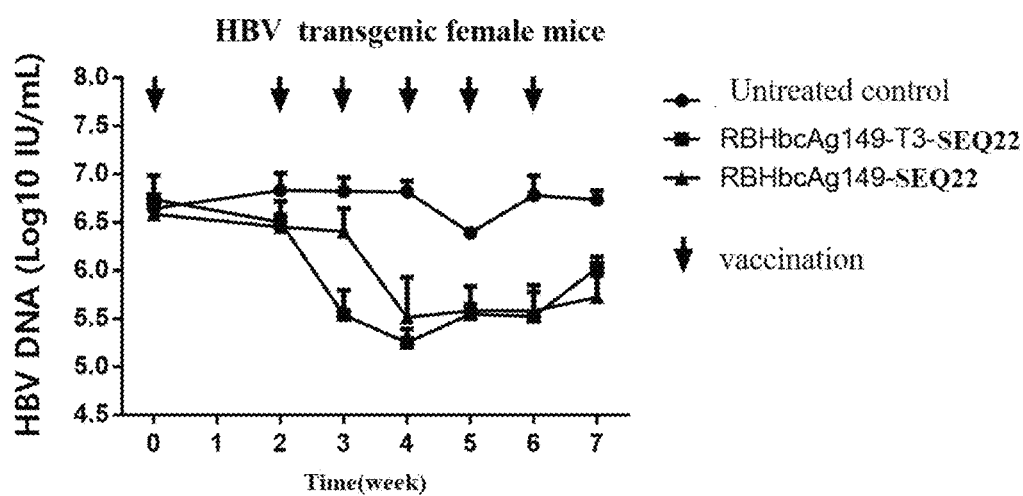
Figure 15:
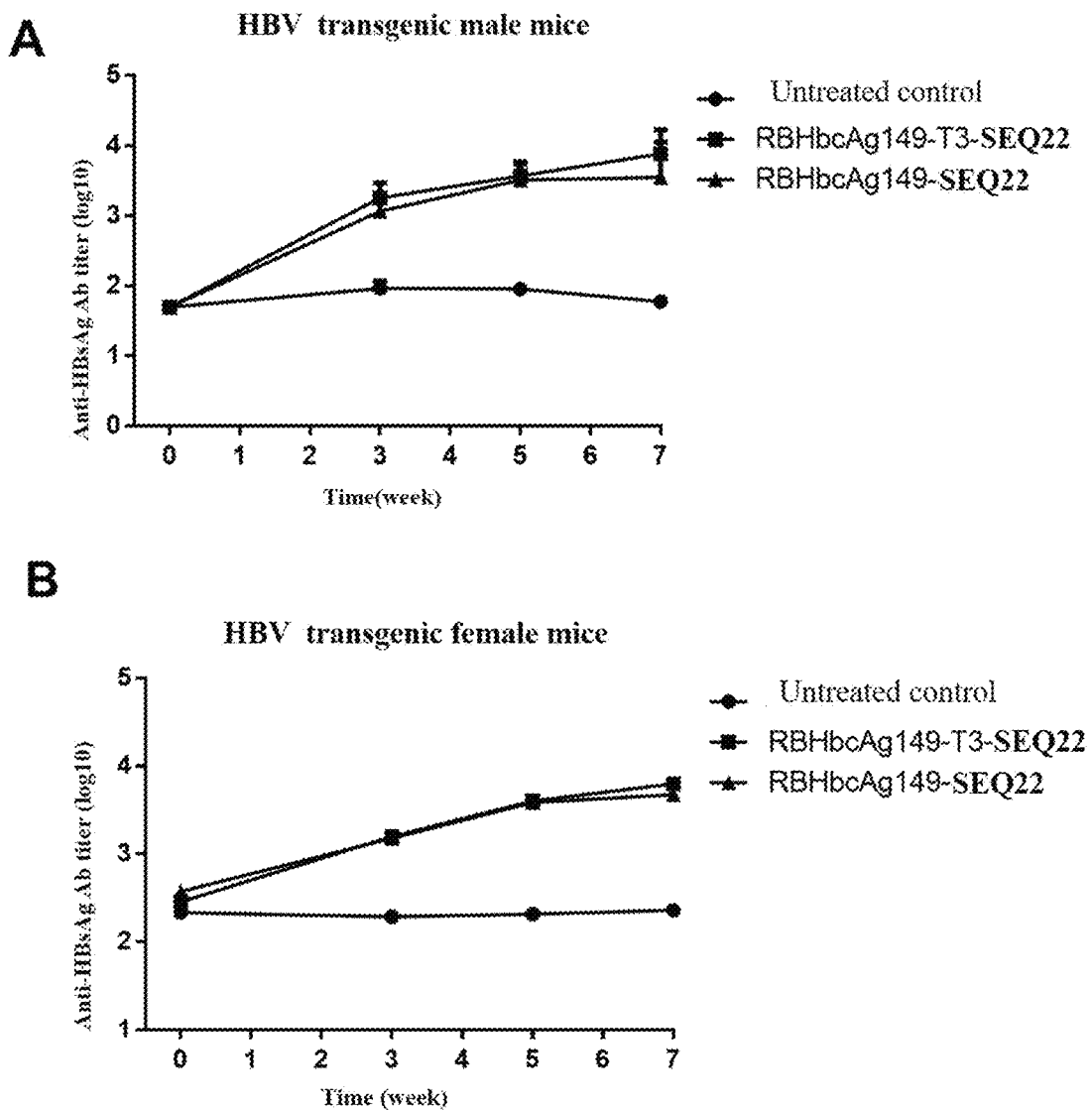
FIG. 15 shows changes in titer of anti-HBsAg antibodies in mouse sera over time, after treatment of HBV transgenic male (FIG. 15A) and female (FIG. 15B) mice with 2 virus-like particles presenting the same epitope peptide (SEQ ID NO: 22). Longitudinal axis: the titer of anti-HBsAg antibodies; horizontal axis: time (week). The results show that after administration to HBV transgenic mice, both virus-like particles can induce high titer anti-HBsAg antibodies in mice, and the 2 VLPs exhibit comparable effects.

FIG. 9 shows changes in HBsAg level in mouse sera over time, after the treatment of HBV transgenic male (FIG. 9A) and female (FIG. 9B) mice with the virus-like particles formed by the 4 recombinant proteins constructed above (RBHBcAg149-SEQ22, RBHBcAg149-SEQ60, RBHBcAg149-SEQ61, and RBHBcAg149-SEQ62; the sequences thereof are SEQ ID NO: 36, 69, 70, and 71, respectively), wherein, longitudinal axis: HBsAg level (IU/ml); horizontal axis: time (week). The results show that in the mice receiving immunotherapy with VLP, the HBsAg level in mouse sera decreased significantly after immunization.

These experimental results show that the polypeptide carriers of the invention (e.g., RBHBcAg149 and TBHBcAg153) can be used to effectively present epitope peptides (e.g., HBsAg-aa113-135) of HBsAg from human HBV of different genotypes (e.g., genotype A, B, C and D). The recombinant proteins, constructed based on the polypeptide carriers of the invention and epitope peptides of HBsAg, can form VLPs, and can induce the generation of high-titer anti-HBsAg antibodies in organisms, thereby inhibiting the HBsAg level (i.e., the HBsAg level decreased significantly) in mice. This indicates that the recombinant proteins comprising the polypeptide carriers of the invention and epitope peptides of HBsAg can be used to prevent and treat the infection by various HBV genotypes, and therefore can be used in the development of new anti-HBV vaccines and medicaments.

Example 6. Construction of Plasmids Encoding a Polypeptide Carrier Carrying a T Cell Epitope In this example, plasmids encoding a polypeptide carrier carrying a T cell epitope are constructed.

6.1 Preparation of Nucleotide Sequences Encoding a Polypeptide Carrier Carrying a T Cell Epitope Based on three bat-derived HBV core antigens (i.e., RBHBcAg protein, TBHBcAg protein, and HBHBcAg protein), the following polypeptide carriers were designed:

RBHBcAg189-T3 carrier, which differs from RBHBcAg protein (SEQ ID NO: 1) in that: the amino acid residues from positions 78-81 of RBHBcAg protein are substituted with a linker set forth in SEQ ID NO: 43; the amino acid residues from positions 18-27 of RBHBcAg protein are substituted with a sequence set forth in SEQ ID NO: 87; the amino acid residues from positions 50-69 of RBHBcAg protein are substituted with a sequence set forth in SEQ ID NO: 88; and the amino acid residues from positions 120-140 of RBHBcAg protein are substituted with a sequence set forth in SEQ ID NO: 89. The amino acid sequence of RBHBcAg189-T3 carrier is set forth in SEQ ID NO: 75, the nucleotide sequence thereof is set forth in SEQ ID NO: 81.

TBHBcAg188-T3 carrier, which differs from TBHBcAg protein (SEQ ID NO: 2) in that: the amino acid residues from positions 80-83 of TBHBcAg protein are substituted with a linker set forth in SEQ ID NO: 43; the amino acid residues from positions 18-27 of TBHBcAg protein are substituted with a sequence set forth in SEQ ID NO: 87; the amino acid residues from positions 54-73 of TBHBcAg protein are substituted with a sequence set forth in SEQ ID NO: 88; the amino acid residues from positions 124-144 of TBHBcAg protein are substituted with a sequence set forth in SEQ ID NO: 89. The amino acid sequence of TBHBcAg188-T3 carrier is set forth in SEQ ID NO: 76, the nucleotide sequence thereof is set forth in SEQ ID NO: 82.

HBHBcAg189-T3 carrier, which differs from HBHBcAg protein (SEQ ID NO: 3) in that: the amino acid residues from positions 78-81 of HBHBcAg protein are substituted with a linker set forth in SEQ ID NO: 43; the amino acid residues from positions 18-27 of HBHBcAg protein are substituted with a sequence set forth in SEQ ID NO: 87; the amino acid residues from positions 50-69 of HBHBcAg protein are substituted with a sequence set forth in SEQ ID NO: 88; the amino acid residues from positions 120-140 of HBHBcAg protein are substituted with a sequence set forth in SEQ ID NO: 89. The amino acid sequence of HBHBcAg189-T3 carrier is set forth in SEQ ID NO: 77, the nucleotide sequence thereof is set forth in SEQ ID NO: 83.

With respect to the nucleotide sequences of said 3 carriers, their whole gene synthesis was performed by Sangon Biotech (Shanghai) Co., Ltd.

6.2 Preparation of Plasmids Encoding a Polypeptide Carrier

By using the synthesized nucleotide sequences (e.g. RBHBcAg189-T3 carrier) as templates, and using the primers set forth in SEQ ID NOs: 45-47, the full-length gene and its truncate (i.e., a gene fragment truncated at C-terminus) of RBHBcAg189-T3 carrier were amplified by PCR. Two PCR products were obtained, i.e., the gene encoding RBHBcAg189-T3 carrier (SEQ ID NO: 81; the amino acid sequence encoded thereby is SEQ ID NO: 75), and the gene encoding RBHBcAg149-T3 carrier (SEQ ID NO: 84; the amino acid sequence encoded thereby is SEQ ID NO: 78).

By a similar method, the following PCR products are obtained: the gene encoding TBHBcAg188-T3 carrier (SEQ ID NO: 82; the amino acid sequence encoded thereby is SEQ ID NO: 76); the gene encoding HBHBcAg189-T3 carrier (SEQ ID NO: 83; the amino acid sequence encoded thereby is SEQ ID NO: 77); the gene encoding TBHBcAg153-T3 carrier (SEQ ID NO: 85; the amino acid sequence encoded thereby is SEQ ID NO: 79); and the gene encoding HBHBcAg149-T3 carrier (SEQ ID NO: 86; the amino acid sequence encoded thereby is SEQ ID NO: 80).

pTO-T7 vector (Luo Wenxin, Zhang Jun, Yang Haijie, et al., Construction and Application of an *Escherichia coli* High Effective Expression Vector with an Enhancer [J], Chinese Journal of Biotechnology, 2000, 16(5): 578-581) was subjected to double enzyme digestion by NdeI and HindIII, to obtain a linear vector. By Gibson assembly cloning method (New England Biolabs (UK) Ltd), the PCR products obtained were ligated to the linear vector, and transformed into DH5a competent bacteria. The transformed bacteria were spread on a plate and cultured, monoclonal colonies were then selected, and the plasmids were extracted and sequenced. It was confirmed by sequencing that 6 plasmids comprising the nucleotide sequences encoding the polypeptide carriers were obtained.

Example 7. Preparation of Recombinant Proteins

Figures 10, 11:
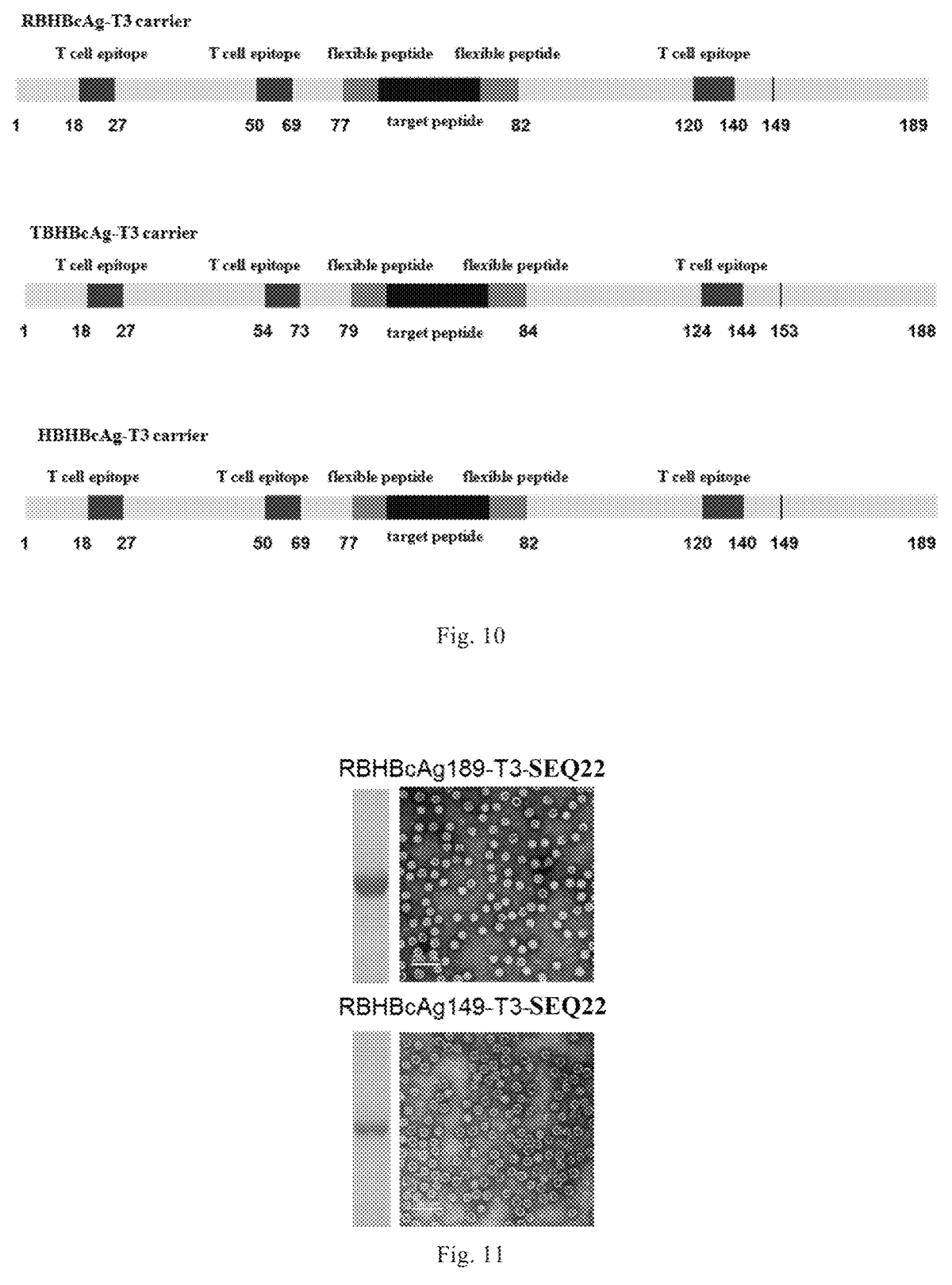

In the Example, a nucleotide sequence encoding a target polypeptide was inserted into the plasmids constructed in Example 6, and a recombinant protein comprising the target polypeptide and the polypeptide carrier was obtained. The scheme of cloning solutions, in which recombinant proteins are constructed by inserting a target polypeptide (a target antigen peptide fragment) into RBHBcAg-T3 carrier, TBHBcAg-T3 carrier and HBHBcAg-T3 carrier of the invention, is shown in FIG. 10.

7.1 Construction of Expression Plasmids Encoding a Recombinant Protein Comprising a Target Polypeptide and a Polypeptide Carrier In the Example, it was verified that the polypeptide carrier carrying a human T cell epitope of the invention could be used to present a target polypeptide. The exemplary target polypeptide used is HBsAg-aa113-135 (i.e., the amino acid residues from positions 113-135 of hepatitis B surface antigen (HBsAg) from human HBV, its amino acid sequence is set forth in SEQ ID NO: 22).

A gene fragment having cohesive ends and encoding the target polypeptide HBsAg-aa113-135 is prepared as described in Example 2. The plasmids RBHBcAg189-T3 and RBHBcAg149-T3 obtained in Example 6 were subjected to double enzyme digestion by BamHI and EcoRI, to obtain 2 linear vectors. Then, the gene fragment having cohesive ends and encoding the target polypeptide, as prepared above, was ligated to each linear vector, respectively, to obtain the expression plasmids encoding the following recombinant proteins: RBHBcAg189-T3-SEQ22 (SEQ ID NO: 90) and RBHBcAg149-T3-SEQ22 (SEQ ID NO: 91).

By a similar method, expression plasmids encoding the following recombinant proteins were obtained: TBHBcAg188-T3-SEQ22 (SEQ ID NO: 92), TBHBcAg153-T3-SEQ22 (SEQ ID NO: 93), HBHBcAg189-T3-SEQ22 (SEQ ID NO: 94) and HBHBcAg149-T3-SEQ22 (SEQ ID NO: 95).

7.2 Expression, Purification and Assembly of Recombinant Proteins

The recombinant proteins encoded by the expression plasmids as prepared above were expressed and purified via the method described in Example 2.2, and used to assemble VLP.

FIG. 11 shows the SDS-PAGE results of 2 recombinant proteins constructed (RBHBcAg189-T3-SEQ22 and RBHBcAg149-T3-SEQ22), and the Transmission Electron Microscope (TEM) results of the virus-like particles formed by the recombinant proteins. The results showed that both recombinant proteins obtained had a purity greater than 85% and could be assembled into virus-like particles with a diameter of about 30 nm.

In addition, by the above method, it could be confirmed that the recombinant proteins TBHBcAg188-T3-SEQ22, TBHBcAg153-T3-SEQ22, HBHBcAg189-T3-SEQ22, and HBHBcAg149-T3-SEQ22 could also be assembled into well-formed virus-like particles.

These results show that the polypeptide carriers carrying T cell epitopes constructed by the invention can be used for presenting a target polypeptide and can form VLP.

Example 8. Evaluation on Immunogenicity of Virus-Like Particles

In the Example, the inventors verified the immunogenicity of the virus-like particles formed by the recombinant proteins prepared in Example 7. All such virus-like particles can induce generation of antibodies that specifically bind to target antigen in organisms.

8.1 Immunization of Mice

BALB/C mice were immunized with the 2 virus-like particles (RBHBcAg189-T3-SEQ22 and RBHBcAg149-T3-SEQ22) prepared in Example 7 and the 2 virus-like particles (RBHBcAg189-SEQ22 and RBHBcAg149-SEQ22) prepared in Example 2, respectively. The immunization process was as following: the immunoadjuvant used was aluminum hydroxide adjuvant; the immunizing dose was 3 ug/dose; the immunization was performed by intramuscular injection at lateral thigh of hindlimb; the immune procedure was immunization once each at Week 0, 2, 3, 4, 5 and 6, 6 times in total.

8.2 Detection of Titer of Antibodies that Specifically Bind to the Target Antigen in Sera 8.2.1 Preparation of Reaction Plates The antigen for coating reaction plate was the target antigen corresponding to the target polypeptide SEQ22, i.e., human hepatitis B virus surface antigen recombinantly expressed in CHO cells (HBsAg, purchased from Beijing Wantai Biological Pharmacy).

HBsAg protein was diluted with 50 mM CB buffer of pH9.6 ($NaHCO_3$/$Na_2CO_3$ buffer, at a final concentration of 50 mM, pH=9.6), at a final concentration of 2 μg/mL, to obtain the coating solution. To each well of a 96-well ELISA plate, 100 μL coating solution was added, and the wells were coated at 2-8° C. for 16-24 h, and then further coated at 37° C. for 2 h. Later, PBST washing solution (20 mM PB7.4, 150 mM NaCl, 0.1% Tween20) was used to wash wells once; and 200 μL blocking solution (20 mM $Na_2HPO_4$/$NaH_2PO_4$ buffer solution containing 20% bovine calf serum and 1% casein, pH=7.4) was then added to each well, and the wells were blocked at 37° C. for 2 h. The blocking solution was discarded. After that, the ELISA plate was dried, and packaged into an aluminum foil bag, which was stored at 2-8° C. for further use.

8.2.2 ELISA detection of Anti-HBsAg antibody titer in serum Collection of serum samples: blood was collected from the eye orbit of mice at Week 0, 2, 3, 4, 5, 6 and 7, the serum was separated and cryopreserved at −20° C., until detection.

Sample dilution: a mouse serum was diluted with PBS solution containing 20% newborn bovine serum at 7 dilution gradients, i.e. 1:100, 1:500, 1:2500, 1:12500, 1:62500, 1:312500, and 1:1562500.

ELISA detection: to each well of the coated ELISA plate, 100 μL diluted serum sample was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 100 μL GAM-HRP reaction solution was added, and incubated at 37° C. for 30 min. The ELISA plate was then washed with PBST washing solution (20 mM PB7.4, 150 mM NaCl, 0.1% Tween20) for five times. After washing, to each well of the ELISA plate, 50 μL TMB color developing agent (provided by Beijing Wantai Biological Pharmacy) was added, and incubated at 37° C. for 15 min. After the incubation, to each well of the ELISA plate, 50 μL stop solution (provided by Beijing Wantai Biological Pharmacy) was added, and the OD450/630 value for each well was read by an ELISA instrument.

Calculation of antibody titer: samples, the read values of which were within 0.2-2.0, were analyzed; a regression curve was plotted with the dilution fold and the read value, and the dilution fold of the sample, at which the read value was 2-fold of the background value, was calculated, and the dilution fold of the sample was used as the titer of the specific antibody in serum.

FIG. 12 shows changes in titer of antibodies against the target antigen HBsAg in mouse sera over time, after immunization of BALB/C mice with the virus-like particles formed by the 4 recombinant proteins, respectively. The results show that all the virus-like particles formed by the 4 recombinant proteins have good immunogenicity, and can induce the generation of high-titer antibodies that specifically bind to the target antigen HBsAg in mice. In addition, the results show that the immunogenicity of the virus-like particles RBHBcAg189-T3-SEQ22 and RBHBcAg149-T3-SEQ22 prepared in Example 7 in mice is comparable to that of virus-like particles RBHBcAg189-SEQ22 and RBHBcAg149-SEQ22 prepared in Example 2.

By a similar method, it was verified that virus-like particles TBHBcAg188-T3-SEQ22, TBHBcAg153-T3-SEQ22, HBHBcAg189-T3-SEQ22, HBHBcAg149-T3-SEQ22 have good immunogenicity.

The results show that the polypeptide carrier carrying a T cell epitope of the invention is suitable for presenting a target polypeptide, can form VLP; and the virus-like particle formed by the recombinant protein comprising the polypeptide carrier carrying a T cell epitope and the target polypeptide can induce generation of high-titer antibodies that specifically bind to the target polypeptide in an organism.

Example 9. Evaluation on Anti-HBV Therapeutic Effects of Virus-Like Particles Presenting the HBsAg Epitope (SEQ ID NO: 22)

In the Example, the inventors evaluated the anti-HBV therapeutic effects of the virus-like particles presenting the same epitope peptide (SEQ ID NO: 22), as constructed based on different polypeptide carriers.

9.1 Immunization of Mice

As described in Example 4, the virus-like particle RBHBcAg149-T3-SEQ22 prepared in Example 7 and the virus-like particle RBHBcAg149-SEQ22 prepared in Example 2 (2 virus-like particles presenting an epitope of HBsAg (SEQ ID NO: 22)) were evaluated for the anti-HBV therapeutic effects in an HBV transgenic mouse model.

The immunization method was as followed: the immunoadjuvant used was aluminum hydroxide adjuvant; and the immunizing dose was 12 μg/dose; the immunization was performed by intramuscular injection at lateral thigh of hindlimb; the immune procedure was immunization once each at Week 0, 2, 3, 4, 5, and 6, 6 times in total.

9.2 Detection of Antibody Titer and Virological Index in Serum

According to the method as described in Example 3.2, the Anti-HBsAg antibody titer in serum was determined, and the virological index (i.e., the level of HBV DNA and HBsAg) in mouse serum was determined.

9.3 Analysis of Therapeutic Effects of Recombinant Proteins

The detection results are shown in FIG. 13-15. FIG. 13 shows changes of HBsAg level in mouse sera over time, after treatment of HBV transgenic male (FIG. 13A) and female (FIG. 13B) mice with different virus-like particles presenting the same epitope peptide (SEQ ID NO: 22). FIG. 14 shows changes of HBV DNA level in mouse sera over time, after treatment of HBV transgenic male (FIG. 14A) and female (FIG. 14B) mice with different virus-like particles presenting the same epitope peptide (SEQ ID NO: 22). FIG. 15 shows changes of titer of anti-HBsAg antibodies in mouse sera over time, after treatment of HBV transgenic male (FIG. 15A) and female (FIG. 15B) mice with different virus-like particles presenting the same epitope peptide (SEQ ID NO: 22).

The results show that in the groups receiving immunotherapy with the virus-like particle RBHBcAg149-T3-SEQ22 or the virus-like particle RBHBcAg149-SEQ22, after immunization, significant levels of Anti-HBsAg antibodies were detected in mouse sera, and the level of HBV DNA and HBsAg in mouse sera decreased significantly, and the efficacy of the two virus-like particles was comparable. In contrast, no Anti-HBsAg antibody was generated in the sera of control mice (which were not immunized with VLP), and no decrease in the level of HBV DNA and HBsAg in sera was observed.

By a similar method, it is verified that virus-like particles RBHBcAg189-T3-SEQ22, TBHBcAg188-T3-SEQ22, TBHBcAg153-T3-SEQ22, HBHBcAg189-T3-SEQ22, and HBHBcAg149-T3-SEQ22 have good immunogenicity.

These results show that all the polypeptide carriers carrying T cell epitopes, constructed based on bat hepatitis B virus core protein, can be used to effectively present the epitope peptide (e.g., HBsAg-aa113-135) of HBsAg from human HBV, can form VLPs, and induce generation of high-titer anti-HBsAg antibodies in hosts, thereby inhibiting the level of HBV DNA and HBsAg (i.e., HBV DNA and HBsAg decreased significantly) in mice. In addition, the experimental data in FIG. 13-15 also show that the virus-like particles RBHBcAg149-T3-SEQ22 and RBHBcAg149-SEQ22 had comparable anti-HBV therapeutic effects. Combined with the experimental results of FIG. 4-6 in Example 4, it can be seen that the virus-like particles based on the polypeptide carriers carrying T cell epitopes of the invention (e.g. RBHBcAg149-T3) have particularly significant anti-HBV therapeutic effects, which is superior to the virus-like particle constructed based on HBcAg of human HBV.

Therefore, the experimental results in the Example show: (1) the polypeptide carrier carrying a T cell epitope of the invention can form VLPs, is suitable for presenting a target polypeptide, and can induce generation of high-titer antibodies against the target polypeptide in an organism; (2) the polypeptide carrier carrying a T cell epitope of the invention is particularly suitable for presenting an epitope of human HBV (e.g., an epitope of HBsAg of human HBV), can induce generation of high-titer antibodies against HBsAg in an organism, and can clean or inhibit the level of HBV DNA and HBsAg in vivo, with an efficacy better than that of the polypeptide carrier constructed based on HBcAg of human HBV. Thus, the recombinant protein presenting a human HBV epitope according to the invention are potential in treating HBV infection, and is particularly suitable for inducing effective, specific and therapeutic anti-HBV immunization.

Example 10. Evaluation of Ability of a Virus-Like Particle Based on a Polypeptide Carrier Carrying a T Cell Epitope to Stimulate Immune Cells to Secrete IFNγ

In the Example, we evaluated the ability of virus-like particles based on a polypeptide carrier carrying a T cell epitope to stimulate immune cells to secrete IFNγ. Briefly, the virus-like particle RBHBcAg149-T3-SEQ22 prepared in Example 7 and the virus-like particle RBHBcAg149-SEQ22 prepared in Example 2 were incubated with whole blood samples obtained from hepatitis B patients, respectively, and then the level of IFNγ in the whole blood samples was detected, so as to evaluate the ability of the virus-like particles to stimulate the immune cells in the whole blood samples of hepatitis B patients to secrete IFNγ.

10.1 Co-Culture of Virus-Like Particles and Whole Blood Samples

Whole blood samples were collected from hepatitis B patients (26) and dispensed into three 1.5 mL EP tubes (500 μL per tube) and incubated respectively with virus-like particles RBHBcAg149-T3-SEQ22, RBHBcAg149-SEQ22 and PBS (used as a negative control, no toxoid) for 24 hours at 37° C. (at a final protein concentration of 2 μg/mL). After the incubation, the whole blood sample was centrifuged at 4000 rpm for 5 minutes, and the supernatant was collected for the next test.

10.2 Detection of IFNγ

According to the manufacturer's instructions, the MIL-LIPLEX MAP-Human Cell Signaling Portfolio, a human cytokine assay kit purchased from Millipore, was used to determine IFNγ levels in the supernatant samples. The results are shown in FIG. 16.

Figure 16:
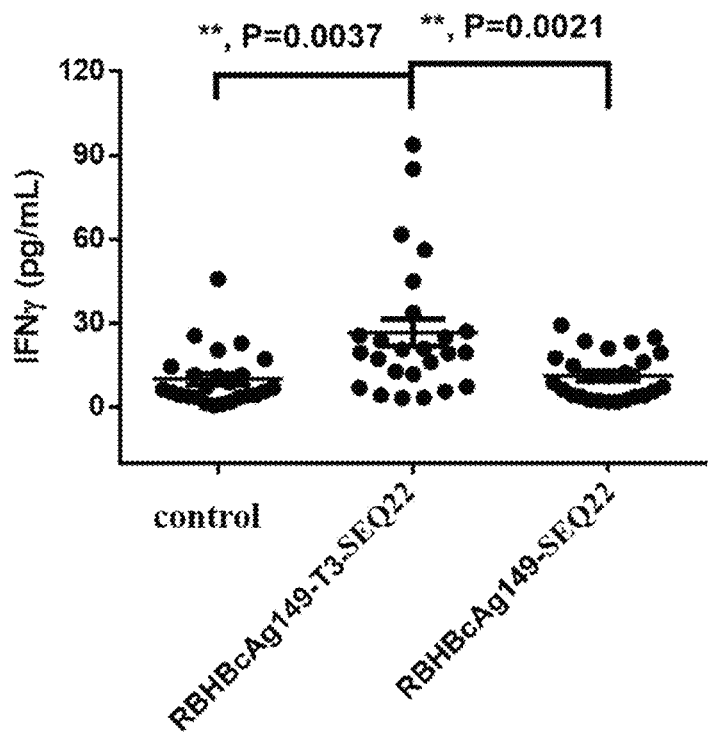
FIG. 16 shows the level of IFNγ secreted in the whole blood samples after incubating the whole blood samples obtained from hepatitis B patients with the virus-like particle RBHBcAg149-T3-SEQ22 or the virus-like particle RBHBcAg149-SEQ22. The results show that the level of IFNγ in the whole blood samples incubated with RBHBcAg149-T3-SEQ22 is significantly higher than that in the whole blood samples incubated with RBHBcAg149-SEQ22 (p=0.0021) or PBS (p=0.0037).

FIG. 16 shows the level of IFNγ secreted in the whole blood samples after incubation of the whole blood samples obtained from hepatitis B patients with the virus-like particle RBHBcAg149-T3-SEQ22 or the virus-like particle RBHBcAg149-SEQ22. The results show that the level of IFNγ in the whole blood samples incubated with RBHBcAg149-T3-SEQ22 was significantly higher than that in the whole blood samples incubated with RBHBcAg149-SEQ22 (p=0.0021) or PBS (p=0.0037).

By a similar method, it could be verified that the virus-like particles RBHBcAg189-T3-SEQ22, TBHBcAg188-T3-SEQ22, TBHBcAg153-T3-SEQ22, HBHBcAg189-T3-SEQ22 and HBHBcAg149-T3-SEQ22 can also stimulate secretion of IFNγ by immune cells in whole blood samples obtained from hepatitis B patients.

These results show that the polypeptide carrier carrying a human T cell epitope of the present invention and the recombinant protein/viral-like particle constructed based thereon can stimulate secretion of IFNγ by human immune cells, thus can enhance the immune response of human body to the recombinant protein/virus-like particle comprising the polypeptide carrier and the target polypeptide. The polypeptide carrier carrying a human T cell epitope of the present invention has a significant advantage in enhancing the response of human T cells.

Example 11. Preparation, Expression, Purification and Assembly of Recombinant Proteins Constructed Based on a Polypeptide Carrier without a Linker In the Example, the inventors used a polypeptide carrier without a linker to present a target polypeptide, so as to obtain a recombinant protein comprising the target polypeptide and the polypeptide carrier without the linker. Further, the inventors also studied the ability of the recombinant protein obtained to assemble into VLPs.

Briefly, based on the expression plasmid encoding the recombinant protein RBHBcAg149-T3-SEQ22 obtained in Example 7, an expression plasmid expressing the recombinant protein RBHBcAg149n-T3-SEQ22 (having an amino acid sequence set forth in SEQ ID NO: 96) was constructed, wherein the recombinant protein RBHBcAg149n-T3-SEQ22 differs from the recombinant protein RBHBcAg149-T3-SEQ22 in that: the flexible linkers located at both ends of the target polypeptide SEQ22 are deleted. The construction method of the expression plasmid encoding the recombinant protein RBHBcAg149n-T3-SEQ22 is as follows.

By using the expression plasmid encoding the recombinant protein RBHBcAg149-T3-SEQ22 as a template, PCR is performed using the first primer pair RBc149nF1 (SEQ ID NO: 97) and RBc149nR1 (SEQ ID NO: 98) to obtain the first amplification product; and PCR is performed using the second primer pair RBc149nF2 (SEQ ID NO: 99) and RBc149nR2 (SEQ ID NO: 100) to obtain the second amplification product. Subsequently, by using the first amplification product and the second amplification product together as templates, PCR is performed using primers RBc149nF1 (SEQ ID NO: 97) and RBc149nR2 (SEQ ID NO: 100) to obtain the third amplification product, i.e., a nucleic acid fragment encoding the recombinant protein RBHBcAg149n-T3-SEQ22.

TABLE 7 primer sequences

| SEQ ID NO: | Primer name | sequences |
|---|---|---|
| 97 | RBc149nF1 | AACTTTAAGAAGGAGATATACATATGGACATCG ACCCGTACAAAGAATTC |
| 98 | RBc149nR1 | GAGVIGTGCAGGTTTTGCATGGTCCGGTGCTGG YMITGATGAACCVICAACAGAGTTAC |
| 99 | RBc149nF2 | CAAAACCTGCACAACTCCTGCTCAAGGAACCTC TATGTTTCCCCAGGACGCTATCGTTCA |
| 100 | RBc149nR2 | TGGTGCTCGAGTGCGGCCGCAAGCTTAGATAAC GGTGTGTTCCGGCAGGGTAG | pTO-T7 vector was subjected to double enzyme digestion by NdeI and HindIII, to obtain a linear vector. By Gibson assembly cloning method (New England Biolabs (UK) Ltd), the third amplification product obtained was ligated to the linear vector, and transformed into ER2566 competent bacteria. The transformed bacteria were spread on a plate and cultured, monoclonal colonies were then selected, and the plasmids were extracted and sequenced. It was confirmed by sequencing that an expression plasmid with the nucleotide fragment encoding the recombinant protein RBHBcAg149n-T3-SEQ22 was obtained.

Subsequently, the recombinant protein RBHBcAg149n-T3-SEQ22 was expressed and purified according to the method described in Section 2.2 of Example 2, and the purified recombinant protein was detected by SDS-PAGE and the VLPs formed by the recombinant protein was observed by the Transmission Electron Microscope. The experimental results were shown in FIG. 17.

Figure 17:
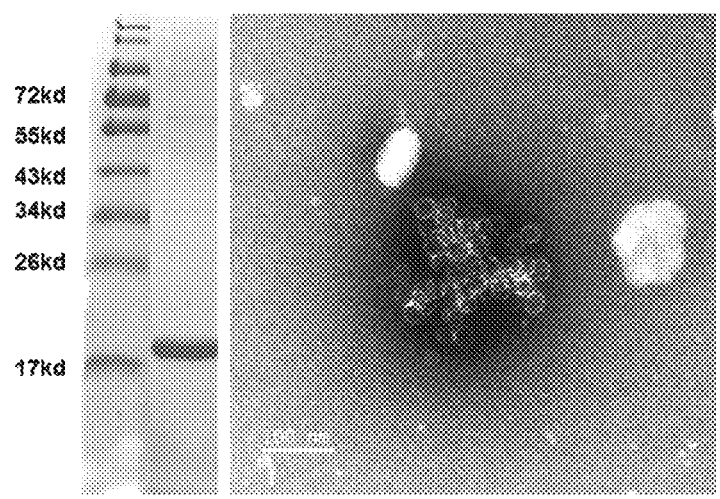
FIG. 17 shows the SDS-PAGE results of the purified recombinant protein RBHBcAg149n-T3-SEQ22, and the Transmission Electron Microscope results of the virus-like particles formed by said recombinant protein.

FIG. 17 shows the SDS-PAGE results of the purified recombinant protein RBHBcAg149n-T3-SEQ22 and the Transmission Electron Microscope observations of the virus-like particles formed from the recombinant protein. The results show that the recombinant protein obtained has a purity greater than 85%, and can be assembled into virus-like particles with a diameter of about 30 nm. These results show that the polypeptide carrier without a linker constructed by the invention can be used to present a target polypeptide and can form VLP.

Although the embodiments of the invention have been described in detail, a person skilled in the art would understand that according to all the disclosed teachings, details can be amended and modified, and these alterations all fall into the protection scope of the invention. The scope of the invention is defined by the attached claims and any equivalent thereof.

The invention claimed is:

1. A nucleic acid molecule, comprising a nucleotide sequence encoding a polypeptide carrier, wherein the polypeptide carrier is selected from the following polypeptide carriers:
  (1) RBHBcAg-T carrier, which differs from roundleaf bat HBV core antigen protein (RBHBcAg protein) by difference comprising the following:
    (1a) one or more amino acid residues of the amino acid residues from positions 78-83 at N-terminus of RBHBcAg protein are deleted or substituted with a linker;
    (1b) one or more amino acid residues of the amino acid residues from positions 18-27, one or more amino acid residues of the amino acid residues from positions 50-69 and/or one or more amino acid residues of the amino acid residues from positions 120-140 at N-terminus of RBHBcAg protein are each independently substituted with a human T cell epitope; and
    (1c) optionally, 1-5, 5-10, 10-15, 15-20, 20-25, 25-30, 30-35, or 35-40 amino acid residues are deleted at C-terminus of RBHBcAg protein;
  (2) TBHBcAg-T carrier, which differs from tent-making bat HBV core antigen protein (TBHBcAg protein) by difference comprising the following:
    (2a) one or more amino acid residues of the amino acid residues from positions 80-84 at N-terminus of TBHBcAg protein are deleted or substituted with a linker;
    (2b) one or more amino acid residues of the amino acid residues from positions 18-27, one or more amino acid residues of the amino acid residues from positions 54-73 and/or one or more amino acid residues of the amino acid residues from positions 124-144 at N-terminus of TBHBcAg protein are each independently substituted with a human T cell epitope; and
    (2c) optionally, 1-5, 5-10, 10-15, 15-20, 20-25, 25-30, or 30-35 amino acid residues are deleted at C-terminus of TBHBcAg protein; and
  (3) HBHBcAg-T carrier, which differs from horseshoe bat HBV core antigen protein (HBHBcAg protein) by difference comprising the following:
    (3a) one or more amino acid residues of the amino acid residues from positions 78-83 at N-terminus of HBHBcAg protein are deleted or substituted with a linker;
    (3b) one or more amino acid residues of the amino acid residues from positions 18-27, one or more amino acid residues of the amino acid residues from positions 50-69 and/or one or more amino acid residues of the amino acid residues from positions 120-140 at N-terminus of HBHBcAg protein are each independently substituted with a human T cell epitope; and
    (3c) optionally, 1-5, 5-10, 10-15, 15-20, 20-25, 25-30, 30-35, or 35-40 amino acid residues are deleted at C-terminus of HBHBcAg protein.

2. The nucleic acid molecule according to claim 1, wherein
  (1) the polypeptide carrier is the RBHBcAg-T carrier; and optionally, the nucleic acid molecule is characterized by one or more of the following:
    (i) the RBHBcAg protein has an amino acid sequence as set forth in SEQ ID NO: 1;
    (ii) the amino acid residues from positions 78-83, positions 78-82, positions 78-81, or positions 78-80 at N-terminus of RBHBcAg protein are deleted or substituted with a linker;
    (iii) the linker is a flexible linker;
    (iv) the human T cell epitope is an MHC I or MHC II restricted human T cell epitope;
    (v) the human T cell epitope is selected from human T cell epitopes as set forth in SEQ ID NOs: 87-89;
    (vi) 1, 2, 3, 4, 5, 6, 7, 8, 9, 10 amino acid residues of the amino acid residues from positions 18-27 at N-terminus of RBHBcAg protein are substituted with an MHC I or MHC II restricted human T cell epitope; and/or 1, 2, 3, 4, 5, 6, 7, 8, 9, 10, 11 12, 13, 14, 15, 16, 17, 18, 19, or 20 amino acid residues of the amino acid residues from positions 50-69 at N-terminus of RBHBcAg protein are substituted with an MHC I or MHC II restricted human T cell epitope; and/or 1, 2, 3, 4, 5, 6, 7, 8, 9, 10, 11, 12, 13, 14, 15, 16, 17, 18, 19, 20 or 21 amino acid residues of the amino acid residues from positions 120-140 at N-terminus of RBHBcAg protein are substituted with an MHC I or MHC II restricted human T cell epitope;
    (vii) the amino acid residues at positions 18-27, 50-69 and 120-140 at N-terminus of the RBHBcAg protein are substituted with human T cell epitopes set forth in SEQ ID NO: 87, 88 and 89, respectively;
    (viii) a restriction enzyme cleavage site is introduced at a position of nucleotides encoding the one or more amino acid residues within positions 78-83 at N-terminus of RBHBcAg protein that are deleted;
    (ix) a restriction enzyme cleavage site is introduced in the nucleotide sequence encoding the linker, and/or at either or both of the termini thereof;
    (x) the polypeptide carrier has an amino acid sequence as set forth in SEQ ID NO: 75 or 78; and
    (xi) the nucleic acid molecule comprises a nucleotide sequence as set forth in SEQ ID NO: 81 or 84;
    or
  (2) the polypeptide carrier is the TBHBcAg-T carrier; and optionally, the nucleic acid molecule is characterized by one or more of the following:
    (i) the TBHBcAg protein has an amino acid sequence as set forth in SEQ ID NO: 2;
    (ii) the amino acid residues from positions 80-84, positions 80-83, or positions 80-82, at N-terminus of TBHBcAg protein are deleted or substituted with a linker;
    (iii) the linker is a flexible linker;

(iv) the human cell epitope is an MHC I or MHC II restricted human cell epitope;
(v) the human T cell epitope is selected from human cell epitopes as set forth in SEQ ID NOs: 87-89;
(vi) 1, 2, 3, 4, 5, 6, 7, 8, 9, 10 amino acid residues of the amino acid residues from positions 18-27 at N-terminus of TBHBcAg protein are substituted with an MHC 1 or MHC II restricted human cell epitope; and/or 1, 2; 3, 4, 5, 6, 7, 8, 9, 10, 11, 12, 13, 14, 15, 16, 17, 18, 19, or 20 amino acid residues of the amino acid residues from positions 54-73 at N-terminus of TBHBcAg protein are substituted with an MHC I or MHC II restricted human T cell epitope; and/or 1, 2, 3, 4, 5, 6, 7, 8, 9, 10, 11, 12, 13, 14, 15, 16, 17, 18, 19, 20 or 21 amino acid residues of the amino acid residues from positions 124-144 at N-terminus of TBHBcAg protein are substituted with an MHC 1 or MHC II restricted human T cell epitope;
(vii) the amino acid residues at positions 18-27, 54-73 and 124-144 at N-terminus of the TBHBcAg protein are substituted with human T cell epitopes set forth in SEQ ID NO: 87, 88 and 89, respectively;
(viii) a restriction enzyme cleavage site is introduced at a position of nucleotides encoding the one or more amino acid residues within positions 80-84 at N-terminus of TBHBcAg protein that are deleted;
(ix) a restriction enzyme cleavage site is introduced in the nucleotide sequence encoding the linker, and/or at either or both of the termini thereof;
(x) the polypeptide carrier has an amino acid sequence as set forth in SEQ ID NO: 76 or 79; and
(xi) the nucleic acid molecule comprises a nucleotide sequence as set forth in SEQ ID NO: 82 or 85;
or
(3) the polypeptide carrier is the HBHBcAg-T carrier; and optionally, the nucleic acid molecule is characterized by one or more of the following:
(i) the HBHBcAg protein has an amino acid sequence as set forth in SEQ NO: 3;
(ii) the amino acid residues from positions 78-83, positions 78-82, positions 78-81, or positions 78-80 at N-terminus of HBHBcAg protein are deleted or substituted with a linker;
(iii) the linker is a flexible linker;
(iv) the human cell epitope is an MHC I or MHC II restricted human cell epitope;
(v) the human T cell epitope is selected from human T cell epitopes as set forth in SEQ ID NOs: 87-89;
(vi) 1, 2, 3, 4, 5, 6, 7, 8, 9, 10 amino acid residues of the amino acid residues from positions 18-27 at N-terminus of HBHBcAg protein are substituted with an MHC I or WIC II restricted human T cell epitope; and/or 1, 2, 3, 4, 5, 6, 7, 8, 9, 10, 11, 12, 13, 14, 15, 16, 17, 18, 19, or 20 amino acid residues of the amino acid residues from positions 50-69 at N-terminus of HBHBcAg protein are substituted with an MHC I or MHC II restricted human T cell epitope; and/or 1, 2, 3, 4, 5, 6, 7, 8, 9, 10, 11 12, 13, 14, 15, 16, 17, 18, 19, 20 or 21 amino acid residues of the amino acid residues from positions 120-140 at N-terminus of HBHBcAg protein are substituted with an MHC I or MHC II restricted human T cell epitope; and
(vii) the amino acid residues at positions 18-27, 50-69 and 120-140 at N-terminus of the HBHBcAg protein are substituted with human T cell epitopes set forth in SEQ ID NO: 87, 88 and 89, respectively;
(viii) a restriction enzyme cleavage site is introduced at a position of nucleotides encoding the one or more amino acid residues within positions 78-83 at N-terminus of HBHBcAg protein that are deleted;
(ix) a restriction enzyme cleavage site is introduced in the nucleotide sequence encoding the linker, and/or at either or both of the termini thereof;
(x) the polypeptide carrier has an amino acid sequence as set forth in SEQ ID NO: 77 or 80; and
(xi) the nucleic acid molecule comprises a nucleotide sequence as set forth in SEQ ID NO: 83 or 86.

3. The nucleic acid molecule according to claim 1, wherein the nucleic acid molecule further comprises a nucleotide sequence encoding a target polypeptide, wherein the target polypeptide is heterologous relative to the polypeptide carrier, and the nucleotide sequence encoding the target polypeptide is inserted at a position of nucleotides encoding the one or more amino acid residues that are deleted, or is inserted in the nucleotide sequence encoding the linker or at either or both of the termini thereof.

4. The nucleic acid molecule according to claim 3, wherein the target polypeptide is an epitope peptide; optionally, the epitope peptide is characterized by one of the following:
(i) the epitope peptide comprises: an epitope of HBsAg from human HBV, or an epitope of HIV GP120 protein; or an epitope of human PD-L1;
(ii) the epitope peptide comprises: amino acids from positions 113-135 of HBsAg protein, or amino acids from positions 361-375 of HIV GP120 protein, or amino acids from positions 147-160 of human PD-L1 protein; and
(iii) the epitope peptide has an amino acid sequence selected from SEQ ID NO: 20-22 and 60-62.

5. A vector, comprising the nucleic acid molecule according to claim 1.

6. A host cell, comprising the nucleic acid molecule according to claim 1 or a vector comprising the nucleic acid molecule.

7. A method for presenting a target polypeptide, comprising:
(1) inserting a nucleotide sequence encoding the target polypeptide into the nucleic acid molecule according to claim 1, so as to obtain a nucleic acid molecule encoding a recombinant protein; wherein the nucleotide sequence encoding the target polypeptide is inserted at a position of nucleotides encoding the one or more amino acid residues that are deleted, or inserted in the nucleotide sequence encoding the linker or at either or both of the termini thereof; and
(2) expressing the nucleic acid molecule encoding the recombinant protein in the step (1), to produce the recombinant protein.

8. The method according to claim 7, wherein the target polypeptide is an epitope peptide; optionally, the epitope peptide is characterized by one of the following:
(i) the epitope peptide comprises: an epitope of HBsAg from human HBV, or an epitope of HIV GP120 protein, or an epitope of human PD-L1;
(ii) the epitope peptide comprises: amino acids from positions 113-135 of HBsAg protein, or amino acids from positions 361-375 of HIV GP120 protein, or amino acids from positions 147-160 of human PD-L1 protein; and (iii) the epitope peptide has an amino acid sequence selected from SEQ ID NO: 20-22 and 60-62.

9. A recombinant protein, comprises a polypeptide carrier and a target polypeptide, wherein the target polypeptide is inserted at a position of the one or more amino acid residues that are deleted, or inserted in the linker or at either or both of the termini thereof; and the polypeptide carrier is selected from the following polypeptide carriers:

(1) RBHBcAg-T carrier, which differs from roundleaf bat HBV core antigen protein (RBHBcAg protein) by difference comprising the following:

(1a) one or more amino acid residues of the amino acid residues from positions 78-83 at N-terminus of RBHBcAg protein are deleted or substituted with a linker;

(1b) one or more amino acid residues of the amino acid residues from positions 18-27, one or more amino acid residues of the amino acid residues from positions 50-69 and/or one or more amino acid residues of the amino acid residues from positions 120-140 at N-terminus of RBHBcAg protein are each independently substituted with a human T cell epitope; and (1c) optionally, 1-5, 5-10, 10-15, 15-20, 20-25, 25-30, 30-35, or 35-40 amino acid residues are deleted at C-terminus of RBHBcAg protein;

(2) TBHBcAg-T carrier, which differs from tent-making bat HBV core antigen protein (TBHBcAg protein) by difference comprising the following:

(2a) one or more amino acid residues of the amino acid residues from positions 80-84 at N-terminus of TBHBcAg protein are deleted or substituted with a linker;

(2b) one or more amino acid residues of the amino acid residues from positions 18-27, one or more amino acid residues of the amino acid residues from positions 54-73 and/or one or more amino acid residues of the amino acid residues from positions 124-144 at N-terminus of TBHBcAg protein are each independently substituted with a human T cell epitope; and (2c) optionally, 1-5, 5-10, 10-15, 15-20, 20-25, 25-30, or 30-35 amino acid residues are deleted at C-terminus of TBHBcAg protein; and (3) HBHBcAg-T carrier, which differs from horseshoe bat HBV core antigen protein (HBHBcAg protein) by difference comprising the following:

(3a) one or more amino acid residues of the amino acid residues from positions 78-83 at N-terminus of HBHBcAg protein are deleted or substituted with a linker;

(3b) one or more amino acid residues of the amino acid residues from positions 18-27, one or more amino acid residues of the amino acid residues from positions 50-69 and/or one or more amino acid residues of the amino acid residues from positions 120-140 at N-terminus of HBHBcAg protein are each independently substituted with a human T cell epitope; and (3c) optionally, 1-5, 5-10, 10-15, 15-20, 20-25, 5-30, 30-35, or 35-40 amino acid residues are deleted at C-terminus of HBHBcAg protein.

10. The recombinant protein according to claim 9, characterized by one or more of the following:

(i) the polypeptide carrier has an amino acid sequence selected from SEQ. ID NO: 75-80:

(ii) the target polypeptide is an epitope peptide; optionally, the epitope peptide comprises an epitope of HBsAg from human HBV, an epitope GP120 protein, or an epitope of human PD-L1; or comprises amino acids from positions 113-135 of HBsAg protein, amino acids from positions 361-375 of HIV GP120 protein, or amino acids from positions 147-160 of human PD-L1 protein; or comprises an amino acid sequence selected from SEQ ID NO: 20-22 and 60-62; and (iii) the recombinant protein comprises or consists of an amino acid sequence selected from SEQ ID NO: 90-96.

11. A virus-like particle, comprising the recombinant protein according to claim 9.

12. A pharmaceutical composition, comprising the recombinant protein according to claim 9 or a virus-like particle comprising the recombinant protein, and optionally, one or more pharmaceutically acceptable vehicles or excipients.

13. The pharmaceutical composition according to claim 12, wherein the pharmaceutical composition is a vaccine; and/or, the pharmaceutically acceptable vehicles or excipient is an adjuvant.

14. A method for preventing or treating HBV infection or a disease associated with HBV infection, comprising, administering to a subject in need thereof the recombinant protein according to claim 9 or a virus-like particle comprising the recombinant protein, wherein the target polypeptide is an epitope peptide comprising an antigenic epitope from HBV.

15. The method according to claim 14, characterized by one or more of the following:

(i) the disease associated with HBV infection is hepatitis B;

(ii) the epitope peptide comprises an epitope of HBsAg from human HBV;

(iii) the epitope peptide comprises amino acids from positions 113-135 of HBsAg protein of HBsAg from human HBV;

(iv) the target polypeptide has an amino acid sequence selected from SEQ ID NO: 22 and 60-62; and (v) the recombinant protein comprises or consists of an amino acid sequence selected from SEQ ID NO: 90-96.

16. A polynucleotide, encoding the recombinant protein according to claim 9.

17. A vector, comprising the polynucleotide according to claim 16.

18. A host cell, comprising the polynucleotide according to claim 16 or a vector comprising the polynucleotide.

19. A method for preparing the recombinant protein according to claim 9, comprising culturing a host cell, which comprises a polynucleotide encoding the recombinant protein, under the condition suitable for expressing the recombinant protein, and, recovering the recombinant protein.

\* \* \* \* \*